United States Patent
Ogura

(10) Patent No.: US 7,279,323 B2
(45) Date of Patent: Oct. 9, 2007

(54) METHOD FOR CONDUCTING RECEPTOR-LIGAND ASSOCIATION REACTION AND REACTOR USED THEREFOR

(75) Inventor: Nobuhiko Ogura, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 778 days.

(21) Appl. No.: 10/351,358

(22) Filed: Jan. 27, 2003

(65) Prior Publication Data

US 2003/0143640 A1  Jul. 31, 2003

(30) Foreign Application Priority Data

Jan. 31, 2002 (JP) .............................. 2002-022816

(51) Int. Cl.
C12M 1/34 (2006.01)
C12M 3/00 (2006.01)

(52) U.S. Cl. .............................. 435/287.1; 435/283.1; 435/288.7; 435/7.1; 435/287.7; 436/518; 436/528; 436/529; 436/535; 422/50; 422/68.1; 422/82.05; 422/82.08

(58) Field of Classification Search .................. 422/50, 422/55, 61, 68.1, 82.01, 82.03, 82.08; 436/518, 436/524, 529, 530, 535, 164, 169; 435/4, 435/7.1, 283.1, 287.1, 287.2, 287.7, 28.4
See application file for complete search history.

(56) References Cited

U.S. PATENT DOCUMENTS

| | | | |
|---|---|---|---|
| 4,956,275 A * | 9/1990 | Zuk et al. .................. 235/7.92 |
| 5,245,185 A * | 9/1993 | Busch et al. ................. 250/288 |
| 5,639,423 A | 6/1997 | Northrup et al. |
| 5,639,672 A * | 6/1997 | Burd et al. .................. 436/525 |
| 6,017,696 A * | 1/2000 | Heller ............................ 435/6 |
| 6,168,914 B1 | 1/2001 | Campbell et al. |
| 6,248,596 B1 * | 6/2001 | Durst et al. .................. 436/518 |

(Continued)

FOREIGN PATENT DOCUMENTS

EP 1 096 256 A1 5/2001

(Continued)

OTHER PUBLICATIONS

Ferguson J A et al., "A Fiber-Optic DNA Biosensor Microarray for the Analysis of Gene Expression", Bio/Technology, Nature Publishing Co. New York, US, vol. 14, Dec. 1996, pp. 1681-1684, XP002928887.

*Primary Examiner*—Long V. Le
*Assistant Examiner*—Melanie J. Yu
(74) *Attorney, Agent, or Firm*—Sughrue Mion Pllc.

(57) ABSTRACT

A method for conducting a receptor-ligand association reaction includes the steps of dipping a biochemical analysis unit including a substrate formed with a plurality of absorptive regions which contain receptors or ligands and are formed to be spaced apart from each other in a reaction solution containing a ligand or receptor labeled with a labeling substance, simultaneously inserting a plurality of electrodes into all of the plurality of absorptive regions containing the receptors or ligands and sequentially applying a positive voltage to one of the electrodes at a time while other electrodes are grounded, thereby conducting a receptor-ligand association reaction. According to the this method, it is possible to efficiently react a ligand or receptor with receptors or ligands fixed in the plurality of absorptive regions of the biochemical analysis unit and produce biochemical analysis data having an excellent quantitative characteristic with good repeatability.

44 Claims, 22 Drawing Sheets

U.S. PATENT DOCUMENTS 6,719,888 B1 * 4/2004 Chan et al. ................ 204/435
6,841,379 B2 * 1/2005 Matson .................... 435/287.2

FOREIGN PATENT DOCUMENTS

| | | | |
|---|---|---|---|
| EP | 1 271 132 | A1 | 1/2002 |
| EP | 1 267 169 | A2 | 12/2002 |
| EP | 1 281 966 | A2 | 2/2003 |
| WO | WO 00/14529 | A1 | 3/2000 |
| WO | WO 01/09607 | A1 | 2/2001 |

* cited by examiner

METHOD FOR CONDUCTING RECEPTOR-LIGAND ASSOCIATION REACTION AND REACTOR USED THEREFOR

BACKGROUND OF THE INVENTION

The present invention relates to a method for conducting a receptor-ligand association reaction and a reactor used therefor and, particularly, to a method for conducting a receptor-ligand association reaction and a reactor used therefor which can efficiently react a ligand or receptor with receptors or ligands fixed in a biochemical analysis unit and produce biochemical analysis data having an excellent quantitative characteristic with good repeatability.

DESCRIPTION OF THE PRIOR ART

An autoradiographic analyzing system using as a detecting material for detecting radiation a stimulable phosphor which can absorb, store and record the energy of radiation when it is irradiated with radiation and which, when it is then stimulated by an electromagnetic wave having a specified wavelength, can release stimulated emission whose light amount corresponds to the amount of radiation with which it was irradiated is known, which comprises the steps of introducing a radioactively labeled substance into an organism, using the organism or a part of the tissue of the organism as a specimen, superposing the specimen and a stimulable phosphor sheet formed with a stimulable phosphor layer for a certain period of time, storing and recording radiation energy in a stimulable phosphor contained in the stimulable phosphor layer, scanning the stimulable phosphor layer with an electromagnetic wave to excite the stimulable phosphor, photoelectrically detecting the stimulated emission released from the stimulable phosphor to produce digital image signals, effecting image processing on the obtained digital image signals, and reproducing an image on displaying means such as a CRT or the like or a photographic film (see, for example, Japanese Patent Publication No. 1-60784, Japanese Patent Publication No. 1-60782, Japanese Patent Publication No. 4-3952 and the like).

Unlike the autoradiographic analyzing system using a photographic film, according to the autoradiographic analyzing system using the stimulable phosphor as a detecting material, development, which is chemical processing, becomes unnecessary. Further, it is possible reproduce a desired image by effecting image processing on the obtained image data and effect quantitative analysis using a computer. Use of a stimulable phosphor in these processes is therefore advantageous.

On the other hand, a fluorescence analyzing system using a fluorescent substance as a labeling substance instead of a radioactive labeling substance in the autoradiographic analyzing system is known. According to this system, it is possible to study a genetic sequence, study the expression level of a gene, and to effect separation or identification of protein or estimation of the molecular weight or properties of protein or the like. For example, this system can perform a process including the steps of distributing a plurality of DNA fragments on a gel support by means of electrophoresis after a fluorescent dye was added to a solution containing a plurality of DNA fragments to be distributed, or distributing a plurality of DNA fragments on a gel support containing a fluorescent dye, or dipping a gel support on which a plurality of DNA fragments have been distributed by means of electrophoresis in a solution containing a fluorescent dye, thereby labeling the electrophoresed DNA fragments, exciting the fluorescent dye by a stimulating ray to cause it to release fluorescent light, detecting the released fluorescent light to produce an image and detecting the distribution of the DNA fragments on the gel support. This system can also perform a process including the steps of distributing a plurality of DNA fragments on a gel support by means of electrophoresis, denaturing the DNA fragments, transferring at least a part of the denatured DNA fragments onto a transfer support such as a nitrocellulose support by the Southern-blotting method, hybridizing a probe prepared by labeling target DNA and DNA or RNA complementary thereto with the denatured DNA fragments, thereby selectively labeling only the DNA fragments complementary to the probe DNA or probe RNA, exciting the fluorescent dye by a stimulating ray to cause it to release fluorescent light, detecting the released fluorescent light to produce an image and detecting the distribution of the target DNA on the transfer support. This system can further perform a process including the steps of preparing a DNA probe complementary to DNA containing a target gene labeled by a labeling substance, hybridizing it with DNA on a transfer support, combining an enzyme with the complementary DNA labeled by a labeling substance, causing the enzyme to contact a fluorescent substance, transforming the fluorescent substance to a fluorescent substance having fluorescent light releasing property, exciting the thus produced fluorescent substance by a stimulating ray to release fluorescent light, detecting the fluorescent light to produce an image and detecting the distribution of the target DNA on the transfer support. This fluorescence detecting system is advantageous in that a genetic sequence or the like can be easily detected without using a radioactive substance.

Similarly, there is known a chemiluminescence analyzing system comprising the steps of fixing a substance derived from a living organism such as a protein or a nucleic acid sequence on a support, selectively labeling the substance derived from a living organism with a labeling substance which generates chemiluminescent emission when it contacts a chemiluminescent substrate, contacting the substance derived from a living organism and selectively labeled with the labeling substance and the chemiluminescent substrate, photoelectrically detecting the chemiluminescent emission in the wavelength of visible light generated by the contact of the chemiluminescent substrate and the labeling substance to produce digital image signals, effecting image processing thereon, and reproducing a chemiluminescent image on a display means such as a CRT or a recording material such as a photographic film, thereby obtaining information relating to the high molecular substance such as genetic information.

Further, a micro-array analyzing system has been recently developed, which comprises the steps of using a spotting device to drop at different positions on the surface of a carrier such as a slide glass plate, a membrane filter or the like specific binding substances, which can specifically bind with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substances using a hybridization method or the like with a substance derived from a living organism such as a cell, virus, hormone, tumor marker, enzyme, antibody, antigen, abzyme, other protein, a nuclear acid, cDNA, DNA or mRNA by extraction, isolation or the like and optionally further subjected to chemical processing, chemical modification or the like and which is labeled with a labeling substance such as a fluorescent substance, dye or the like, thereby forming a micro-array, irradiating the micro-array with a stimulating ray, photoelectrically detecting light such as fluorescence emission released from a labeling substance such as a fluorescent substance, dye or the like, and analyzing the substance derived from a living organism. This micro-array analyzing system is advantageous in that a substance derived from a living organism can be analyzed in a short time period by forming a number of spots of specific binding substances at different positions of the surface of a carrier such as a slide glass plate at high density and hybridizing them with a substance derived from a living organism and labeled with a labeling substance.

In addition, a macro-array analyzing system using a radioactive labeling substance as a labeling substance has been further developed, which comprises the steps of using a spotting device to drop at different positions on the surface of a carrier such as a membrane filter or the like specific binding substances, which can specifically bind with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substance using a hybridization method or the like with a substance derived from a living organism such as a cell, virus, hormone, tumor marker, enzyme, antibody, antigen, abzyme, other protein, a nuclear acid, cDNA, DNA or mRNA by extraction, isolation or the like and optionally further subjected to chemical processing, chemical modification or the like and which is labeled with a radioactive labeling substance, thereby forming a macro-array, superposing the macro-array and a stimulable phosphor sheet formed with a stimulable phosphor layer, exposing the stimulable phosphor layer to a radioactive labeling substance, irradiating the stimulable phosphor layer with a stimulating ray to excite the stimulable phosphor, photoelectrically detecting the stimulated emission released from the stimulable phosphor to produce biochemical analysis data, and analyzing the substance derived from a living organism.

In the micro-array analyzing system and the macro-array analyzing system, it is required to produce biochemical analysis data by dropping a solution containing specific binding substances at different positions on the surface of a biochemical analysis unit such as a membrane filter or the like to form a number of spot-like regions, hybridizing a substance derived from a living organism and labeled with a labeling substance such as a radioactive labeling substance, a fluorescent substance or a labeling substance which generates chemiluminescence emission when it contacts a chemiluminescent substrate with the specific binding substances contained in the spot-like regions, thereby selectively labeling the spot-like regions, exposing a stimulable phosphor layer of a stimulable phosphor sheet to a radioactive labeling substance selectively contained in the spot-like regions, scanning the thus exposed stimulable phosphor layer with a stimulating ray, thereby exciting stimulable phosphor contained in the stimulable phosphor layer and photoelectrically detecting stimulated emission released from the stimulable phosphor, or scanning a number of the spot-like regions with a stimulating ray to produce biochemical analysis data, thereby exciting a fluorescent substance contained in a number of the spot-like regions and photoelectrically detecting fluorescence emission released from the fluorescent substance to produce biochemical analysis data, or bringing a labeling substance contained in a number of the spot-like regions into contact with a chemiluminescent substrate and photoelectrically detecting chemiluminescence emission released from the labeling substance to produce biochemical analysis data.

Conventionally, hybridization of specific binding substances and a substance derived from a living organism has been performed by dipping a biochemical analysis unit formed with a number of the spot-like regions containing specific binding substances such as a membrane filter into a hybridization reaction solution containing a substance derived from a living organism and labeled with a labeling substance such as a radioactive labeling substance, a fluorescent substance or a labeling substance which generates chemiluminescence emission when it contacts a chemiluminescent substrate and vibrating the hybridization reaction solution, thereby moving the substance derived from a living organism by convection or diffusion. Therefore, it takes long time for the substance derived from a living organism to associate with the specific binding substances with which the substance derived from a living organism is to be hybridized and the hybridization cannot be efficiently performed. In addition, since the salt concentration of the hybridization reaction solution is high, the membrane filter or other such biochemical analysis unit tends to clog during the process of hybridization. As a result, since it is difficult for the substance derived from a living organism to associate with the specific binding substances absorbed in deep portions of the membrane filter or other such biochemical analysis unit, biochemical analysis data having an excellent quantitative characteristic cannot be produced.

The same problems occur in the case where a receptor and a ligand are associated as in the case of fixing antigens or antibodies in a biochemical analysis unit such as a membrane filter and binding an antibody or an antigen to the thus fixed antigens or antibodies by an antigen-antibody reaction, and the same problems also occur in the case of hybridizing a probe DNA labeled with a hapten such as digoxigenin with a target DNA fixed in a biochemical analysis unit such as a membrane filter, binding an antibody for the hapten such as digoxigenin labeled with an enzyme which generates chemiluminescent emission when it contacts a chemiluminescent substrate or an antibody for the hapten such as digoxigenin labeled with an enzyme which generates fluorescence emission when it contacts a fluorescent substrate with the hapten labeling the probe DNA by an antigen-antibody reaction, thereby labeling the target DNA.

SUMMARY OF THE INVENTION

It is therefore an object of the present invention to provide a method for conducting a receptor-ligand association reaction and a reactor used therefor which can efficiently react a ligand or receptor with receptors or ligands fixed in spot-like regions of a biochemical analysis unit and produce biochemical analysis data having an excellent quantitative characteristic with good repeatability.

The above other objects of the present invention can be accomplished by a method for conducting a receptor-ligand association reaction comprising the steps of dipping a biochemical analysis unit including a substrate formed with a plurality of absorptive regions which contain receptors or ligands and are formed to be spaced apart from each other in a reaction solution containing a ligand or receptor labeled with a labeling substance, inserting at least one electrode into at least one of the plurality of absorptive regions of the biochemical analysis unit and applying a positive voltage to the at least one electrode.

In the present invention, the receptor-ligand association reaction includes a hybridization reaction and an antigen-antibody reaction.

According to the present invention, since a method for conducting a receptor-ligand association reaction comprises the steps of dipping a biochemical analysis unit including a substrate formed with a plurality of absorptive regions which contain receptors or ligands and are formed to be spaced apart from each other in a reaction solution containing a ligand orreceptor labeled with a labeling substance, inserting at least one electrode into at least one of the plurality of absorptive regions of the biochemical analysis unit and applying a positive voltage to the at least one electrode, the ligand or receptor contained in the reaction solution can be attracted to the at least one electrode applied with a positive voltage and forcibly brought into contact with the receptor(s) or ligand(s) absorbed in the absorptive region(s) of the biochemical analysis unit into which the electrode applied with a positive voltage is inserted, thereby selectively associating the ligand or receptor with the receptor(s) or ligand(s). Therefore, it is possible to markedly improve the efficiency of a receptor-ligand association reaction and since it is possible to markedly increase the possibility of association of the ligand or receptor contained in the reaction solution with the receptor(s) or ligand(s) as a target absorbed in the absorptive region(s) of the biochemical analysis unit into which the at least one electrode applied with a positive voltage is inserted, it is possible to selectively associate the ligand or receptor contained in the reaction solution with the receptor(s) or ligand(s) absorbed in the absorptive region of the biochemical analysis unit into which the at least one electrode applied with a positive voltage is inserted in a desired manner.

In a preferred aspect of the present invention, a receptor-ligand association reaction is conducted by simultaneously inserting a plurality of electrodes into all of the plurality of absorptive regions containing the receptors or ligands and applying a positive voltage to the plurality of electrodes.

According to this preferred aspect of the present invention, since a receptor-ligand association reaction is conducted by simultaneously inserting a plurality of electrodes into all of the plurality of absorptive regions containing the receptors or ligands and applying a positive voltage to the plurality of electrodes, the ligand or receptor contained in the reaction solution can be attracted to the plurality of electrodes applied with a positive voltage and forcibly brought into contact with the receptors or ligands absorbed in all of the absorptive regions of the biochemical analysis unit, thereby selectively associating the ligand or receptor with the receptors or ligands. Therefore, it is possible to markedly improve the efficiency of a receptor-ligand association reaction and since it is possible to markedly increase the possibility of association of the ligand or receptor contained in the reaction solution with the receptors or ligands as a target absorbed in the absorptive regions of the biochemical analysis unit, it is possible to selectively associate the ligand or receptor contained in the reaction solution with the receptors or ligands absorbed in the absorptive regions of the biochemical analysis unit in a desired manner.

In another preferred aspect of the present invention, a receptor-ligand association reaction is conducted by simultaneously inserting a plurality of electrodes into all of the plurality of absorptive regions containing the receptors or ligands and sequentially applying a positive voltage to the electrodes at least one at a time while other electrodes are grounded.

According to this preferred aspect of the present invention, since a receptor-ligand association reaction is conducted by simultaneously inserting a plurality of electrodes into all of the plurality of absorptive regions containing the receptors or ligands and sequentially applying a positive voltage to the electrodes at least one at a time while other electrodes are grounded, the ligand or receptor contained in the reaction solution can be attracted to only the electrode applied with a positive voltage and forcibly brought into contact with only the receptor or the ligand absorbed in the absorptive region of the biochemical analysis unit into which the electrode applied with a positive voltage is inserted, thereby selectively associating the ligand or receptor with the receptor or the ligand. Therefore, it is possible to markedly improve the efficiency of a receptor-ligand association reaction and since it is possible to markedly increase the possibility of association of the ligand or receptor contained in the reaction solution with the receptor or the ligand as a target absorbed in the absorptive region of the biochemical analysis unit into which the electrode applied with a positive voltage is inserted, it is possible to selectively associate the ligand or receptor contained in the reaction solution with the receptor or the ligand absorbed in the absorptive region of the biochemical analysis unit into which the electrode applied with a positive voltage is inserted in a desired manner.

Furthermore, according to this preferred aspect of the present invention, when the electrode applied with a positive voltage is thereafter grounded, since a ligand or receptor which was attracted to the electrode applied with a positive voltage but was nevertheless not associated with the receptor or the ligand absorbed in the absorptive region of the biochemical analysis unit into which the electrode applied with a positive voltage was inserted leaves the absorptive region of the biochemical analysis unit into which the electrode was inserted and is returned to the reaction solution and attracted to the electrode next applied with a positive voltage, the ligand or receptor is moved in the reaction solution similarly to the case where the reaction solution is agitated and, as a result, it is possible to more markedly increase the possibility of association of the ligand or receptor contained in the reaction solution with the receptors or ligands as a target absorbed in the absorptive regions of the biochemical analysis unit.

In another preferred aspect of the present invention, a receptor-ligand association reaction is conducted by simultaneously inserting a plurality of electrodes into all of the plurality of absorptive regions containing the receptors or ligands and sequentially applying a positive voltage to electrodes among the plurality of electrodes two or more at a time while other electrodes are grounded.

According to this preferred aspect of the present invention, since a receptor-ligand association reaction is conducted by simultaneously inserting a plurality of electrodes into all of the plurality of absorptive regions containing the receptors or ligands and sequentially applying a positive voltage to electrodes among the plurality of electrodes two or more at a time while other electrodes are grounded, the ligand or receptor contained in the reaction solution can be attracted to only the two or more electrodes applied with a positive voltage and forcibly brought into contact with only the receptors or ligands absorbed in the absorptive regions of the biochemical analysis unit into which the electrodes applied with a positive voltage are inserted, thereby selectively associating the ligand or receptor with the receptors or ligands. Therefore, it is possible to markedly improve the efficiency of a receptor-ligand association reaction and since it is possible to markedly increase the possibility of association of the ligand or receptor contained in the reaction solution with the receptors or ligands as a target absorbed in the absorptive regions of the biochemical analysis unit into which the electrodes applied with a positive voltage are inserted, it is possible to selectively associate the ligand or receptor contained in the reaction solution with the receptors or ligands absorbed in the absorptive regions of the biochemical analysis unit into which the electrodes applied with a positive voltage are inserted in a desired manner.

Furthermore, according to this preferred aspect of the present invention, when the two or more electrodes applied with a positive voltage are thereafter grounded, since a ligand or receptor which was attracted to the two or more electrodes applied with a positive voltage but was nevertheless not associated with the receptors or ligands absorbed in the absorptive regions of the biochemical analysis unit into which the two or more electrodes applied with a positive voltage were inserted leaves the absorptive regions of the biochemical analysis unit into which the two or more electrodes were inserted and is returned to the reaction solution and attracted to the two or more electrodes next applied with a positive voltage, the ligand or receptor is moved in the reaction solution similarly to the case where the reaction solution is agitated and, as a result, it is possible to more markedly increase the possibility of association of the ligand or receptor contained in the reaction solution with the receptors or ligands as a target absorbed in the absorptive regions of the biochemical analysis unit.

In another preferred aspect of the present invention, the plurality of absorptive regions containing receptors or ligands are formed in the substrate of the biochemical analysis unit in the manner of a matrix consisting of m columns and n lines wherein m and n are integers equal to or greater than 2 and a receptor-ligand association reaction is conducted by simultaneously inserting a plurality of electrodes into all of the plurality of absorptive regions containing the receptors or ligands and sequentially applying a positive voltage to the plurality of absorptive regions constituting individual columns of absorptive regions one column at a time while the absorptive regions constituting other columns of absorptive regions are grounded.

According to this preferred aspect of the present invention, since the plurality of absorptive regions containing receptors or ligands are formed in the substrate of the biochemical analysis unit in the manner of a matrix consisting of m columns and n lines wherein m and n are integers equal to or greater than 2 and a receptor-ligand association reaction is conducted by simultaneously inserting a plurality of electrodes into all of the plurality of absorptive regions containing the receptors or ligands and sequentially applying a positive voltage to the plurality of absorptive regions constituting individual columns of absorptive regions one column at a time while the absorptive regions constituting other columns of absorptive regions are grounded, the ligand or receptor contained in the reaction solution can be attracted to only the electrodes of each column applied with a positive voltage and forcibly brought into contact with only the receptors or ligands absorbed in the absorptive regions of the biochemical analysis unit into which each column of the electrodes applied with a positive voltage are inserted, thereby selectively associating the ligand or receptor with the receptors or ligands. Therefore, it is possible to markedly improve the efficiency of a receptor-ligand association reaction and since it is possible to markedly increase the possibility of association of the ligand or receptor contained in the reaction solution with the receptors or ligands as a target absorbed in the absorptive regions of the biochemical analysis unit into which each column of the electrodes applied with a positive voltage are inserted, it is possible to selectively associate the ligand or receptor contained in the reaction solution with the receptors or ligands absorbed in the absorptive regions of the biochemical analysis unit into which each column of the electrodes applied with a positive voltage are inserted in a desired manner.

Furthermore, according to this preferred aspect of the present invention, when each column of the electrodes applied with a positive voltage is thereafter grounded, since a ligand or receptor which was attracted to each column of the electrodes applied with a positive voltage but was nevertheless not associated with the receptors or ligands absorbed in the absorptive regions of the biochemical analysis unit into which each column of the electrodes applied with a positive voltage were inserted leaves the absorptive regions of the biochemical analysis unit into which each column of the electrodes were inserted and is returned to the reaction solution and attracted to each column of the electrodes next applied with a positive voltage, the ligand or receptor is moved in the reaction solution similarly to the case where the reaction solution is agitated and, as a result, it is possible to more markedly increase the possibility of association of the ligand or receptor contained in the reaction solution with the receptors or ligands as a target absorbed in the absorptive regions of the biochemical analysis unit.

In another preferred aspect of the present invention, the plurality of absorptive regions containing the receptors or ligands are formed in the substrate of the biochemical analysis unit in the manner of a matrix consisting of m columns and n lines wherein m and n are integers equal to or greater than 2 and a receptor-ligand association reaction is conducted by simultaneously inserting a plurality of electrodes into all of the plurality of absorptive regions containing the receptors or ligands and sequentially applying a positive voltage to the plurality of absorptive regions constituting two or more columns among the plurality of absorptive regions at a time while the absorptive regions constituting other columns are grounded.

According to this preferred aspect of the present invention, since the plurality of absorptive regions containing the receptors or ligands are formed in the substrate of the biochemical analysis unit in the manner of a matrix consisting of m columns and n lines wherein m and n are integers equal to or greater than 2 and a receptor-ligand association reaction is conducted by simultaneously inserting a plurality of electrodes into all of the plurality of absorptive regions containing the receptors or ligands and sequentially applying a positive voltage to the plurality of absorptive regions constituting two or more columns among the plurality of absorptive regions at a time while the absorptive regions constituting other columns are grounded, the ligand or receptor contained in the reaction solution can be attracted to only the electrodes of two or more columns applied with a positive voltage and forcibly brought into contact with only the receptors or ligands absorbed in the absorptive regions of the biochemical analysis unit into which two or more columns of the electrodes applied with a positive voltage are inserted, thereby selectively associating the ligand or receptor with the receptors or ligands. Therefore, it is possible to markedly improve the efficiency of a receptor-ligand association reaction and since it is possible to markedly increase the possibility of association of the ligand or receptor contained in the reaction solution with the receptors or ligands as a target absorbed in the absorptive regions of the biochemical analysis unit into which two or more columns of the electrodes applied with a positive voltage are inserted, it is possible to selectively associate the ligand or receptor contained in the reaction solution with the receptors or ligands absorbed in the absorptive regions of the biochemical analysis unit into which two or more columns of the electrodes applied with a positive voltage are inserted in a desired manner.

Furthermore, according to this preferred aspect of the present invention, when two or more columns of the electrodes applied with a positive voltage are thereafter grounded, since a ligand or receptor which was attracted to two or more columns of the electrodes applied with a positive voltage but was nevertheless not associated with the receptors or ligands absorbed in the absorptive regions of the biochemical analysis unit into which two or more columns of the electrodes applied with a positive voltage were inserted leaves the absorptive regions of the biochemical analysis unit into which two or more columns of the electrodes were inserted and is returned to the reaction solution and attracted to two or more columns of the electrodes next applied with a positive voltage, the ligand or receptor is moved in the reaction solution similarly to the case where the reaction solution is agitated and, as a result, it is possible to more markedly increase the possibility of association of the ligand or receptor contained in the reaction solution with the receptors or ligands as a target absorbed in the absorptive regions of the biochemical analysis unit.

In another preferred aspect of the present invention, the plurality of absorptive regions containing the receptors or ligands are formed in the substrate of the biochemical analysis unit in the manner of a matrix consisting of m columns and n lines wherein m and n are integers equal to or greater than 2 and a receptor-ligand association reaction is conducted by simultaneously inserting a plurality of electrodes into all of the plurality of absorptive regions containing the receptors or ligands and sequentially applying a positive voltage to the plurality of absorptive regions constituting each line of absorptive regions one line at a time while the absorptive regions constituting other lines of absorptive regions are grounded.

According to this preferred aspect of the present invention, since the plurality of absorptive regions containing the receptors or ligands are formed in the substrate of the biochemical analysis unit in the manner of a matrix consisting of m columns and n lines wherein m and n are integers equal to or greater than 2 and a receptor-ligand association reaction is conducted by simultaneously inserting a plurality of electrodes into all of the plurality of absorptive regions containing the receptors or ligands and sequentially applying a positive voltage to the plurality of absorptive regions constituting each line of absorptive regions one line at a time while the absorptive regions constituting other lines of absorptive regions are grounded, the ligand or receptor contained in the reaction solution can be attracted to only the electrodes of each line applied with a positive voltage and forcibly brought into contact with only the receptors or ligands absorbed in the absorptive regions of the biochemical analysis unit into which each line of the electrodes applied with a positive voltage are inserted, thereby selectively associating the ligand or receptor with the receptors or ligands. Therefore, it is possible to markedly improve the efficiency of a receptor-ligand association reaction and since it is possible to markedly increase the possibility of association of the ligand or receptor contained in the reaction solution with the receptors or ligands as a target absorbed in the absorptive regions of the biochemical analysis unit into which each line of the electrodes applied with a positive voltage are inserted, it is possible to selectively associate the ligand or receptor contained in the reaction solution with the receptors or ligands absorbed in the absorptive regions of the biochemical analysis unit into which each line of the electrodes applied with a positive voltage are inserted in a desired manner.

Furthermore, according to this preferred aspect of the present invention, when each line of the electrodes applied with a positive voltage is thereafter grounded, since a ligand or receptor which was attracted to each line of the electrodes applied with a positive voltage but was nevertheless not associated with the receptors or ligands absorbed in the absorptive regions of the biochemical analysis unit into which each line of the electrodes applied with a positive voltage were inserted leaves the absorptive regions of the biochemical analysis unit into which each line of the electrodes were inserted and is returned to the reaction solution and attracted to each line of the electrodes next applied with a positive voltage, the ligand or receptor is moved in the reaction solution similarly to the case where the reaction solution is agitated and, as a result, it is possible to more markedly increase the possibility of association of the ligand or receptor contained in the reaction solution with the receptors or ligands as a target absorbed in the absorptive regions of the biochemical analysis unit.

In another preferred aspect of the present invention, the plurality of absorptive regions containing the receptors or ligands are formed in the substrate of the biochemical analysis unit in the manner of a matrix consisting of m columns and n lines wherein m and n and n are integers equal to or greater than 2 and a receptor-ligand association reaction is conducted by simultaneously inserting a plurality of electrodes into all of the plurality of absorptive regions containing the receptors or ligands and sequentially applying a positive voltage to the plurality of absorptive regions constituting two or more lines among the plurality of absorptive regions at a time while the absorptive regions constituting other lines are grounded.

According to this preferred aspect of the present invention, since the plurality of absorptive regions containing the receptors or ligands are formed in the substrate of the biochemical analysis unit in the manner of a matrix consisting of m columns and n lines wherein m and n are integers equal to or greater than 2 and a receptor-ligand association reaction is conducted by simultaneously inserting a plurality of electrodes into all of the plurality of absorptive regions containing the receptors or ligands and sequentially applying a positive voltage to the plurality of absorptive regions constituting two or more lines among the plurality of absorptive regions at a time while the absorptive regions constituting other lines are grounded, the ligand or receptor contained in the reaction solution can be attracted to only the electrodes of two or more lines applied with a positive voltage and forcibly brought into contact with only the receptors or ligands absorbed in the absorptive regions of the biochemical analysis unit into which two or more lines of the electrodes applied with a positive voltage are inserted, thereby selectively associating the ligand or receptor with the receptors or ligands. Therefore, it is possible to markedly improve the efficiency of a receptor-ligand association reaction and since it is possible to markedly increase the possibility of association of the ligand or receptor contained in the reaction solution with the receptors or ligands as a target absorbed in the absorptive regions of the biochemical analysis unit into which two or more lines of the electrodes applied with a positive voltage are inserted, it is possible to selectively associate the ligand or receptor contained in the reaction solution with the receptors or ligands absorbed in the absorptive regions of the biochemical analysis unit into which two or more lines of the electrodes applied with a positive voltage are inserted in a desired manner.

Furthermore, according to this preferred aspect of the present invention, when two or more lines of the electrodes applied with a positive voltage are thereafter grounded, since a ligand or receptor which was attracted to two or more lines of the electrodes applied with a positive voltage but was nevertheless not associated with the receptors or ligands absorbed in the absorptive regions of the biochemical analysis unit into which two or more lines of the electrodes applied with a positive voltage were inserted leaves the absorptive regions of the biochemical analysis unit into which two or more lines of the electrodes were inserted and is returned to the reaction solution and attracted to two or more lines of the electrodes next applied with a positive voltage, the ligand or receptor is moved in the reaction solution similarly to the case where the reaction solution is agitated and, as a result, it is possible to more markedly increase the possibility of association of the ligand or receptor contained in the reaction solution with the receptors or ligands as a target absorbed in the absorptive regions of the biochemical analysis unit.

In a preferred aspect of the present invention, a receptor-ligand association reaction is conducted by sequentially inserting at least one electrode applied with a positive voltage at a time into the plurality of absorptive regions of the biochemical analysis unit.

According to this preferred aspect of the present invention, since a receptor-ligand association reaction is conducted by sequentially inserting at least one electrode applied with a positive voltage at a time into the plurality of absorptive regions of the biochemical analysis unit, the ligand or receptor contained in the reaction solution can be attracted to the at least one electrode applied with a positive voltage and which is inserted into the absorptive region of the biochemical analysis unit and forcibly brought into contact with the receptor or the ligand absorbed in the absorptive region of the biochemical analysis unit into which the at least one electrode applied with a positive voltage is inserted, thereby selectively associating the ligand or receptor with the receptor or the ligand. Therefore, it is possible to markedly improve the efficiency of a receptor-ligand association reaction and since it is possible to markedly increase the possibility of association of the ligand or receptor contained in the reaction solution with the receptors or ligands as a target absorbed in the absorptive region of the biochemical analysis unit into which the at least one electrode applied with a positive voltage is inserted, it is possible to selectively associate the ligand or receptor contained in the reaction solution with the receptors or ligands absorbed in the absorptive region of the biochemical analysis unit into which the at least one electrode applied with a positive voltage is inserted in a desired manner.

Furthermore, according to this preferred aspect of the present invention, when the at least one electrode is retracted from the absorptive region of the biochemical analysis unit, since a ligand or receptor which was attracted to the at least one electrode applied with a positive voltage but was nevertheless not associated with the receptor or the ligand absorbed in the absorptive region of the biochemical analysis unit into which the at least one electrode applied with a positive voltage was inserted leaves the absorptive region of the biochemical analysis unit into which the at least one electrode was inserted and is returned to the reaction solution and attracted to at least one electrode next applied with a positive voltage, the ligand or receptor is moved in the reaction solution similarly to the case where the reaction solution is agitated and, as a result, it is possible to more markedly increase the possibility of association of the ligand or receptor contained in the reaction solution with the receptors or ligands as a target absorbed in the absorptive regions of the biochemical analysis unit.

In a further preferred aspect of the present invention, a receptor-ligand association reaction is conducted by sequentially inserting a single electrode applied with a positive voltage into the plurality of absorptive regions of the biochemical analysis unit.

According to this preferred aspect of the present invention, since a receptor-ligand association reaction is conducted by sequentially inserting a single electrode applied with a positive voltage into the plurality of absorptive regions of the biochemical analysis unit, the ligand or receptor contained in the reaction solution can be attracted to the single electrode applied with a positive voltage and inserted into the absorptive region of the biochemical analysis unit and forcibly brought into contact with the receptor or the ligand absorbed in the absorptive region of the biochemical analysis unit into which the single electrode applied with a positive voltage is inserted, thereby selectively associating the ligand or receptor with the receptor or the ligand. Therefore, it is possible to markedly improve the efficiency of a receptor-ligand association reaction and since it is possible to markedly increase the possibility of association of the ligand ore receptor contained in the reaction solution with the receptors or ligands as a target absorbed in the absorptive region of the biochemical analysis unit into which the single electrode applied with a positive voltage is inserted, it is possible to selectively associate the ligand or receptor contained in the reaction solution with the receptors or ligands absorbed in the absorptive region of the biochemical analysis unit into which the single electrode applied with a positive voltage is inserted in a desired manner.

Furthermore, according to this preferred aspect of the present invention, when the single electrode is retracted from the absorptive region of the biochemical analysis unit, since a ligand or receptor which was attracted to the single electrode applied with a positive voltage but was nevertheless not associated with the receptor or the ligand absorbed in the absorptive region of the biochemical analysis unit into which the single electrode applied with a positive voltage was inserted leaves the absorptive region of the biochemical analysis unit into which the single electrode was inserted and is returned to the reaction solution and attracted to a single electrode next applied with a positive voltage, the ligand or receptor is moved in the reaction solution similarly to the case where the reaction solution is agitated and, as a result, it is possible to more markedly increase the possibility of association of the ligand or receptor contained in the reaction solution with the receptors or ligands as a target absorbed in the absorptive regions of the biochemical analysis unit.

In another preferred aspect of the present invention, a receptor-ligand association reaction is conducted by sequentially inserting two or more electrodes applied with a positive voltage at a time into the plurality of absorptive regions of the biochemical analysis unit.

According to this preferred aspect of the present invention, since a receptor-ligand association reaction is conducted by sequentially inserting two or more electrodes applied with a positive voltage at a time into the plurality of absorptive regions of the biochemical analysis unit, the ligand or receptor contained in the reaction solution can be attracted to only the two or more electrodes applied with a positive voltage and which were inserted into the absorptive regions of the biochemical analysis unit and forcibly brought into contact with only the receptors or ligands absorbed in the absorptive regions of the biochemical analysis unit into which the electrodes applied with a positive voltage are inserted, thereby selectively associating the ligand or receptor with the receptors or ligands. Therefore, it is possible to markedly improve the efficiency of a receptor-ligand association reaction and since it is possible to markedly increase the possibility of association of the ligand or receptor contained in the reaction solution with the receptors or ligands as a target absorbed in the absorptive regions of the biochemical analysis unit into which the electrodes applied with a positive voltage are inserted, it is possible to selectively associate the ligand or receptor contained in the reaction solution with the receptors or ligands absorbed in the absorptive regions of the biochemical analysis unit into which the electrodes applied with a positive voltage are inserted in a desired manner.

Furthermore, according to this preferred aspect of the present invention, when the two or more electrodes are retracted from the absorptive regions of the biochemical analysis unit, since a ligand or receptor which was attracted to the two or more electrodes applied with a positive voltage but was nevertheless not associated with the receptors or ligands absorbed in the absorptive regions of the biochemical analysis unit into which the two or more electrodes applied with a positive voltage were inserted leaves the absorptive regions of the biochemical analysis unit into which the two or more electrodes were inserted and is returned to the reaction solution and attracted to the two or more electrodes next applied with a positive voltage, the ligand or receptor is moved in the reaction solution similarly to the case where the reaction solution is agitated and, as a result, it is possible to more markedly increase the possibility of association of the ligand or receptor contained in the reaction solution with the receptors or ligands as a target absorbed in the absorptive regions of the biochemical analysis unit.

In a preferred aspect of the present invention, the reaction solution contains a ligand or receptor labeled with at least one kind of a labeling substance selected from a group consisting of a radioactive labeling substance, a fluorescent substance and a labeling substance which generates chemiluminescence emission when it contacts a chemiluminescent substrate.

In a preferred aspect of the present invention, specific binding substances whose structure or characteristics are known are fixed in the plurality of absorptive regions of the biochemical analysis unit and the method for conducting a receptor-ligand association reaction comprises the steps of dipping the biochemical analysis unit in the reaction solution containing a substance derived from a living organism and labeled with a labeling substance and selectively hybridizing the substance derived from a living organism, labeled with a labeling substance and contained in the reaction solution with the specific binding substances fixed in the plurality of absorptive regions of the biochemical analysis unit.

In a preferred aspect of the present invention, antigens or antibodies are fixed in the plurality of absorptive regions of the biochemical analysis unit and the method for conducting a receptor-ligand association reaction comprises the steps of dipping the biochemical analysis unit in the reaction solution containing an antibody or an antigen labeled with a labeling substance and binding the an antibody or the antigen labeled with the labeling substance with the antigens or the antibodies fixed in the plurality of absorptive regions of the biochemical analysis unit.

In a preferred aspect of the present invention, specific binding substances whose structure or characteristics are known are fixed in the plurality of absorptive regions of the biochemical analysis unit and the method for conducting a receptor-ligand association reaction comprises the steps of dipping the biochemical analysis unit in the reaction solution containing a substance derived from a living organism and labeled with hapten, selectively hybridizing the substance derived from a living organism, labeled with the hapten and contained in the reaction solution with the specific binding substances fixed in the plurality of absorptive regions of the biochemical analysis unit, dipping the biochemical analysis unit in the reaction solution containing an antibody for the hapten labeled with a labeling enzyme, and binding the antibody labeled with the labeling enzyme with the hapten fixed in the plurality of absorptive regions of the biochemical analysis unit by an antigen-antibody reaction.

In a further preferred aspect of the present invention, specific binding substances whose structure or characteristics are known are fixed in the plurality of absorptive regions of the biochemical analysis unit and the method for conducting a receptor-ligand association reaction comprises the steps of dipping the biochemical analysis unit in the reaction solution containing a substance derived from a living organism and labeled with hapten, selectively hybridizing the substance derived from a living organism, labeled with the hapten and contained in the reaction solution with the specific binding substances fixed in the plurality of absorptive regions of the biochemical analysis unit, dipping the biochemical analysis unit in the reaction solution containing an antibody for the hapten labeled with an enzyme which generates chemiluminescence emission when it contacts a chemiluminescent substrate, and binding the antibody labeled with the enzyme with the hapten fixed in the plurality of absorptive regions of the biochemical analysis unit by an antigen-antibody reaction.

In another preferred aspect of the present invention, specific binding substances whose structure or characteristics are known are fixed in the plurality of absorptive regions of the biochemical analysis unit and the method for conducting a receptor-ligand association reaction comprises the steps of dipping the biochemical analysis unit in the reaction solution containing a substance derived from a living organism and labeled with hapten, selectively hybridizing the substance derived from a living organism, labeled with the hapten and contained in the reaction solution with the specific binding substances fixed in the plurality of absorptive regions of the biochemical analysis unit, dipping the biochemical analysis unit in the reaction solution containing an antibody for the hapten labeled with an enzyme which generates a fluorescence substance when it contacts a fluorescent substrate, and binding the antibody labeled with the enzyme with the hapten fixed in the plurality of absorptive regions of the biochemical analysis unit by an antigen-antibody reaction.

In the present invention, illustrative examples of the combination of hapten and antibody include digoxigenin and anti-digoxigenin antibody, theophylline and anti-theophylline antibody, fluorosein and anti-fluorosein antibody, and the like. Further, the combination of biotin and avidin, antigen and antibody may be utilized instead of the combination of hapten and antibody.

The above and other objects of the present invention can be also accomplished by a reactor for conducting a receptor-ligand association reaction comprising a reaction vessel adapted for accommodating a reaction solution containing a ligand or receptor labeled with a labeling substance and provided with a holding section for holding a biochemical analysis unit including a substrate formed with a plurality of absorptive regions which contain receptors or ligands and are formed to be spaced apart from each other, an electric field generating device including a plurality of electrodes disposed at positions corresponding to those of the plurality of absorptive regions of the biochemical analysis unit held by the holding section of the reaction vessel, a positive power source, a ground terminal and a switching means for selectively connecting the plurality of electrodes to the positive power source or the ground terminal, a drive means for moving the electric field generating device between an electric field generating position where the plurality of electrodes are inserted into the corresponding absorptive regions of the biochemical analysis unit held by the holding section of the reaction vessel and a retracted position where the plurality of electrodes are retracted from the corresponding absorptive regions of the biochemical analysis unit held by the holding section of the reaction vessel, and a control means for on and off controlling the positive power source and controlling the switching means.

According to the present invention, since a reactor for conducting a receptor-ligand association reaction comprises a reaction vessel adapted for accommodating a reaction solution containing a ligand or receptor labeled with a labeling substance and provided with a holding section for holding a biochemical analysis unit including a substrate formed with a plurality of absorptive regions which contain receptors or ligands and are formed to be spaced apart from each other, an electric field generating device including a plurality of electrodes disposed at positions corresponding to those of the plurality of absorptive regions of the biochemical analysis unit held by the holding section of the reaction vessel, a positive power source, a ground terminal and a switching means for selectively connecting the plurality of electrodes to the positive power source or the ground terminal, a drive means for moving the electric field generating device between an electric field generating position where the plurality of electrodes are inserted into the corresponding absorptive regions of the biochemical analysis unit held by the holding section of the reaction vessel and a retracted position where the plurality of electrodes are retracted from the corresponding absorptive regions of the biochemical analysis unit held by the holding section of the reaction vessel, and a control means for on and off controlling the positive power source and controlling the switching means, the ligand or receptor contained in the reaction solution can be attracted to only the electrode(s) connected to the positive power source and forcibly brought into contact with only the receptor(s) or ligand(s) absorbed in the absorptive region(s) of the biochemical analysis unit into which the electrode(s) which is (are) connected to the positive power source is (are) inserted to selectively associate the ligand or receptor with the receptor(s) or ligand(s) by controlling the switching means with the control means so as to sequentially connect a certain number of the plurality of electrodes to the positive power source at a time, to simultaneously connect other electrodes to the ground terminal and to turn the positive power source on, while the plurality of electrodes are inserted into the corresponding absorptive regions of the biochemical analysis unit held by the holding section of the reaction vessel by moving the electric field generating device to the electric field generating position. Therefore, it is possible to markedly improve the efficiency of a receptor-ligand association reaction and since it is possible to markedly increase the possibility of association of the ligand or receptor contained in the reaction solution with the receptor(s) or ligand(s) as a target absorbed in the absorptive region(s) of the biochemical analysis unit into which the electrode(s) connected to the positive power source is (are) inserted, it is possible to selectively associate the ligand or receptor contained in the reaction solution with the receptors or ligands absorbed in the absorptive region(s) of the biochemical analysis unit into which the electrode(s) connected to the positive power source is (are) inserted in a desired manner.

Further, according to the present invention, when the switching means is controlled by the control means so as to sequentially connect a certain number of the plurality of electrodes to the positive power source at a time, to simultaneously connect other electrodes to the ground terminal and to turn the positive power source on, while the plurality of electrodes are inserted into the corresponding absorptive regions of the biochemical analysis unit held by the holding section of the reaction vessel by moving the electric field generating device to the electric field generating position and the electrode(s) connected to the positive power source is (are) disconnected from the positive power source and connected to the ground terminal, it is possible to cause a ligand or receptor which was attracted to the electrode(s) connected to the positive power source but was nevertheless not associated with the receptor(s) or ligand(s) absorbed in the absorptive region(s) of the biochemical analysis unit into which the electrode(s) connected to the positive power source was (were) inserted to leave the absorptive region(s) of the biochemical analysis unit into which the electrode(s) was (were) inserted, thereby causing it to return to the reaction solution and to be attracted to an electrode(s) which is (are) next connected to the positive power source. Therefore, it is possible to move the ligand or receptor in the reaction solution similarly to the case where the reaction solution is agitated and, as a result, it is possible to more markedly increase the possibility of association of the ligand or receptor contained in the reaction solution with the receptors or ligands as a target absorbed in the absorptive regions of the biochemical analysis unit.

Moreover, according to the present invention, it is possible to attract the ligand or receptor contained in the reaction solution to all of the electrodes by sequentially connecting all of the electrodes to the positive power source and turning the positive power source on, while the plurality of electrodes are inserted into the corresponding absorptive regions of the biochemical analysis unit held by the holding section of the reaction vessel by moving the electric field generating device to the electric field generating position and to forcibly bring it into contact with the receptors or ligands absorbed in all of the absorptive regions of the biochemical analysis unit, thereby associating the ligand or receptor with the receptors or ligands. Therefore, it is possible to markedly improve the efficiency of a receptor-ligand association reaction and since it is possible to markedly increase the possibility of association of the ligand or receptor contained in the reaction solution with the receptors or ligands as a target absorbed in all of the absorptive regions of the biochemical analysis unit into which the electrode(s) is (are) inserted, it is possible to selectively associate the ligand or receptor contained in the reaction solution with the receptors or ligands absorbed in all of the absorptive regions of the biochemical analysis unit into which the electrode(s) is inserted in a desired manner.

The above and other objects of the present invention can be accomplished by a reactor for conducting a receptor-ligand association reaction comprising a reaction vessel adapted for accommodating a reaction solution containing a ligand or receptor labeled with a labeling substance and provided with a holding section for holding a biochemical analysis unit including a substrate formed with a plurality of absorptive regions which contain receptors or ligands and are formed to be spaced apart from each other, a positive power source, an electric field generating device including at least one electrode connected to the positive power source, and an electrode driving means for moving the at least one electrode between a reaction position where the at least one electrode is inserted into the corresponding absorptive region of the biochemical analysis unit held by the holding section of the reaction vessel and a retracted position where the at least one electrode is retracted from the corresponding absorptive region of the biochemical analysis unit held by the holding section of the reaction vessel, the reactor for conducting a receptor-ligand association reaction further comprising a scanning mechanism for sequentially moving the at least one electrode of the electric field generating device to positions facing the respective absorptive regions of the biochemical analysis unit held by the holding section of the reaction vessel and a control means for controlling the scanning mechanism and the electrode driving means.

According to the present invention, since a reactor for conducting a receptor-ligand association reaction comprises a reaction vessel adapted for accommodating a reaction solution containing a ligand or receptor labeled with a labeling substance and provided with a holding section for holding a biochemical analysis unit including a substrate formed with a plurality of absorptive regions which contain receptors or ligands and are formed to be spaced apart from each other, a positive power source, an electric field generating device including at least one electrode connected to the positive power source, and an electrode driving means for moving the at least one electrode between a reaction position where the at least one electrode is inserted into the corresponding absorptive region of the biochemical analysis unit held by the holding section of the reaction vessel and a retracted position where the at least one electrode is retracted from the corresponding absorptive region of the biochemical analysis unit held by the holding section of the reaction vessel, and the reactor for conducting a receptor-ligand association reaction further comprises a scanning mechanism for sequentially moving the at least one electrode of the electric field generating device to positions facing the respective absorptive regions of the biochemical analysis unit held by the holding section of the reaction vessel and a control means for controlling the scanning mechanism and the electrode driving means, the ligand or receptor contained in the reaction solution can be sequentially attracted to the absorptive region(s) into which the at least one electrode connected to the positive power source is inserted and forcibly brought into contact with the receptor(s) or ligand(s) absorbed in the absorptive region(s) of the biochemical analysis unit into which the at least one electrode is inserted to selectively associate the ligand or receptor with the receptor(s) or ligand(s) by controlling the scanning mechanism and the electrode driving means with the control means so as to sequentially insert the at least one electrode connected to the positive power source in the plurality of absorptive regions of the biochemical analysis unit. Therefore, it is possible to markedly improve the efficiency of a receptor-ligand association reaction and since it is possible to markedly increase the possibility of association of the ligand or receptor contained in the reaction solution with the receptor(s) or ligand(s) as a target absorbed in the absorptive region(s) of the biochemical analysis unit into which the at least one electrode connected to the positive power source is inserted, it is possible to selectively associate the ligand or receptor contained in the reaction solution with the receptors or ligands absorbed in the absorptive region(s) of the biochemical analysis unit into which the at least one electrode is inserted in a desired manner.

Further, according to the present invention, when the scanning mechanism and the electrode driving means are controlled by the control means so as to sequentially insert the at least one electrode connected to the positive power source in the plurality of absorptive regions of the biochemical analysis unit and the at least one electrode is moved from the reaction position to the retracted position, it is possible to cause a ligand or receptor which was attracted to the at least one electrode connected to the positive power source but was nevertheless not associated with the receptor(s) or ligand(s) absorbed in the absorptive region(s) of the biochemical analysis unit into which the at least one electrode connected to the positive power source was inserted to leave the absorptive region(s) of the biochemical analysis unit into which the at least one electrode was inserted, thereby causing it to return to the reaction solution and to be attracted to at least one electrode which is next connected to the positive power source. Therefore, it is possible to move the receptor or the ligand in the reaction solution similarly to the case where the reaction solution is agitated and, as a result, it is possible to more markedly increase the possibility of association of the ligand or receptor contained in the reaction solution with the receptors or ligands as a target absorbed in the absorptive regions of the biochemical analysis unit.

In a preferred aspect of the present invention, the electric field generating device includes a single electrode.

According to this preferred aspect of the present invention, the ligand or receptor contained in the reaction solution can be sequentially attracted to each absorptive region into which the single electrode connected to the positive power source is inserted and forcibly brought into contact with the receptor or the ligand absorbed in the absorptive region of the biochemical analysis unit into which the single electrode is inserted to selectively associate the ligand or receptor with the receptor or the ligand by controlling the scanning mechanism and the electrode driving means with the control means so as to sequentially insert the single electrode connected to the positive power source in the plurality of absorptive regions of the biochemical analysis unit. Therefore, it is possible to markedly improve the efficiency of a receptor-ligand association reaction and since it is possible to markedly increase the possibility of association of the ligand or receptor contained in the reaction solution with the receptor or the ligand as a target absorbed in the absorptive region of the biochemical analysis unit into which the single electrode connected to the positive power source is inserted, it is possible to selectively associate the ligand or receptor contained in the reaction solution with the receptor or the ligand absorbed in the absorptive region of the biochemical analysis unit into which the single electrode is inserted in a desired manner.

Moreover, according to this preferred aspect of the present invention, when the scanning mechanism and the electrode driving means are controlled by the control means so as to sequentially insert the single electrode connected to the positive power source in the plurality of absorptive regions of the biochemical analysis unit and the single electrode is moved from the reaction position to the retracted position, it is possible to cause a ligand or receptor which was attracted to the single electrode connected to the positive power source but was nevertheless not associated with the receptor or the ligand absorbed in the absorptive region of the biochemical analysis unit into which the single electrode connected to the positive power source was inserted to leave the absorptive region of the biochemical analysis unit into which the single electrode was inserted, thereby causing it to return to the reaction solution and to be attracted to a single electrode which is next connected to the positive power source. Therefore, it is possible to move the ligand or receptor in the reaction solution similarly to the case where the reaction solution is agitated and, as a result, it is possible to more markedly increase the possibility of association of the ligand or receptor contained in the reaction solution with the receptors or ligands as a target absorbed in the absorptive regions of the biochemical analysis unit.

In a preferred aspect of the present invention, the electric field generating device includes two or more electrodes.

According to this preferred aspect of the present invention, the ligand or receptor contained in the reaction solution can be sequentially attracted to the absorptive regions into which two or more electrodes connected to the positive power source are inserted and forcibly brought into contact with the receptors or ligands absorbed in the absorptive regions of the biochemical analysis unit into which the two or more electrodes are inserted to selectively associate the ligand or receptor with the receptors or ligands by controlling the scanning mechanism and the electrode driving means with the control means so as to sequentially insert the two or more electrodes connected to the positive power source in the plurality of absorptive regions of the biochemical analysis unit. Therefore, it is possible to markedly improve the efficiency of a receptor-ligand association reaction and since it is possible to markedly increase the possibility of association of the ligand or receptor contained in the reaction solution with the receptors or ligands as a target absorbed in the absorptive regions of the biochemical analysis unit into which the two or more electrodes connected to the positive power source are inserted, it is possible to selectively associate the ligand or receptor contained in the reaction solution with the receptors or ligands absorbed in the absorptive regions of the biochemical analysis unit into which the two or more electrodes are inserted in a desired manner.

Moreover, according to this preferred aspect of the present invention, when the scanning mechanism and the electrode driving means are controlled by the control means so as to sequentially insert the two or more electrodes connected to the positive power source in the plurality of absorptive regions of the biochemical analysis unit and the two or more electrodes are moved from the reaction position to the retracted position, it is possible to cause a ligand or receptor which was attracted to the two or more electrodes connected to the positive power source but was nevertheless not associated with the receptors or ligands absorbed in the absorptive regions of the biochemical analysis unit into which the two or more electrodes connected to the positive power source were inserted to leave the absorptive region of the biochemical analysis unit into which the two or more electrodes were inserted, thereby causing it to return to the reaction solution and to be attracted to two or more electrodes which are next connected to the positive power source. Therefore, it is possible to move the ligand or receptor in the reaction solution similarly to the case where the reaction solution is agitated and, as a result, it is possible to more markedly increase the possibility of association of the ligand or receptor contained in the reaction solution with the receptors or ligands as a target absorbed in the absorptive regions of the biochemical analysis unit.

In a preferred aspect of the present invention, the plurality of absorptive regions containing the receptors or ligands are formed in the substrate of the biochemical analysis unit in the manner of a matrix consisting of m columns and n lines wherein m and n are integers equal to or greater than 2 and the electric field generating device includes m electrodes correspondingly to the absorptive regions constituting one column of the absorptive regions formed in the substrate of the biochemical analysis unit.

According to this preferred aspect of the present invention, since the plurality of absorptive regions containing the receptors or ligands are formed in the substrate of the biochemical analysis unit in the manner of a matrix consisting of m columns and n lines wherein m and n are integers equal to or greater than 2 and the electric field generating device includes m electrodes correspondingly to the absorptive regions constituting one column of the absorptive regions formed in the substrate of the biochemical analysis unit, the ligand or receptor contained in the reaction solution can be sequentially attracted to the absorptive regions constituting individual columns of absorptive regions formed in the substrate of the biochemical analysis unit and into which the m electrodes are inserted by controlling the scanning mechanism and the electrode driving means with the control means so as to sequentially insert the m electrodes connected to the positive power source into the absorptive regions constituting individual columns of absorptive regions formed in the substrate of the biochemical analysis unit and can be forcibly brought into contact with only the receptors or ligands absorbed in the absorptive regions constituting individual columns of absorptive regions formed in the substrate of the biochemical analysis unit and into which the m electrodes are inserted, thereby selectively associating the ligand or receptor with the receptors or ligands. Therefore, it is possible to markedly improve the efficiency of a receptor-ligand association reaction and since it is possible to markedly increase the possibility of association of the ligand or receptor contained in the reaction solution with the receptors or ligands as a target absorbed in individual columns of absorptive regions of the biochemical analysis unit into which the m electrodes connected to the positive power source are inserted, it is possible to selectively associate the ligand or receptor contained in the reaction solution with the receptors or ligands absorbed in the absorptive regions of the biochemical analysis unit into which the m electrodes are inserted in a desired manner.

Moreover, according to this preferred aspect of the present invention, when the scanning mechanism and the electrode driving means are controlled by the control means so as to sequentially insert the m electrodes connected to the positive power source into the absorptive regions constituting individual columns of absorptive regions formed in the substrate of the biochemical analysis unit and the m electrodes are retracted from the reaction position to the retracted position, a ligand or receptor which was attracted to the absorptive regions constituting a column of the absorptive regions formed in the substrate of the biochemical analysis unit and into which the m electrodes were inserted but was nevertheless not associated with the receptors or ligand absorbed in the column of the absorptive regions into which the m electrodes were inserted can leave the absorptive regions into which the m electrodes were inserted to be returned into the reaction solution and attracted to the column of absorptive regions of the biochemical analysis unit into which the m electrodes are next inserted. Therefore, the ligand or receptor can be moved in the reaction solution similarly to the case where the reaction solution is agitated and it is possible to more markedly increase the possibility of association of the ligand or receptor contained in the reaction solution with the receptors or ligands as a target absorbed in the absorptive regions of the biochemical analysis unit.

In a preferred aspect of the present invention, the plurality of absorptive regions containing the receptors or ligands are formed in the substrate of the biochemical analysis unit in the manner of a matrix consisting of m columns and n lines wherein m and n are integers equal to or greater than 2 and the electric field generating device includes n electrodes correspondingly to the absorptive regions constituting one line of the absorptive regions formed in the substrate of the biochemical analysis unit.

According to this preferred aspect of the present invention, since the plurality of absorptive regions containing the receptors or ligands are formed in the substrate of the biochemical analysis unit in the manner of a matrix consisting of m columns and n lines wherein m and n are integers equal to or greater than 2 and the electric field generating device includes n electrodes correspondingly to the absorptive regions constituting one line of the absorptive regions formed in the substrate of the biochemical analysis unit, the ligand or receptor contained in the reaction solution can be sequentially attracted to the absorptive regions constituting one line of the absorptive regions formed in the substrate of the biochemical analysis unit and into which the n electrodes are inserted by controlling the scanning mechanism and the electrode driving means with the control means so as to sequentially insert the n electrodes connected to the positive power source into the absorptive regions constituting individual lines of absorptive regions formed in the substrate of the biochemical analysis unit and can be forcibly brought into contact with only the receptors or ligands absorbed in the absorptive regions constituting individual lines of the absorptive regions formed in the substrate of the biochemical analysis unit and into which the n electrodes are inserted, thereby selectively associating the ligand or receptor with the receptors or ligands. Therefore, it is possible to markedly improve the efficiency of a receptor-ligand association reaction and since it is possible to markedly increase the possibility of association of the ligand or receptor contained in the reaction solution with the receptors or ligands as a target absorbed in individual lines of absorptive regions of the biochemical analysis unit into which the m electrodes connected to the positive power source are inserted, it is possible to selectively associate the ligand or receptor contained in the reaction solution with the receptors or ligands absorbed in the absorptive regions of the biochemical analysis unit into which the n electrodes are inserted in a desired manner.

Moreover, according to this preferred aspect of the present invention, when the scanning mechanism and the electrode driving means are controlled by the control means so as to sequentially insert the n electrodes connected to the positive power source into the absorptive regions constituting individual lines of absorptive regions formed in the substrate of the biochemical analysis unit and the n electrodes are retracted from the reaction position to the retracted position, a ligand or receptor which was attracted to the absorptive regions constituting a line of the absorptive regions formed in the substrate of the biochemical analysis unit and into which the n electrodes were inserted but was nevertheless not associated with the receptors or ligand absorbed in the line of the absorptive regions into which the n electrodes were inserted can leave the absorptive regions into which the n electrodes were inserted to be returned into the reaction solution and attracted to the line of absorptive regions of the biochemical analysis unit into which the n electrodes are next inserted. Therefore, the ligand or receptor can be moved in the reaction solution similarly to the case where the reaction solution is agitated and it is possible to more markedly increase the possibility of association of the ligand or receptor contained in the reaction solution with the receptors or ligands as a target absorbed in the absorptive regions of the biochemical analysis unit.

In a preferred aspect of the present invention, the plurality of absorptive regions containing the receptors or ligands are formed in the substrate of the biochemical analysis unit in the manner of a matrix consisting of m columns and n lines wherein m and n are integers equal to or greater than 2 and the electric field generating device includes j×n electrodes correspondingly to the absorptive regions constituting j columns of absorptive regions formed in the substrate of the biochemical analysis unit wherein j is an integer equal to or greater than 2 and a divisor of n.

According to this preferred aspect of the present invention, since the plurality of absorptive regions containing the receptors or ligands are formed in the substrate of the biochemical analysis unit in the manner of a matrix consisting of m columns and n lines wherein m and n are integers equal to or greater than 2 and the electric field generating device includes j×n electrodes correspondingly to the absorptive regions constituting j columns of absorptive regions formed in the substrate of the biochemical analysis unit wherein j is an integer equal to or greater than 2 and a divisor of n, the ligand or receptor contained in the reaction solution can be sequentially attracted to the absorptive regions constituting sets of j columns of absorptive regions formed in the substrate of the biochemical analysis unit and into which the j×n electrodes are inserted by controlling the scanning mechanism and the electrode driving means with the control means so as to sequentially insert the j×n electrodes connected to the positive power source into the absorptive regions constituting sets of j columns of absorptive regions formed in the substrate of the biochemical analysis unit and can be forcibly brought into contact with only the receptors or ligands absorbed in the absorptive regions constituting sets of j columns of absorptive regions formed in the substrate of the biochemical analysis unit and into which the j×n electrodes are inserted, thereby selectively associating the ligand or receptor with the receptors or ligands. Therefore, it is possible to markedly improve the efficiency of a receptor-ligand association reaction and since it is possible to markedly increase the possibility of association of the ligand or receptor contained in the reaction solution with the receptors or ligands as a target absorbed in sets of j columns of absorptive regions of the biochemical analysis unit into which the j×n electrodes connected to the positive power source are inserted, it is possible to selectively associate the ligand or receptor contained in the reaction solution with the receptors or ligands absorbed in the absorptive regions of the biochemical analysis unit into which the j×n electrodes are inserted in a desired manner.

Moreover, according to this preferred aspect of the present invention, when the scanning mechanism and the electrode driving means are controlled by the control means so as to sequentially insert the j×n electrodes connected to the positive power source into the absorptive regions constituting sets of j columns of absorptive regions formed in the substrate of the biochemical analysis unit and the j×n electrodes are retracted from the reaction position to the retracted position, a ligand or receptor which was attracted to the absorptive regions constituting a set of j columns of absorptive regions formed in the substrate of the biochemical analysis unit and into which the j×n electrodes were inserted but was nevertheless not associated with the receptors or ligand absorbed in the j columns of absorptive regions into which the j×n electrodes were inserted can leave the absorptive regions into which the j×n electrodes were inserted to be returned into the reaction solution and attracted to the set of j columns of absorptive regions of the biochemical analysis unit into which the j×n electrodes are next inserted. Therefore, the ligand or receptor can be moved in the reaction solution similarly to the case where the reaction solution is agitated and it is possible to more markedly increase the possibility of association of the ligand or receptor contained in the reaction solution with the receptors or ligands as a target absorbed in the absorptive regions of the biochemical analysis unit.

In a preferred aspect of the present invention, the plurality of absorptive regions containing the receptors or ligands are formed in the substrate of the biochemical analysis unit in the manner of a matrix consisting of m columns and n lines wherein m and n are integers equal to or greater than 2 and the electric field generating device includes k×m electrodes correspondingly to the absorptive regions constituting k lines of absorptive regions formed in the substrate of the biochemical analysis unit wherein k is an integer equal to or greater than 2 and a divisor of m.

According to this preferred aspect of the present invention, since the plurality of absorptive regions containing the receptors or ligands are formed in the substrate of the biochemical analysis unit in the manner of a matrix consisting of m columns and n lines wherein m and n are integers equal to or greater than 2 and the electric field generating device includes k×m electrodes correspondingly to the absorptive regions constituting k lines of absorptive regions formed in the substrate of the biochemical analysis unit wherein k is an integer equal to or greater than 2 and a divisor of m, the ligand or receptor contained in the reaction solution can be sequentially attracted to the absorptive regions constituting sets of k lines of absorptive regions formed in the substrate of the biochemical analysis unit and into which the k×m electrodes are inserted by controlling the scanning mechanism and the electrode driving means with the control means so as to sequentially insert the k×m electrodes connected to the positive power source into the absorptive regions constituting sets of k lines of absorptive regions formed in the substrate of the biochemical analysis unit and can be forcibly brought into contact with only the receptors or ligands absorbed in the absorptive regions constituting sets of k lines of absorptive regions formed in the substrate of the biochemical analysis unit and into which the k×m electrodes are inserted, thereby selectively associating the ligand or receptor with the receptors or ligands. Therefore, it is possible to markedly improve the efficiency of a receptor-ligand association reaction and since it is possible to markedly increase the possibility of association of the ligand or receptor contained in the reaction solution with the receptors or ligands as a target absorbed in set of k lines of absorptive regions of the biochemical analysis unit into which the k×m electrodes connected to the positive power source are inserted, it is possible to selectively associate the ligand or receptor contained in the reaction solution with the receptors or ligands absorbed in the absorptive regions of the biochemical analysis unit into which the k×m electrodes are inserted in a desired manner.

Moreover, according to this preferred aspect of the present invention, when the scanning mechanism and the electrode driving means are controlled by the control means so as to sequentially insert the k×m electrodes connected to the positive power source into the absorptive regions constituting sets of k lines of absorptive regions formed in the substrate of the biochemical analysis unit and the k×m electrodes are retracted from the reaction position to the retracted position, a ligand or receptor which was attracted to the absorptive regions constituting a set of k lines of absorptive regions formed in the substrate of the biochemical analysis unit and into which the k×m electrodes were inserted but was nevertheless not associated with the receptors or ligand absorbed in the k lines of absorptive regions into which the k×m electrodes were inserted can leave the absorptive regions into which the k×m electrodes were inserted to be returned into the reaction solution and attracted to the set of k lines of absorptive regions of the biochemical analysis unit into which the k×m electrodes are next inserted. Therefore, the ligand or receptor can be moved in the reaction solution similarly to the case where the reaction solution is agitated and it is possible to more markedly increase the possibility of association of the ligand or receptor contained in the reaction solution with the receptors or ligands as a target absorbed in the absorptive regions of the biochemical analysis unit.

In a preferred aspect of the present invention, the biochemical analysis unit includes a substrate formed with a plurality of holes to be spaced apart from each other and the plurality of absorptive regions are formed by charging an absorptive material in the plurality of holes formed in the substrate and causing the absorptive material charged in the plurality of holes in to contain the receptors or ligands.

In a further preferred aspect of the present invention, the biochemical analysis unit includes a substrate formed with a plurality of through-holes to be spaced apart from each other and the plurality of absorptive regions are formed by charging an absorptive material in the plurality of through-holes formed in the substrate and causing the absorptive material charged in the plurality of through-holes to contain the receptors or ligands.

In a further preferred aspect of the present invention, the biochemical analysis unit includes a substrate formed with a plurality of through-holes to be spaced apart from each other and the plurality of absorptive regions are formed by pressing an absorptive membrane containing an absorptive material into the plurality of through-holes formed in the substrate and causing the absorptive membrane pressed in the plurality of through-holes to contain the receptors or ligands.

In another preferred aspect of the present invention, the biochemical analysis unit includes a substrate formed with a plurality of recesses to be spaced apart from each other and the plurality of absorptive regions are formed by charging an absorptive material in the plurality of recesses formed in the substrate and causing the absorptive material charged in the plurality of recesses to contain the receptors or ligands.

In another preferred aspect of the present invention, the biochemical analysis unit includes an absorptive substrate containing an absorptive material and at least one substrate formed with a plurality of through-holes to be spaced apart from each other and being in close contact with at least one surface of the absorptive substrate and the plurality of absorptive regions are formed by causing the absorptive substrate within the plurality of through-holes formed in the substrate to contain the receptors or ligands.

In a preferred aspect of the present invention, the substrate of the biochemical analysis unit has a property capable of attenuating radiation energy.

According to this preferred aspect of the present invention, since the substrate of the biochemical analysis unit further has a property capable of attenuating radiation energy, in the case of forming the plurality of absorptive regions containing specific binding substances as receptors or ligands in the biochemical analysis unit at a high density, selectively hybridizing the specific binding substances contained in the plurality of absorptive regions of the biochemical analysis unit with a substance derived from a living organism as a ligand or receptor and labeled with a radioactive labeling substance to selectively label them, superposing the biochemical analysis unit on a stimulable phosphor sheet formed with a stimulable phosphor layer and exposing the stimulable phosphor layer formed on a support of the stimulable phosphor sheet to the radioactive labeling substance selectively contained in the plurality of absorptive regions, it is possible to effectively prevent electron beams ($\beta$ rays) released from the radioactive labeling substance contained in the individual absorptive regions from being scattered in the substrate of the biochemical analysis unit. Therefore, since it is possible to cause electron beams ($\beta$ rays) released from the radioactive labeling substance contained in the individual absorptive regions to selectively impinge on the corresponding regions of the stimulable phosphor layer, whereby only the corresponding regions of the stimulable phosphor layer can be exposed to electron beams ($\beta$ rays), it is possible to produce biochemical analysis data having an excellent quantitative characteristic with a high resolution by scanning the stimulable phosphor layer exposed to the radioactive labeling substance with a stimulating ray and photoelectrically detecting stimulated emission released from the stimulable phosphor layer.

In a preferred aspect of the present invention, the substrate of the biochemical analysis unit is made of a material that reduces the energy of radiation to $1/5$ or less when the radiation travels in the substrate by a distance equal to that between neighboring absorptive regions.

In a further preferred aspect of the present invention, the substrate of the biochemical analysis unit is made of a material that reduces the energy of radiation to $1/10$ or less when the radiation travels in the substrate by a distance equal to that between neighboring absorptive regions.

In a further preferred aspect of the present invention, the substrate of the biochemical analysis unit is made of a material that reduces the energy of radiation to $1/50$ or less when the radiation travels in the substrate by a distance equal to that between neighboring absorptive regions.

In a further preferred aspect of the present invention, the substrate of the biochemical analysis unit is made of a material that reduces the energy of radiation to $1/100$ or less when the radiation travels in the substrate by a distance equal to that between neighboring absorptive regions.

In a further preferred aspect of the present invention, the substrate of the biochemical analysis unit is made of a material that reduces the energy of radiation to $1/500$ or less when the radiation travels in the substrate by a distance equal to that between neighboring absorptive regions.

In a further preferred aspect of the present invention, the substrate of the biochemical analysis unit is made of a material that reduces the energy of radiation to $1/1,000$ or less when the radiation travels in the substrate by a distance equal to that between neighboring absorptive regions.

In a preferred aspect of the present invention, the substrate of the biochemical analysis unit has a property capable of attenuating light energy.

According to this preferred aspect of the present invention, since the substrate of the biochemical analysis unit has a property capable of attenuating light energy, in the case of forming the plurality of absorptive regions containing specific binding substances as receptors or ligands in the biochemical analysis unit at a high density, selectively hybridizing the specific binding substances contained in the plurality of absorptive regions of the biochemical analysis unit with a substance derived from a living organism as a ligand or receptor and labeled with a fluorescent substance, irradiating the plurality of absorptive regions with a stimulating ray, thereby stimulating a fluorescent substance selectively contained in the plurality of absorptive regions, and photoelectrically detecting fluorescence emission released from the plurality of absorptive regions, it is possible to effectively prevent fluorescence emission released from the individual absorptive regions from being scattered in the substrate of the biochemical analysis unit and mixing fluorescence emission released from neighboring absorptive regions. Further, in the case of forming the plurality of absorptive regions containing specific binding substances as receptors or ligands in the biochemical analysis unit at a high density, selectively hybridizing the specific binding substances contained in the plurality of absorptive regions of the biochemical analysis unit with a substance derived from a living organism as a ligand or receptor and labeled with a labeling substance which generates chemiluminescence emission when it contacts a chemiluminescent substrate, and bringing the biochemical analysis unit into contact with a chemiluminescent substrate, it is possible to effectively prevent chemiluminescence emission released from the individual absorptive regions from being scattered in the substrate of the biochemical analysis unit and mixing chemiluminescence emission released from neighboring absorptive regions. Therefore, it is possible to produce biochemical analysis data having an excellent quantitative characteristic with a high resolution by photoelectrically detecting fluorescence emission or chemiluminescence emission.

In a preferred aspect of the present invention, the substrate of the biochemical analysis unit is made of a material that reduces the energy of light to $1/5$ or less when the light travels in the substrate by a distance equal to that between neighboring absorptive regions.

In a further preferred aspect of the present invention, the substrate of the biochemical analysis unit is made of a material that reduces the energy of light to $1/10$ or less when the light travels in the substrate by a distance equal to that between neighboring absorptive regions.

In a further preferred aspect of the present invention, the substrate of the biochemical analysis unit is made of a material that reduces the energy of light to $1/50$ or less when the light travels in the substrate by a distance equal to that between neighboring absorptive regions.

In a further preferred aspect of the present invention, the substrate of the biochemical analysis unit is made of a material that reduces the energy of light to $1/100$ or less when the light travels in the substrate by a distance equal to that between neighboring absorptive regions.

In a further preferred aspect of the present invention, the substrate of the biochemical analysis unit is made of a material that reduces the energy of light to $1/500$ or less when the light travels in the substrate by a distance equal to that between neighboring absorptive regions.

In a further preferred aspect of the present invention, the substrate of the biochemical analysis unit is made of a material that reduces the energy of light to $1/1,000$ or less when the light travels in the substrate by a distance equal to that between neighboring absorptive regions.

In a preferred aspect of the present invention, the biochemical analysis unit is formed with 10 or more absorptive regions.

In a further preferred aspect of the present invention, the biochemical analysis unit is formed with 50 or more absorptive regions.

In a further preferred aspect of the present invention, the biochemical analysis unit is formed with 100 or more absorptive regions.

In a further preferred aspect of the present invention, the biochemical analysis unit is formed with 500 or more absorptive regions.

In a further preferred aspect of the present invention, the biochemical analysis unit is formed with 1,000 or more absorptive regions.

In a further preferred aspect of the present invention, the biochemical analysis unit is formed with 5,000 or more absorptive regions.

In a further preferred aspect of the present invention, the biochemical analysis unit is formed with 10,000 or more absorptive regions.

In a further preferred aspect of the present invention, the biochemical analysis unit is formed with 50,000 or more absorptive regions.

In a further preferred aspect of the present invention, the substrate of the biochemical analysis unit is formed with 100,000 or more absorptive regions.

In a preferred aspect of the present invention, each of the plurality of absorptive regions formed in the biochemical analysis unit has a size of less than 5 mm$^2$.

In a further preferred aspect of the present invention, each of the plurality of absorptive regions formed in the biochemical analysis unit has a size of less than 1 mm$^2$.

In a further preferred aspect of the present invention, each of the plurality of absorptive regions formed in the biochemical analysis unit has a size of less than 0.5 mm$^2$.

In a further preferred aspect of the present invention, each of the plurality of absorptive regions formed in the biochemical analysis unit has a size of less than 0.1 mm$^2$.

In a further preferred aspect of the present invention, each of the plurality of absorptive regions formed in the biochemical analysis unit has a size of less than 0.05 mm$^2$.

In a further preferred aspect of the present invention, each of the plurality of absorptive regions formed in the biochemical analysis unit has a size of less than 0.01 mm$^2$.

In a preferred aspect of the present invention, the plurality of absorptive regions are formed in the biochemical analysis unit at a density of 10 or more per cm$^2$.

In a further preferred aspect of the present invention, the plurality of absorptive regions are formed in the biochemical analysis unit at a density of 50 or more per cm$^2$.

In a further preferred aspect of the present invention, the plurality of absorptive regions are formed in the biochemical analysis unit at a density of 100 or more per cm$^2$.

In a further preferred aspect of the present invention, the plurality of absorptive regions are formed in the biochemical analysis unit at a density of 500 or more per cm$^2$.

In a further preferred aspect of the present invention, the plurality of absorptive regions are formed in the biochemical analysis unit at a density of 1,000 or more per cm$^2$.

In a further preferred aspect of the present invention, the plurality of absorptive regions are formed in the biochemical analysis unit at a density of 5,000 or more per cm$^2$.

In a further preferred aspect of the present invention, the plurality of absorptive regions are formed in the biochemical analysis unit at a density of 10,000 or more per cm$^2$.

In a further preferred aspect of the present invention, the plurality of absorptive regions are formed in the biochemical analysis unit at a density of 50,000 or more per cm$^2$.

In a further preferred aspect of the present invention, the plurality of absorptive regions are formed in the biochemical analysis unit at a density of 100,000 or more per cm$^2$.

In a preferred aspect of the present invention, the plurality of absorptive regions are formed in the biochemical analysis unit in a regular pattern.

In a preferred aspect of the present invention, each of the plurality of absorptive regions is formed in the biochemical analysis unit so as to have having a substantially circular shape.

In the present invention, the material for forming the substrate of the biochemical analysis unit preferably has a property capable of attenuating radiation energy and/or light energy but is not particularly limited. The material for forming the substrate of the biochemical analysis unit may be any type of an inorganic compound material or an organic compound material and the substrate of the biochemical analysis unit can preferably be formed of a metal material, a ceramic material or a plastic material.

Illustrative examples of inorganic compound materials preferably usable for forming the substrate of the biochemical analysis unit in the present invention include metals such as gold, silver, copper, zinc, aluminum, titanium, tantalum, chromium, iron, nickel, cobalt, lead, tin, selenium and the like; alloys such as brass, stainless steel, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. These may have either a monocrystal structure or a polycrystal sintered structure such as amorphous, ceramic or the like.

In the present invention, a high molecular compound can preferably be used as an organic compound material preferably usable for forming the substrate of the biochemical analysis unit. Illustrative examples of high molecular compounds preferably usable for forming the substrate of the biochemical analysis unit in the present invention include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifluoroethylene; polycarbonate; polyesters such as polyethylene naphthalate, polyethylene terephthalate and the like; nylons such as nylon-6, nylon-6,6, nylon-4,10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Since the capability of attenuating radiation energy generally increases as specific gravity increases, the substrate of the biochemical analysis unit is preferably formed of a compound material or a composite material having specific gravity of 1.0 g/cm$^3$ or more and more preferably formed of a compound material or a composite material having specific gravity of 1.5 g/cm$^3$ to 23 g/cm$^3$.

Further, since the capability of attenuating light energy generally increases as scattering and/or absorption of light increases, the substrate of the biochemical analysis unit preferably has absorbance of 0.3 per cm (thickness) or more and more preferably has absorbance of 1 per cm (thickness) or more. The absorbance can be determined by placing an integrating sphere immediately behind a plate-like member having a thickness of T cm, measuring an amount A of transmitted light at a wavelength of probe light or emission light used for measurement by a spectrophotometer, and calculating A/T. In the present invention, a light scattering substance or a light absorbing substance may be added to the substrate of the biochemical analysis unit in order to improve the capability of attenuating light energy. Particles of a material different from a material forming the substrate of the biochemical analysis unit may be preferably used as a light scattering substance and a pigment or dye may be preferably used as a light absorbing substance.

In another preferred aspect of the present invention, the biochemical analysis unit includes an absorptive substrate containing an absorptive material and the plurality of absorptive regions are formed by causing different positions of the absorptive substrate to contain receptors or ligands.

In the present invention, a porous material or a fiber material may be preferably used as the absorptive material for forming the absorptive regions or the absorptive substrate of the biochemical analysis unit. The absorptive regions or the absorptive substrate of the biochemical analysis unit may be formed by combining a porous material and a fiber material.

In the present invention, a porous material for forming the absorptive regions or the absorptive substrate of the biochemical analysis unit may be any type of an organic material or an inorganic material and may be an organic/inorganic composite material.

In the present invention, an organic porous material used for forming the absorptive regions or the absorptive substrate of the biochemical analysis unit is not particularly limited but a carbon porous material such as an activated carbon or a porous material capable of forming a membrane filter is preferably used. Illustrative examples of porous materials capable of forming a membrane filter include nylons such as nylon-6, nylon-6,6, nylon-4,10; cellulose derivatives such as nitrocellulose, acetyl cellulose, butyric-acetyl cellulose; collagen; alginic acids such as alginic acid, calcium alginate, alginic acid/poly-L-lysine polyionic complex; polyolefins such as polyethylene, polypropylene; polyvinyl chloride; polyvinylidene chloride; polyfluoride such as polyvinylidene fluoride, polytetrafluoride; and copolymers or composite materials thereof.

In the present invention, an inorganic porous material used for forming the absorptive regions or the absorptive substrate of the biochemical analysis unit is not particularly limited. Illustrative examples of inorganic porous materials preferably usable in the present invention include metals such as platinum, gold, iron, silver, nickel, aluminum and the like; metal oxides such as alumina, silica, titania, zeolite and the like; metal salts such as hydroxy apatite, calcium sulfate and the like; and composite materials thereof.

In the present invention, a fiber material used for forming the absorptive regions or the absorptive substrate of the biochemical analysis unit is not particularly limited. Illustrative examples of fiber materials preferably usable in the present invention include nylons such as nylon-6, nylon-6,6, nylon-4,10; and cellulose derivatives such as nitrocellulose, acetyl cellulose, butyric-acetyl cellulose.

In the present invention, the absorptive regions of the biochemical analysis unit may be formed using an oxidization process such as an electrolytic process, a plasma process, an arc discharge process or the like; a primer process using a silane coupling agent, titanium coupling agent or the like; and a surface-active agent process or the like.

The above and other objects and features of the present invention will become apparent from the following description made with reference to the accompanying drawings.

DESCRIPTION OF THE PREFERRED EMBODIMENTS

Figure 1:
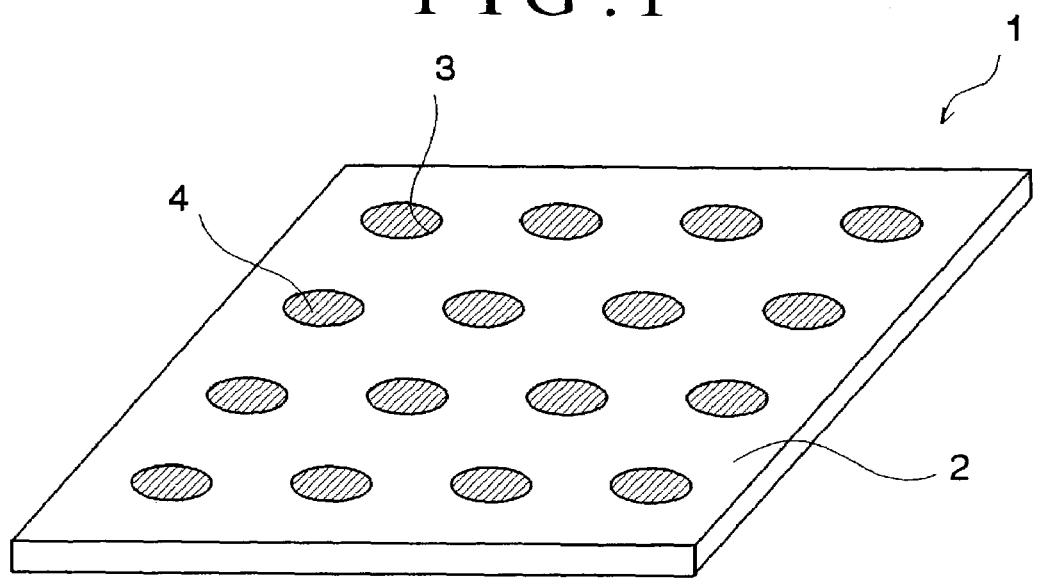
FIG. 1 is a schematic perspective view showing a biochemical analysis unit used in a method for conducting a receptor-ligand association reaction which is a preferred embodiment of the present invention.

FIG. 1 is a schematic perspective view showing a biochemical analysis unit used in a method for conducting a receptor-ligand association reaction which is a preferred embodiment of the present invention.

As shown in FIG. 1, a biochemical analysis unit 1 includes a substrate 2 made of aluminum and formed with a number of substantially circular through-holes 3 at a high density and a number of dot-like absorptive regions 4 are formed by charging nylon-6 in a number of the through-holes 3.

Although not accurately shown in FIG. 1, in this embodiment, the through-holes 3 are formed in the substrate 2 so that substantially circular absorptive regions 4 having a size of about 0.07 mm² are regularly formed in the manner of a matrix of 120 columns×160 lines and, therefore, 19,200 absorptive regions 4 are formed. A number of absorptive regions 4 are formed by charging absorptive material 4 in the through-holes 3 formed in the substrate in such a manner that the surfaces of the absorptive regions 4 are located at the same height level as that of the substrate.

When biochemical analysis is to be performed, a solution containing specific binding substances such as a plurality of cDNAs whose sequences are known but differ from each other are spotted using a spotting device onto a number of the absorptive regions 4 of the biochemical analysis unit 1 and the specific binding substances are fixed therein.

Figure 2:
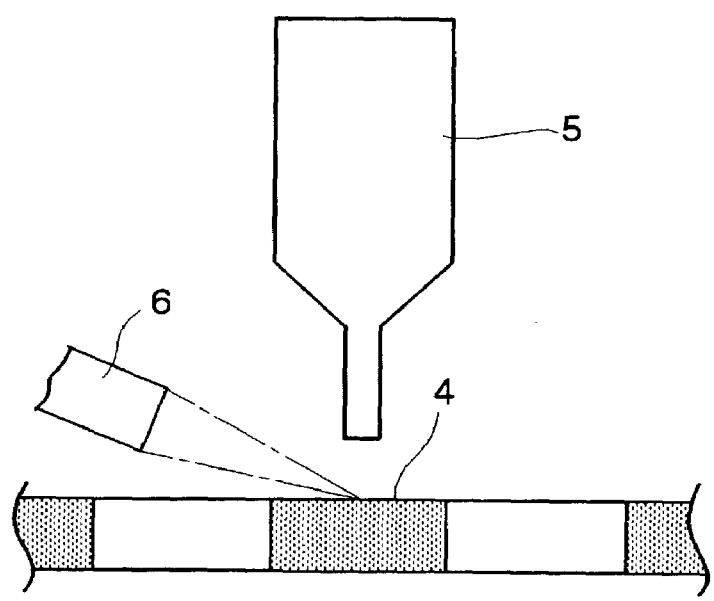
FIG. 2 is a schematic front view showing a spotting device.

FIG. 2 is a schematic front view showing a spotting device.

As shown in FIG. 2, the spotting device includes an injector 5 for ejecting a solution of specific binding substances toward the biochemical analysis unit 1 and a CCD camera 6 and is constituted so that the solution of specific binding substances such as cDNAs are spotted from the injector 5 when the tip end portion of the injector 5 and the center of the absorptive region 4 into which the solution containing specific binding substances is to be spotted are determined to coincide with each other as a result of viewing them using the CCD camera 6, thereby ensuring that the solution of specific binding substances can be accurately spotted into a number of the absorptive regions 4 of the biochemical analysis unit 1.

A substance derived from a living organism and labeled with a labeling substance is then hybridized with the specific binding substances absorbed in a number of the absorptive regions 4 formed in the substrate 2 of the biochemical analysis unit 1.

Figure 3:
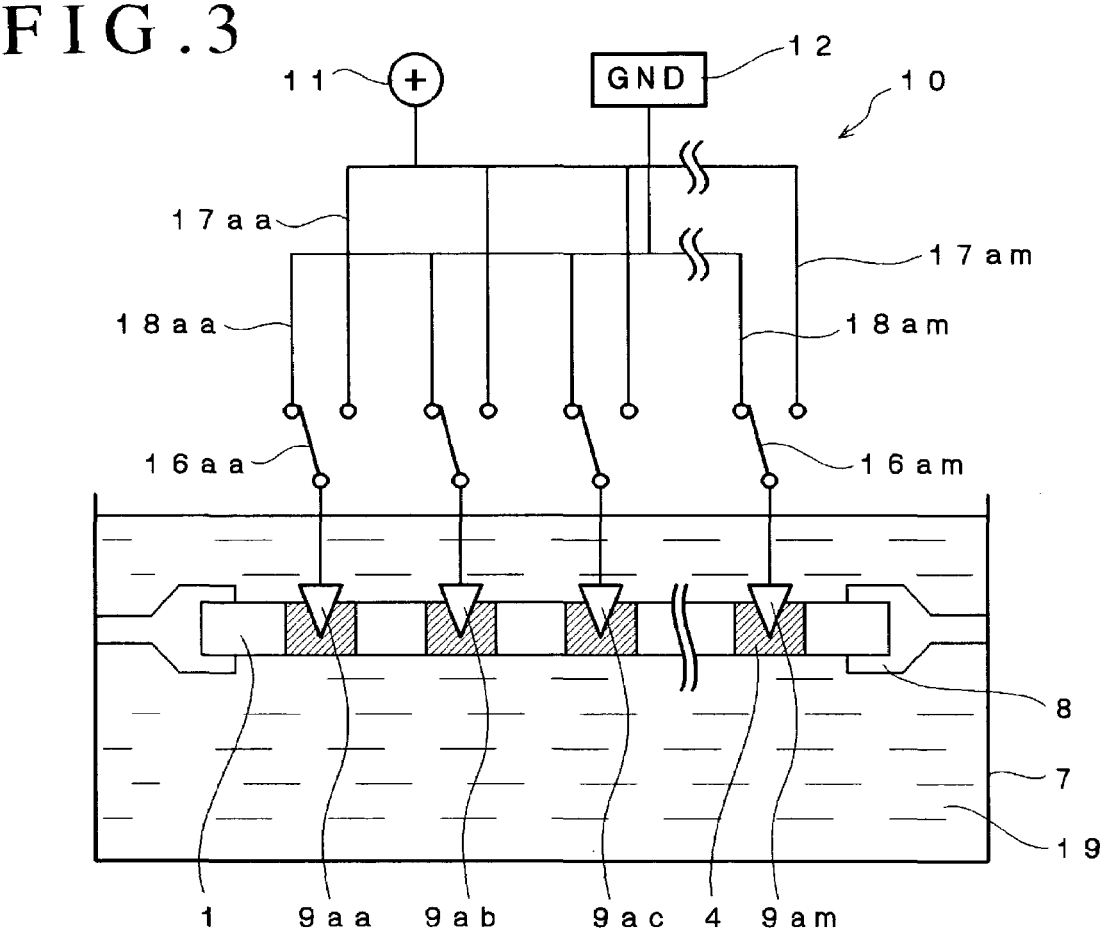
FIG. 3 is a schematic longitudinal cross sectional view showing an apparatus for conducting a receptor-ligand association reaction which is a preferred embodiment of the present invention.

FIG. 3 is a schematic longitudinal cross sectional view showing an apparatus for conducting a receptor-ligand association reaction which is a preferred embodiment of the present invention.

As shown in FIG. 3, the apparatus conducting for a receptor-ligand association reaction according to this embodiment includes a reaction vessel 7 for accommodating a reaction solution 19 and a biochemical analysis unit holding section 8 is formed in the reaction vessel 7 for holding the biochemical analysis unit 1.

As shown in FIG. 3, the apparatus for conducting a receptor-ligand association reaction according to this embodiment further includes an electric field generating device 10.

Figure 4:
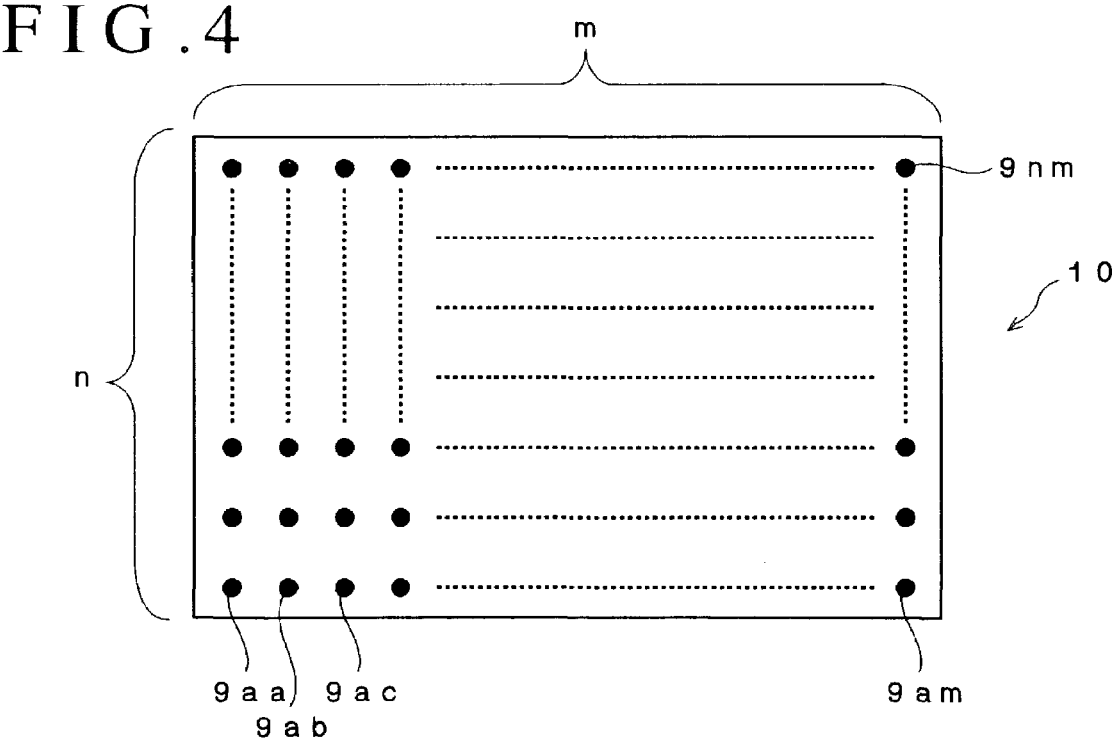
FIG. 4 is a schematic bottom view showing an electric field generating device.

FIG. 4 is a schematic bottom view of the electric field generating device 10.

As shown in FIG. 4, the electric field generating device 10 includes m×n electrodes 9aa, 9ab, 9ac, . . . , 9am, . . . , 9nm (nm=m×n) and, as shown in FIG. 3, a positive power source 11 and a ground terminal 12.

Although not accurately shown in FIGS. 3 and 4, the electric field generating device 10 includes the m×n electrodes 9aa, 9ab, 9ac, . . . , 9am, . . . , 9nm at positions corresponding to those of the absorptive regions 4 formed in the substrate 2 of the biochemical analysis unit 1 and, therefore, since the absorptive regions 4 are formed in the biochemical analysis unit 1 in the manner of a matrix of 120 columns×160 lines in this embodiment, m equals to 120 and n equals to 160 and the electric field generating device 10 includes the 19,200 electrodes 9aa, 9ab, 9ac, . . . , 9am, . . . , 9nm.

The electric field generating device 10 can be moved by a motor (not shown) between an electric field applying position where each of the electrodes 9aa, 9ab, 9ac, . . . , 9am, . . . , 9nm is inserted into one of the absorptive regions 4 formed in the biochemical analysis unit 1 as shown in FIG. 3 and a retracted position where each of the electrodes 9aa, 9ab, 9ac, . . . , 9am, . . . , 9nm is retracted upward in FIG. 3 from the absorptive regions 4 formed in the biochemical analysis unit 1.

Figure 5:
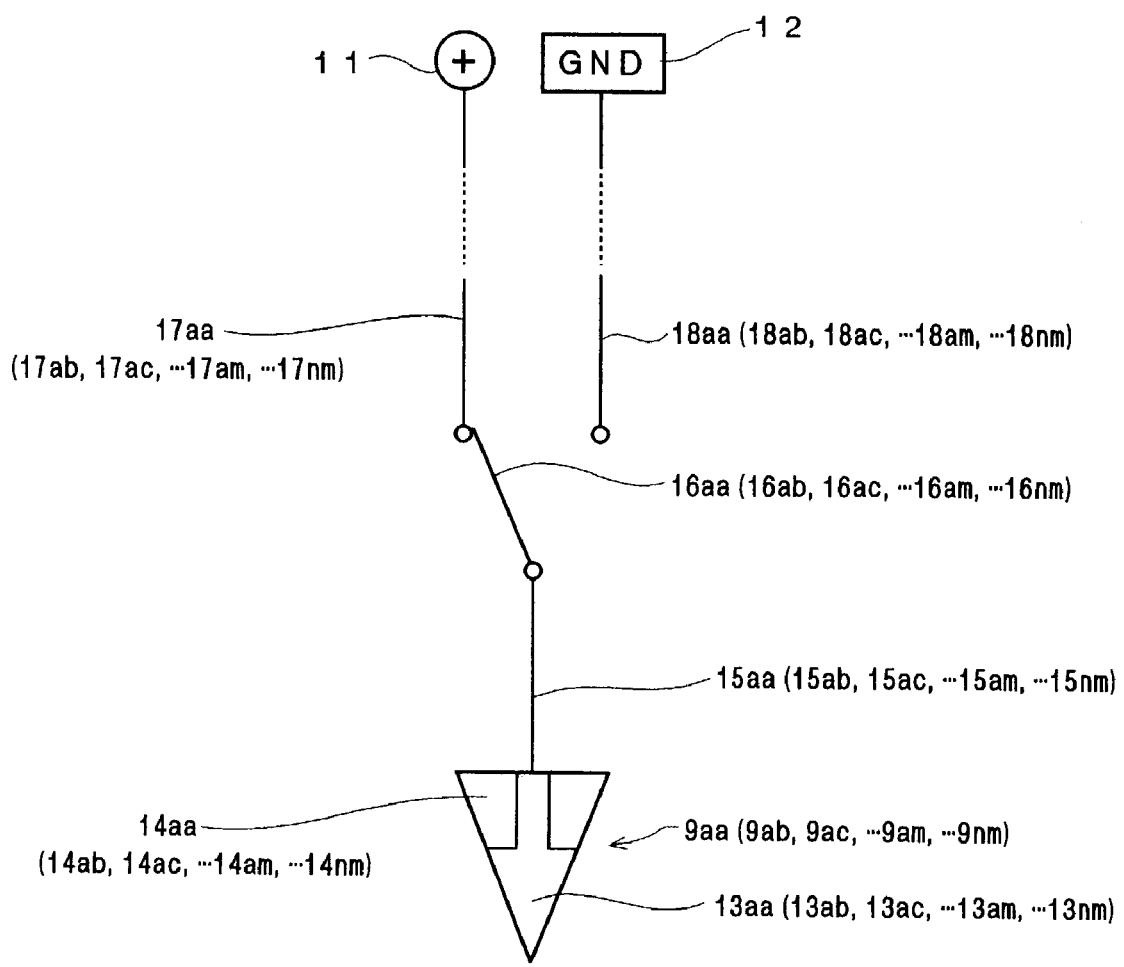
FIG. 5 is a schematic cross-sectional view of a single electrode.

FIG. 5 is a schematic cross-sectional view showing one of the electrodes 9aa, 9ab, 9ac, . . . , 9am, . . . , 9nm.

As shown in FIG. 5, each of the electrodes 9aa, 9ab, 9ac, . . . , 9am, . . . , 9nm has a cone-like shape and is constituted by a conductive material 13*aa*, 13*ab*, 13*ac*, . . . , 13*am*, . . . , 13*nm* and an insulating material 14*aa*, 14*ab*, 14*ac*, . . . , 14*am*, . . . , 14*nm* for covering a portion other than a tip end portion of each the conductive material 13*aa*, 13*ab*, 13*ac*, . . . , 13*am*, . . . , 13*nm*. An electric conductor 15*aa*, 15*ab*, 15*ac*, . . . , 15*am*, . . . , 15*nm* is connected to the conductive material 13*aa*, 13*ab*, 13*ac*, . . . , 13*am*, . . . , 13*nm* of each of the electrodes 9*aa*, 9*ab*, 9*ac*, . . . , 9*am*, . . . , 9*nm*.

As shown in FIGS. 3 and 5, a switch 16*aa*, 16*ab*, 16*ac*, . . . , 16*am*, . . . , 16*nm* is connected to the electric conductor 15*aa*, 15*ab*, 15*ac*, . . . , 15*am*, . . . , 15*nm* connected to each of the electrodes 9*aa*, 9*ab*, 9*ac*, . . . , 9*am*, . . . , 9*nm* so that each of the electrodes 9*aa*, 9*ab*, 9*ac*, . . . , 9*am*, . . . , 9*nm* can be selectively connected either to one of electric conductors 17*aa*, 17*ab*, 17*ac*, . . . , 17*am*, . . . , 17*nm* connected to the positive power source 11 or to one of electric conductors 18*aa*, 18*ab*, 18*ac*, . . . , 18*am*, . . . , 18*nm* connected to the ground terminal 12 by switching the corresponding switch 16*aa*, 16*ab*, 16*ac*, . . . , 16*am*, . . . , 16*nm*.

Figure 6:
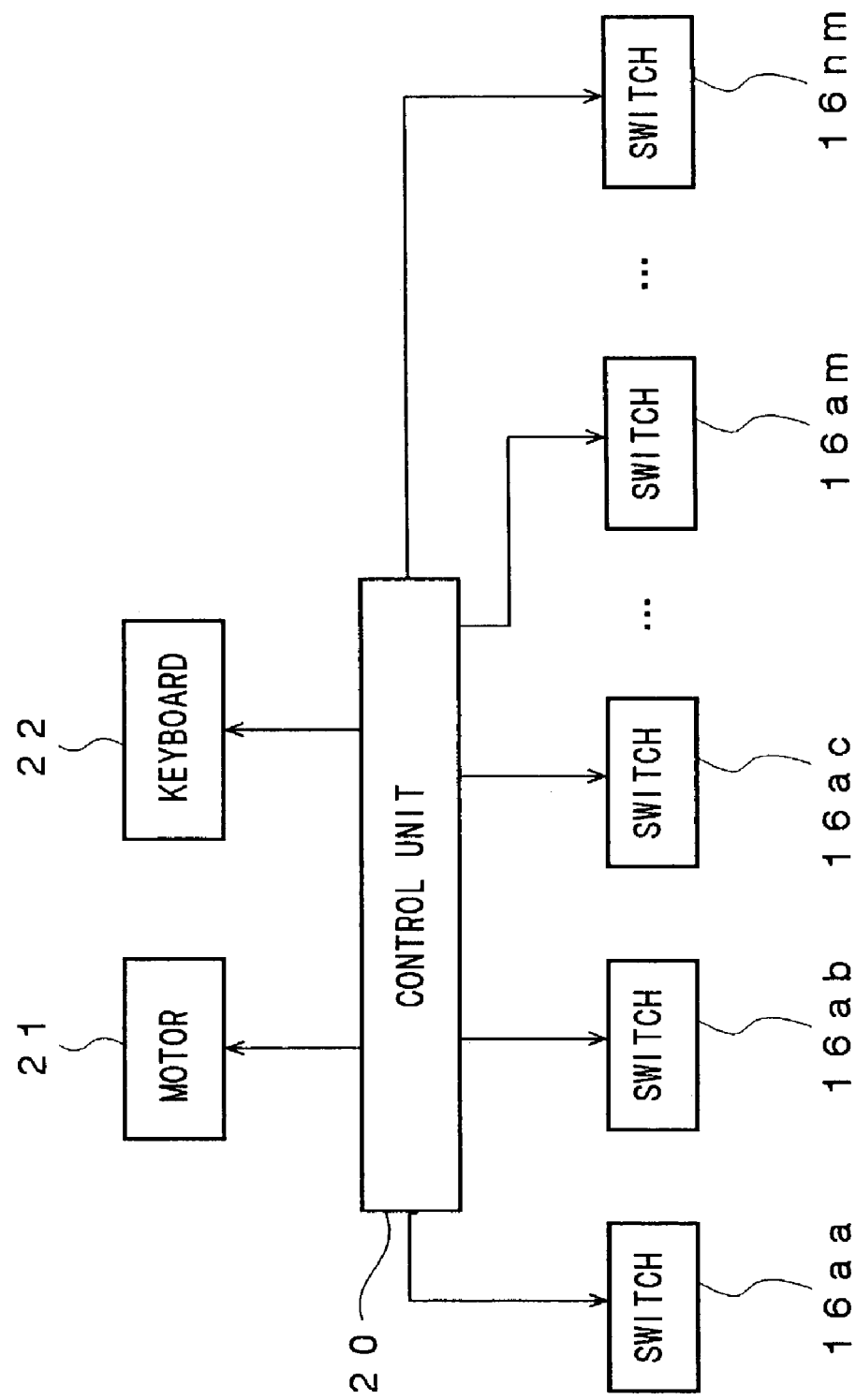
FIG. 6 is a block diagram of a control system, a drive system and an input system of an apparatus for conducting a receptor-ligand association reaction which is a preferred embodiment of the present invention.

FIG. 6 is a block diagram of a control system, a drive system and an input system of the apparatus for conducting a receptor-ligand association reaction according to this embodiment.

As shown in FIG. 6, the control system of the apparatus for conducting a receptor-ligand association reaction according to this embodiment includes a control unit 20 for controlling the overall operation of the apparatus for conducting a receptor-ligand association reaction. The control unit 20 is constituted so as to on and off control the positive power source 11 and control the switching operation of the switches 16*aa*, 16*ab*, 16*ac*, . . . , 16*am*, . . . , 16*nm*.

As shown in FIG. 6, the drive system of the apparatus for conducting a receptor-ligand association reaction according to this embodiment includes a motor 21 for moving the electric field generating device 10 between the electric field applying position and the retracted position.

As shown in FIG. 6, the input system of the apparatus for conducting a receptor-ligand association reaction according to this embodiment includes a keyboard 22.

In the thus constituted apparatus for conducting receptor-ligand association according to this embodiment, a substance derived from a living organism and labeled with a labeling substance is selectively hybridized with specific binding substances absorbed in a number of the absorptive regions 4 of the biochemical analysis unit 1 in the following manner.

While the electric field generating device 10 is held at the retracted position, the biochemical analysis unit 1 formed with a number of the absorptive regions 4 in which specific binding substances are absorbed is first set at the biochemical analysis unit holding section 8.

A reaction solution 19 is then prepared and accommodated in the reaction vessel 7.

In the case where a specific binding substance such as cDNA is to be labeled with a radioactive labeling substance, a reaction solution 19 containing a substance derived from a living organism and labeled with a radioactive labeling substance as a probe is prepared and is accommodated in the reaction vessel 7.

On the other hand, in the case where a specific binding substance such as cDNA is to be labeled with a labeling substance which generates chemiluminescence emission when it contacts a chemiluminescent substrate, a reaction solution 19 containing a substance derived from a living organism and labeled with a hapten such as digoxigenin as a probe is prepared and is accommodated in the reaction vessel 7.

Further, in the case where a specific binding substance such as cDNA is to be labeled with a fluorescent substance, a reaction solution 19 containing a substance derived from a living organism and labeled with a fluorescent substance as a probe is prepared and is accommodated in the reaction vessel 7.

It is possible to prepare a reaction solution 19 containing two or more substances derived from a living organism among a substance derived from a living organism and labeled with a radioactive labeling substance, a substance derived from a living organism and labeled with a hapten such as digoxigenin and a substance derived from a living organism and labeled with a fluorescent substance such as a fluorescent dye and accommodate it in the reaction vessel 7. In this embodiment, a reaction solution 19 containing a substance derived from a living organism and labeled with a radioactive labeling substance, a substance derived from a living organism and labeled with a hapten such as digoxigenin and a substance derived from a living organism and labeled with a fluorescent substance such as a fluorescent dye is prepared and accommodated in the reaction vessel 7.

When the reaction solution 19 is prepared and accommodated in the reaction vessel 7, a start signal is input by a user through the keyboard 22.

The start signal is output to the control unit 20 and when the control unit 20 receives the start signal, it outputs a drive signal to the motor 21, thereby causing it to move the electric field generating device 10 from the retracted position to the electric field applying position.

As a result, the cone-like electrodes 9*aa*, 9*ab*, 9*ac*, . . . , 9*am*, . . . , 9*nm* formed in the electric field generating device 10 at positions corresponding to a number of the absorptive regions 4 of the biochemical analysis unit 1 are inserted into the corresponding absorptive regions 4 of the biochemical analysis unit 1.

The control unit 20 then switches the switch 16*aa* connected to the electrode 9*aa* so that the electric conductor 15*aa* is connected to the electric conductor 17*aa* connected to the positive power source 11, thereby connecting the electrode 9*aa* to the positive power source 11 and switches the switches 16*ab*, 16*ac*, . . . , 16*am*, . . . , 16*nm* connected to the electrodes 9*ab*, 9*ac*, . . . , 9*am*, . . . , 9*nm* so that the electric conductors 15*ab*, 15*ac*, . . . , 15*am*, . . . , 15*nm* are connected to the electric conductors 18*ab*, 18*ac*, . . . , 18*am*, . . . , 18*nm* connected to the ground terminal 12, thereby connecting the electrodes 9*ab*, 9*ac*, . . . , 9*am*, . . . , 9*nm*, i.e., the electrodes other than the electrode 9*aa*, to the ground terminal 12.

When the switches 16*aa*, 16*ab*, 16*ac*, . . . , 16*am*, . . . , 16*nm* have been switched, thereby connecting the electrode 9*aa* to the positive power source 11 and connecting the electrodes 9*ab*, 9*ac*, . . . , 9*am*, . . . , 9*nm* to the ground terminal 12, the control unit 20 turns the positive power source 11 on.

As a result, a positive voltage is applied to the electrode 9*aa* and an electric field is generated by the electrode 9*aa* so that a substance derived from a living organism and contained in the reaction solution 19 is attracted to the electrode 9*aa*.

Since the electric field generating device 10 has been moved to the electric field applying position and the electrode 9*aa* is inserted into the corresponding absorptive region 4 of the biochemical analysis unit 1, a substance derived from a living organism and contained in the reaction solution 19 is forcibly brought into contact with a specific binding substance absorbed in the absorptive region 4 of the biochemical analysis unit 1 into which the electrode 9aa is inserted and selectively hybridized with the specific binding substance.

Therefore, it is possible to markedly improve the efficiency of hybridization and since it is possible to markedly increase the possibility of association of the substance derived from a living organism and contained in the reaction solution 19 with the specific binding substance as a target absorbed in the absorptive region 4 of the biochemical analysis unit 1 into which the electrode 9aa is inserted, it is possible to selectively hybridize the substance derived from a living organism and contained in the reaction solution 19 with the specific binding substance absorbed in the absorptive region 4 of the biochemical analysis unit 1 into which the electrode 9aa is inserted in a desired manner.

When a predetermined time period has passed, the control unit 20 turns the positive power source 11 off.

As a result, a substance derived from a living organism which was attracted to the absorptive region 4 of the biochemical analysis unit 1 into which the electrode 9aa is inserted but was nevertheless not hybridized with a specific binding substance absorbed in the absorptive region 4 leaves the absorptive region 4 and is returned to the reaction solution 19 The control unit 20 then switches the switch 16ab connected to the electrode 9ab so that the electric conductor 15ab is connected to the electric conductor 17ab connected to the positive power source 11, thereby connecting the electrode 9ab to the positive power source 11 and switches the switch 16aa connected to the electrode 9aa so that the electric conductor 15aa is connected to the electric conductor 18aa connected to the ground terminal 12, thereby connecting the electrodes 9aa, 9ac, . . . , 9am, . . . , 9nm, i.e., the electrodes other than the electrode 9ab, to the ground terminal 12.

When the switches 16aa and 16ab have been switched, thereby connecting the electrode 9ab to the positive power source 11 and connecting the electrodes 9aa, 9ac, . . . , 9am, . . . , 9nm to the ground terminal 12, the control unit 20 turns the positive power source 11 on.

As a result, a positive voltage is applied to the electrode 9ab and an electric field is generated by the electrode 9ab so that a substance derived from a living organism and contained in the reaction solution 19 is attracted to the electrode 9ab. As a consequence, a substance derived from a living organism and contained in the reaction solution 19 is forcibly brought into contact with a specific binding substance absorbed in the absorptive region 4 of the biochemical analysis unit 1 into which the electrode 9ab is inserted and selectively hybridized with the specific binding substance.

Therefore, it is possible to markedly improve the efficiency of hybridization and since it is possible to markedly increase the possibility of association of the substance derived from a living organism and contained in the reaction solution 19 with the specific binding substance as a target absorbed in the absorptive region 4 of the biochemical analysis unit 1, it is possible to selectively hybridize the substance derived from a living organism and contained in the reaction solution 19 with the specific binding substance absorbed in the absorptive region 4 of the biochemical analysis unit 1 into which the electrode 9ab is inserted in a desired manner.

When a predetermined time period has passed, the control unit 20 turns the positive power source 11 off.

As a result, a substance derived from a living organism which was attracted to the absorptive region 4 of the biochemical analysis unit 1 into which the electrode 9ab is inserted but was nevertheless not hybridized with a specific binding substance absorbed in the absorptive region 4 leaves the absorptive region 4 and is returned to the reaction solution 19.

The control unit 20 then switches the switch 16ac connected to the electrode 9ac so that the electric conductor 15ac is connected to the electric conductor 17ac connected to the positive power source 11, thereby connecting the electrode 9ac to the positive power source 11 and switches the switch 16ab connected to the electrode 9ab so that the electric conductor 15ab is connected to the electric conductor 18ab connected to the ground terminal 12, thereby connecting the electrodes 9aa, 9ab, . . . , 9am, . . . , 9nm, i.e., the electrodes other than the electrode 9ab, to the ground terminal 12.

When the switches 16ab and 16ac have been switched, thereby connecting the electrode 9ac to the positive power source 11 and connecting the electrodes 9aa, 9ab, . . . , 9am, . . . , 9nm to the ground terminal 12, the control unit 20 turns the positive power source 11 on.

As a result, a positive voltage is applied to the electrode 9ac and an electric field is generated by the electrode 9ac so that a substance derived from a living organism and contained in the reaction solution 19 is attracted to the electrode 9ac. As a consequence, a substance derived from a living organism and contained in the reaction solution 19 is forcibly brought into contact with a specific binding substance absorbed in the absorptive region 4 of the biochemical analysis unit 1 into which the electrode 9ac is inserted and selectively hybridized with the specific binding substance.

Similarly to the above, the control unit 20 controls the switching operation of the switches 16aa, 16ab, 16ac, . . . , 16am, . . . , 16nm so that an electrode 9jk, namely a successive one of the electrodes 9aa, 9ab, 9ac, . . . , 9am, . . . , 9nm provided in the electric field generating device 10, is sequentially connected to the positive power source 11 wherein j=a, . . . , n and k=a, . . . , m and that other electrodes 9aa, 9ab, 9ac, . . . , 9(j−1)k, 9(j+1)k, . . . , 9am, . . . , 9nm are connected to the ground terminal 12 and controls the positive power source to cause it to apply a positive voltage to the electrode 9jk, thereby generating an electric field.

As a result, a substance derived from a living organism and contained in the reaction solution 19 is sequentially attracted to the electrode 9jk so that a substance derived from a living organism and contained in the reaction solution 19 is forcibly brought into contact with a specific binding substance absorbed in the absorptive region 4 of the biochemical analysis unit 1 into which the electrode 9jk is inserted and that the substance derived from a living organism and contained in the reaction solution 19 and the specific binding substance are selectively hybridized with each other.

In this manner, according to this embodiment, the switching operation of the switches 16aa, 16ab, 16ac, . . . , 16am, . . . , 16nm is controlled so that the electrodes 9aa, 9ab, 9ac, . . . , 9am, . . . , 9nm provided in the electric field generating device 10 are sequentially connected to the positive power source 11 one at a time and that other electrodes are connected to the ground terminal 12 and a positive voltage is applied to only one of the electrodes 9aa, 9ab, 9ac, . . . , 9am, . . . , 9nm from the positive power source 11. As a result, a substance derived from a living organism and contained in the reaction solution 19 is selectively attracted to only the electrode applied with a positive voltage so that the substance derived from a living organism and contained in the reaction solution 19 is forcibly brought into contact with a specific binding substance absorbed in the absorptive region 4 of the biochemical analysis unit 1 into which the electrode applied with a positive voltage is inserted, whereby the substance derived from a living organism and the specific binding substance are selectively hybridized with each other. Therefore, it is possible to markedly improve the efficiency of hybridization and since it is possible to markedly increase the possibility of association of a substance derived from a living organism and contained in the reaction solution 19 with a specific binding substance as a target absorbed in the absorptive region 4 of the biochemical analysis unit 1 into which an electrode applied with a positive voltage is inserted, it is possible to selectively hybridize the substance derived from a living organism and contained in the reaction solution 19 with the specific binding substance absorbed in the absorptive region 4 of the biochemical analysis unit 1 into which the electrode applied with a positive voltage is inserted in a desired manner.

Moreover, according to this embodiment, since a positive voltage is sequentially applied from the positive power source 11 to one of the electrodes 9aa, 9ab, 9ac, . . . , 9am, . . . , 9nm and the positive power source 11 is turned off when a predetermined time period has passed, a substance derived from a living organism which was attracted to the absorptive region 4 of the biochemical analysis unit 1 into which the electrode applied with a positive voltage is inserted but was nevertheless not hybridized with a specific binding substance absorbed in the absorptive region 4 leaves the absorptive region 4 to be returned to the reaction solution 19 when the positive power source 11 is turned off and is attracted to an electrode next applied with a positive voltage from the positive power source 11. Therefore, since the substance derived from a living organism is moved in the reaction solution 19 in response to the on and off operation of the positive power source 11 similarly to the case where the reaction solution 19 is agitated, it is possible to markedly increase the possibility of association of the substance derived from a living organism and contained in the reaction solution 19 with specific binding substances as a target contained in a number of the absorptive regions 4 of the biochemical analysis unit 1.

When a positive voltage has been applied to all of the electrodes 9aa, 9ab, 9ac, . . . , 9am, . . . , 9nm inserted into the corresponding absorptive regions 4 formed in the substrate 2 of the biochemical analysis unit 1 and hybridization has been completed, the control unit 20 outputs a drive signal to the motor 21, thereby causing it to move the electric field generating device 10 from the electric field applying position to the retracted position.

In this manner, radiation data of a radioactive labeling substance and a fluorescence data of a fluorescent substance such as a fluorescent dye are recorded in a number of the absorptive regions 4 formed in the substrate 2 of the biochemical analysis unit 1.

The fluorescence data recorded in a number of the absorptive regions 4 of the biochemical analysis unit 1 are read by a scanner described later and biochemical analysis data are produced. On the other hand, radiation data recorded in a number of the absorptive regions 4 of the biochemical analysis unit 1 are transferred onto a stimulable phosphor sheet described later and read by a scanner described later, thereby producing biochemical analysis data.

To the contrary, in order to record chemiluminescence data in a number of the absorptive regions 4 formed in the substrate 2 of the biochemical analysis unit 1, a reaction solution 19 containing an antibody to the hapten such as digoxigenin labeled with an enzyme which generates chemiluminescence emission when it contacts a chemiluminescent substrate is further prepared and accommodated in the reaction vessel 7 and the antibody to the hapten such as digoxigenin labeled with an enzyme which generates chemiluminescence emission when it contacts a chemiluminescent substrate is bound with the hapten such as digoxigenin labeling a substance derived from a living organism selectively hybridized with specific binding substances absorbed in a number of the absorptive regions 4 formed in the substrate 2 of the biochemical analysis unit 1 by the an antigen-antibody reaction.

Specifically, a reaction solution 19 containing an antibody to the hapten such as digoxigenin labeled with an enzyme which generates chemiluminescence emission when it contacts a chemiluminescent substrate is first prepared and accommodated in the reaction vessel 7.

When the reaction solution 19 is prepared and accommodated in the reaction vessel 7, a start signal is input by a user through the keyboard 22.

The start signal is output to the control unit 20 and when the control unit 20 receives the start signal, it outputs a drive signal to the motor 21, thereby causing it to move the electric field generating device 10 from the retracted position to the electric field applying position.

As a result, the cone-like electrodes 9aa, 9ab, 9ac, . . . , 9am, . . . , 9nm formed in the electric field generating device 10 at positions corresponding to a number of the absorptive regions 4 of the biochemical analysis unit 1 are inserted into the corresponding absorptive regions 4 of the biochemical analysis unit 1.

The control unit 20 then switches the switch 16aa connected to the electrode 9aa so that the electric conductor 15aa is connected to the electric conductor 17aa connected to the positive power source 11, thereby connecting the electrode 9aa to the positive power source 11 and switches the switches 16ab, 16ac, . . . , 16am, . . . , 16nm connected to the electrodes 9ab, 9ac, . . . , 9am, . . . , 9nm so that the electric conductors 15ab, 15ac, . . . , 15am, . . . , 15nm are connected to the electric conductors 18ab, 18ac, . . . , 18am, . . . , 18nm connected to the ground terminal 12, thereby connecting the electrodes 9ab, 9ac, . . . , 9am, . . . , 9nm, i.e., the electrodes other than the electrode 9aa, to the ground terminal 12.

When the switches 16aa, 16ab, 16ac, . . . , 16am, . . . , 16nm have been switched, thereby connecting the electrode 9aa to the positive power source 11 and connecting the electrodes 9ab, 9ac, . . . , 9am, . . . , 9nm to the ground terminal 12, the control unit 20 turns the positive power source 11 on.

As a result, a positive voltage is applied to the electrode 9aa and an electric field is generated by the electrode 9aa so that an antibody to the hapten labeled with an enzyme which generates chemiluminescence emission when it contacts a chemiluminescent substrate and contained in the reaction solution 19 is attracted to the electrode 9aa.

Since the electric field generating device 10 has been moved to the electric field applying position and the electrode 9aa is inserted into the corresponding absorptive region 4 of the biochemical analysis unit 1, an antibody to the hapten labeled with an enzyme which generates chemiluminescence emission when it contacts a chemiluminescent substrate and contained in the reaction solution 19 is forcibly brought into contact with a hapten labeling a substance derived from a living organism and selectively hybridized with a specific biding substance absorbed in the absorptive region 4 of the biochemical analysis unit 1 and bound with the hapten by an antigen-antibody reaction.

Therefore, it is possible to markedly improve the efficiency of a receptor-ligand association reaction and since it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with a specific biding substance absorbed in the absorptive region 4 of the biochemical analysis unit 1 into which the electrode 9aa is inserted, it is possible to bind an antibody to the hapten labeled with an enzyme which generates chemiluminescence emission when it contacts a chemiluminescent substrate and contained in the reaction solution 19 with a hapten labeling a substance derived from a living organism and selectively hybridized with a specific biding substance absorbed in the absorptive region 4 of the biochemical analysis unit 1 into which the electrode 9aa is inserted in a desired manner.

When a predetermined time period has passed, the control unit 20 turns the positive power source 11 off.

As a result, an antibody to the hapten labeled with an enzyme which generates chemiluminescence emission when it contacts a chemiluminescent substrate which was attracted to the absorptive region 4 of the biochemical analysis unit 1 into which the electrode 9aa is inserted but nevertheless did not bind with a hapten labeling a substance derived from a living organism and selectively hybridized with a specific binding substance absorbed in the absorptive region 4 leaves the absorptive region 4 and is returned to the reaction solution 19.

The control unit 20 then switches the switch 16ab connected to the electrode 9ab so that the electric conductor 15ab is connected to the electric conductor 17ab connected to the positive power source 11, thereby connecting the electrode 9ab to the positive power source 11 and switches the switch 16aa connected to the electrode 9aa so that the electric conductor 15aa is connected to the electric conductor 18aa connected to the ground terminal 12, thereby connecting the electrodes 9aa, 9ac, . . . , 9am, . . . , 9nm, i.e., the electrodes other than the electrode 9ab, to the ground terminal 12.

When the switches 16aa and 16ab have been switched, thereby connecting the electrode 9ab to the positive power source 11 and connecting the electrodes 9aa, 9ac, . . . , 9am, . . . , 9nm to the ground terminal 12, the control unit 20 turns the positive power source 11 on.

As a result, a positive voltage is applied to the electrode 9ab and an electric field is generated by the electrode 9ab so that an antibody to the hapten labeled with an enzyme which generates chemiluminescence emission when it contacts a chemiluminescent substrate and contained in the reaction solution 19 is attracted to the electrode 9ab. As a consequence, an antibody to the hapten labeled with an enzyme which generates chemiluminescence emission when it contacts a chemiluminescent substrate and contained in the reaction solution 19 is forcibly brought into contact with a hapten labeling a substance derived from a living organism and selectively hybridized with a specific biding substance absorbed in the absorptive region 4 of the biochemical analysis unit 1 and bound with the hapten by an antigen-antibody reaction.

Therefore, it is possible to markedly improve the efficiency of a receptor-ligand association reaction and since it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with a specific biding substance absorbed in the absorptive region 4 of the biochemical analysis unit 1 into which the electrode 9ab is inserted, it is possible to bind an antibody to the hapten labeled with an enzyme which generates chemiluminescence emission when it contacts a chemiluminescent substrate and contained in the reaction solution 19 with a hapten labeling a substance derived from a living organism and selectively hybridized with a specific biding substance absorbed in the absorptive region 4 of the biochemical analysis unit 1 into which the electrode 9ab is inserted by an antigen-antibody reaction in a desired manner.

When a predetermined time period has passed, the control unit 20 turns the positive power source 11 off.

As a result, an antibody to the hapten labeled with an enzyme which generates chemiluminescence emission when it contacts a chemiluminescent substrate which was attracted to the absorptive region 4 of the biochemical analysis unit 1 into which the electrode 9aa is inserted but nevertheless did not bind with a hapten labeling a substance derived from a living organism and selectively hybridized with a specific binding substance absorbed in the absorptive region 4 leaves the absorptive region 4 and is returned to the reaction solution 19.

The control unit 20 then switches the switch 16ac connected to the electrode 9ac so that the electric conductor 15ac is connected to the electric conductor 17ac connected to the positive power source 11, thereby connecting the electrode 9ac to the positive power source 11 and switches the switch 16ab connected to the electrode 9ab so that the electric conductor 15ab is connected to the electric conductor 18ab connected to the ground terminal 12, thereby connecting the electrodes 9aa, 9ab, . . . , 9am, . . . , 9nm, i.e., the electrodes other than the electrode 9ac, to the ground terminal 12.

When the switches 16ab and 16ac have been switched, thereby connecting the electrode 9ac to the positive power source 11 and connecting the electrodes 9aa, . . . , 9ab, . . . , 9am, . . . , 9nm to the ground terminal 12, the control unit 20 turns the positive power source 11 on.

As a result, a positive voltage is applied to the electrode 9ac and an electric field is generated by the electrode 9ac so that an antibody to the hapten labeled with an enzyme which generates chemiluminescence emission when it contacts a chemiluminescent substrate and contained in the reaction solution 19 is attracted to the electrode 9ac. As a consequence, an antibody to the hapten labeled with an enzyme which generates chemiluminescence emission when it contacts a chemiluminescent substrate and contained in the reaction solution 19 is forcibly brought into contact with a hapten labeling a substance derived from a living organism and selectively hybridized with a specific biding substance absorbed in the absorptive region 4 of the biochemical analysis unit 1 and bound with the hapten by an antigen-antibody reaction.

Similarly to the above, the control unit 20 controls the switching operation of the switches 16aa, 16ab, 16ac, . . . , 16am, . . . , 16nm so that one electrode 9jk, namely a successive one of the electrodes 9aa, 9ab, 9ac, . . . , 9am, . . . , 9nm provided in the electric field generating device 10, is sequentially connected to the positive power source 11 wherein j=a, . . . , n and k=a, . . . , m and that other electrodes 9*aa*, 9*ab*, 9*ac*, ..., 9(j-1)k, 9(j+1)k, ..., 9*am*, ..., 9*nm* are connected to the ground terminal 12 and controls the positive power source to cause it to apply a positive voltage to the electrode 9*jk*, thereby generating an electric field.

As a result, an antibody to the hapten labeled with an enzyme which generates chemiluminescence emission when it contacts a chemiluminescent substrate and contained in the reaction solution 19 is sequentially attracted to the electrode 9*jk* and is forcibly brought into contact with a hapten labeling a substance derived from a living organism and selectively hybridized with a specific biding substance absorbed in the absorptive region 4 of the biochemical analysis unit 1 to be bound with the hapten by an antigen-antibody reaction.

In this manner, according to this embodiment, the switching operation of the switches 16*aa*, 16*ab*, 16*ac*, ..., 16*am*, ..., 16*nm* is controlled so that the electrodes 9*aa*, 9*ab*, 9*ac*, ..., 9*am*, ..., 9*nm* provided in the electric field generating device 10 are sequentially connected to the positive power source 11 one at a time and that other electrodes are connected to the ground terminal 12 and a positive voltage is applied to only one of the electrodes 9*aa*, 9*ab*, 9*ac*, ..., 9*am*, ..., 9*nm* from the positive power source 11. As a result, an antibody to the hapten labeled with an enzyme which generates chemiluminescence emission when it contacts a chemiluminescent substrate and contained in the reaction solution 19 is selectively attracted to only the electrode applied with a positive voltage and is forcibly brought into contact with a hapten labeling a substance derived from a living organism and selectively hybridized with a specific biding substance absorbed in the absorptive region 4 of the biochemical analysis unit 1 into which the electrode applied with a positive voltage is inserted, thereby being bound with the hapten by an antigen-antibody reaction. Therefore, it is possible to markedly improve the efficiency of an antigen-antibody reaction and since it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with a specific biding substance absorbed in the absorptive region 4 of the biochemical analysis unit 1 into which the electrode applied with a positive voltage is inserted, it is possible to bind an antibody to the hapten labeled with an enzyme which generates chemiluminescence emission when it contacts a chemiluminescent substrate and contained in the reaction solution 19 with a hapten labeling a substance derived from a living organism and selectively hybridized with a specific biding substance absorbed in the absorptive region 4 of the biochemical analysis unit 1 into which the electrode applied with a positive voltage is inserted by an antigen-antibody reaction in a desired manner.

Moreover, according to this embodiment, since a positive voltage is sequentially applied from the positive power source 11 to the electrodes 9*aa*, 9*ab*, 9*ac*, ..., 9*am*, ..., 9*nm* one at a time and the positive power source 11 is turned off when a predetermined time period has passed, an antibody to the hapten labeled with an enzyme which generates chemiluminescence emission when it contacts a chemiluminescent substrate which was attracted to the absorptive region 4 of the biochemical analysis unit 1 into which the electrode applied with a positive voltage is inserted but nevertheless did not bind with a hapten labeling a substance derived from a living organism and selectively hybridized with a specific binding substance absorbed in the absorptive region 4 leaves the absorptive region 4 to be returned to the reaction solution 19 when the positive power source 11 is turned off and is attracted to an electrode next applied with a positive voltage from the positive power source 11. Therefore, since an antibody to the hapten labeled with an enzyme which generates chemiluminescence emission when it contacts a chemiluminescent substrate is moved in the reaction solution 19 in response to the on and off operation of the positive power source 11 similarly to the case where the reaction solution 19 is agitated, it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with a specific biding substance absorbed in the absorptive region 4 of the biochemical analysis unit 1 into which the electrode applied with a positive voltage is inserted.

In this manner, chemiluminescent data are recorded in a number of the absorptive regions 4 formed in the substrate 2 of the biochemical analysis unit 1.

The chemiluminescent data recorded in a number of the absorptive regions 4 formed in the substrate 2 of the biochemical analysis unit 1 are read by a data producing system described later and biochemical analysis data are produced.

Figure 7:
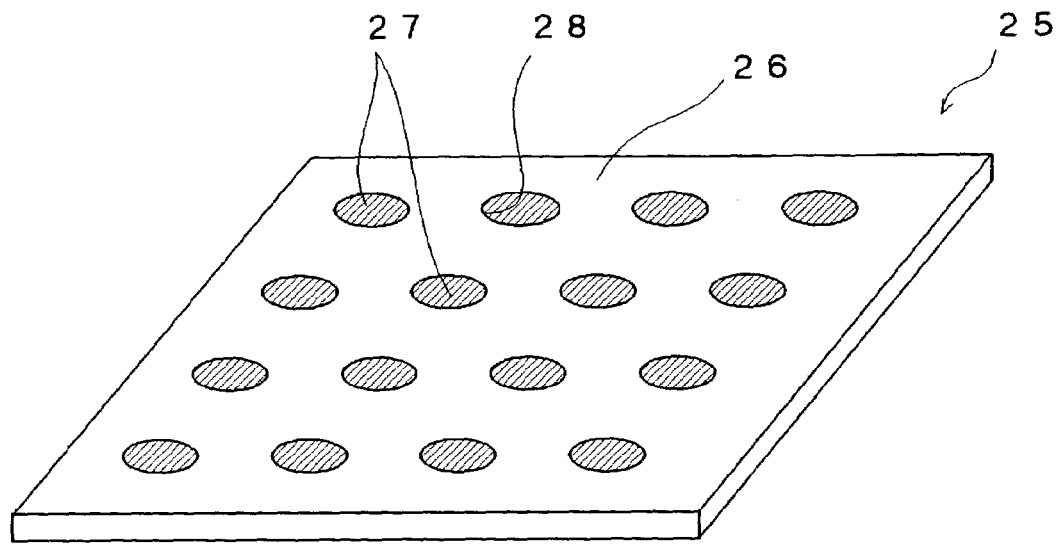
FIG. 7 is a schematic perspective view showing a stimulable phosphor sheet.

FIG. 7 is a schematic perspective view showing a stimulable phosphor sheet.

As shown in FIG. 7, a stimulable phosphor sheet 25 includes a support 26 made of nickel and regularly formed with a number of substantially circular through-holes 28 and a number of stimulable phosphor layer regions 27 are dot-like formed by embedding stimulable phosphor in a number of the through-holes 28 formed in the support 26.

A number of the through-holes 28 are formed in the support 26 in the same pattern as that of a number of the absorptive regions 4 formed in the substrate 2 of the biochemical analysis unit 1 and each of a number of the stimulable phosphor layer regions 27 has the same size as that of each of a number of the absorptive regions 4 formed in the substrate 2 of the biochemical analysis unit 1.

Therefore, although not accurately shown in FIG. 7, substantially circular stimulable phosphor layer regions 27 having a size of about 0.01 mm$^2$ are regularly formed in the manner of a matrix of 120 columns×160 lines in the support 26 of the stimulable phosphor sheet 25 and, therefore, 19,200 stimulable phosphor layer regions 27 are dot-like formed.

In this embodiment, the stimulable phosphor sheet 25 is formed by embedding stimulable phosphor in a number of the through-holes 28 formed in the support 26 in such a manner that the surface of the support 26 and the surface of each of the stimulable phosphor layer regions 27 are located at the same height level.

Figure 8:
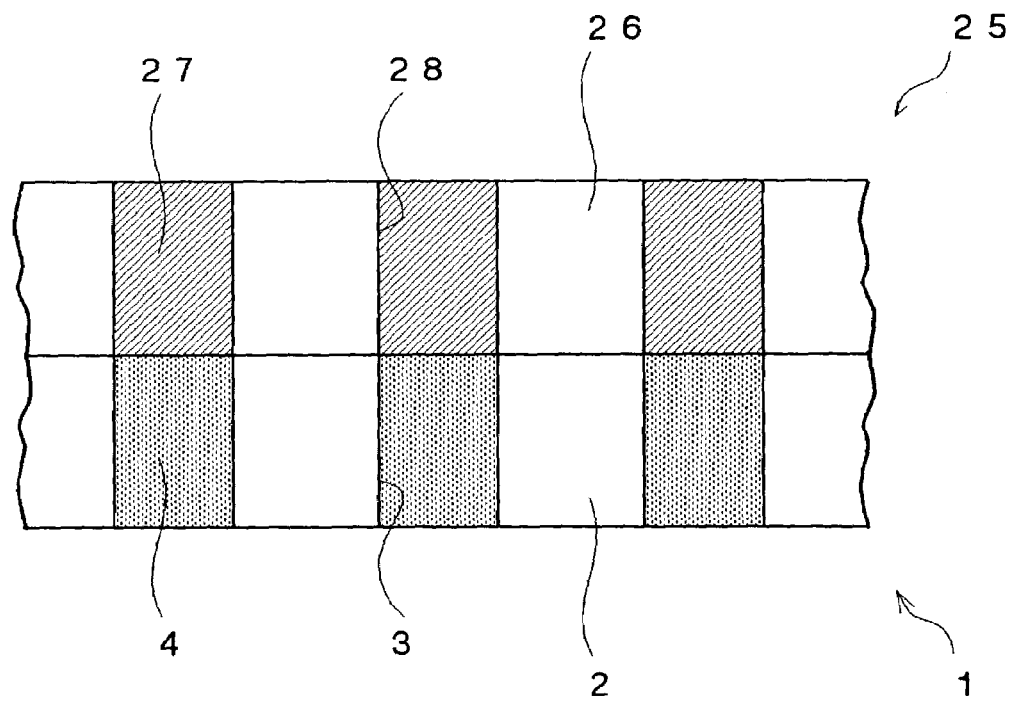
FIG. 8 is a schematic cross-sectional view showing a method for exposing a number of stimulable phosphor layer regions formed in a stimulable phosphor sheet to a radioactive labeling substance contained in a number of absorptive regions formed in a biochemical analysis unit.

FIG. 8 is a schematic cross-sectional view showing a method for exposing a number of the stimulable phosphor layer regions 27 formed in the stimulable phosphor sheet 25 to a radioactive labeling substance contained in a number of the absorptive regions 4 formed in the biochemical analysis unit 1.

As shown in FIG. 8, when the stimulable phosphor layer regions 27 of the stimulable phosphor sheet 25 are to be exposed, the stimulable phosphor sheet 25 is superposed on the biochemical analysis unit 1 in such a manner that a number of the absorptive regions 4 formed in the biochemical analysis unit 1 face the corresponding stimulable phosphor layer regions 27 formed in the support 26 of the stimulable phosphor sheet 25.

In this manner, each of a number of the stimulable phosphor layer regions 27 formed in the support 26 of the stimulable phosphor sheet 25 is kept to face the corresponding absorptive region 4 formed in the biochemical analysis unit 1 for a predetermined time period, whereby a number of the stimulable phosphor layer regions 27 formed in the stimulable phosphor sheet 25 are exposed to the radioactive labeling substance selectively contained in a number of the absorptive regions 4 formed in the biochemical analysis unit 1.

During the exposure operation, electron beams (β rays) are released from the radioactive labeling substance absorbed in the absorptive regions 4 of the biochemical analysis unit 1. However, since a number of the absorptive regions 4 of the biochemical analysis unit 1 are dot-like formed so as to be spaced from each other in the substrate 2 made of aluminum having a property capable of attenuating radiation energy, electron beams (β rays) released from a particular absorptive region 4 of the biochemical analysis unit 1 can be efficiently prevented from scattering in the substrate 2 of the biochemical analysis unit 1, thereby mixing with electron beams (β rays) released from neighboring absorptive regions 4 and entering stimulable phosphor layer regions 27 next the stimulable phosphor layer region 27 corresponding thereto. Further, since a number of the stimulable phosphor layer regions 27 of the stimulable phosphor sheet 25 are formed by embedding stimulable phosphor in a number of the through-holes 28 formed in the support 26 made of nickel and the support 26 is capable of attenuating radiation energy, electron eams (β rays) released from the absorptive regions 4 of the biochemical analysis unit 1 can be efficiently prevented from scattering in the support 26 of the stimulable phosphor sheet 25 and entering stimulable phosphor layer regions 27 next to the corresponding stimulable phosphor layer region 27. Therefore, since it is possible to selectively impinge electron beams (β rays) released from the radioactive labeling substance contained in the individual absorptive regions 4 onto the corresponding stimulable phosphor layer regions 27, it is possible to reliably prevent electron beams (β rays) released from the radioactive labeling substance contained in the individual absorptive regions 4 from entering the stimulable phosphor layer regions 27 of the stimulable phosphor sheet 25 to be exposed to electron beams (β rays) released from neighboring absorptive regions 4 and exposing stimulable phosphor contained therein.

In this manner, radiation data of a radioactive labeling substance are recorded in a number of the stimulable phosphor layer regions 27 formed in the support 26 of the stimulable phosphor sheet 25.

Figure 9:
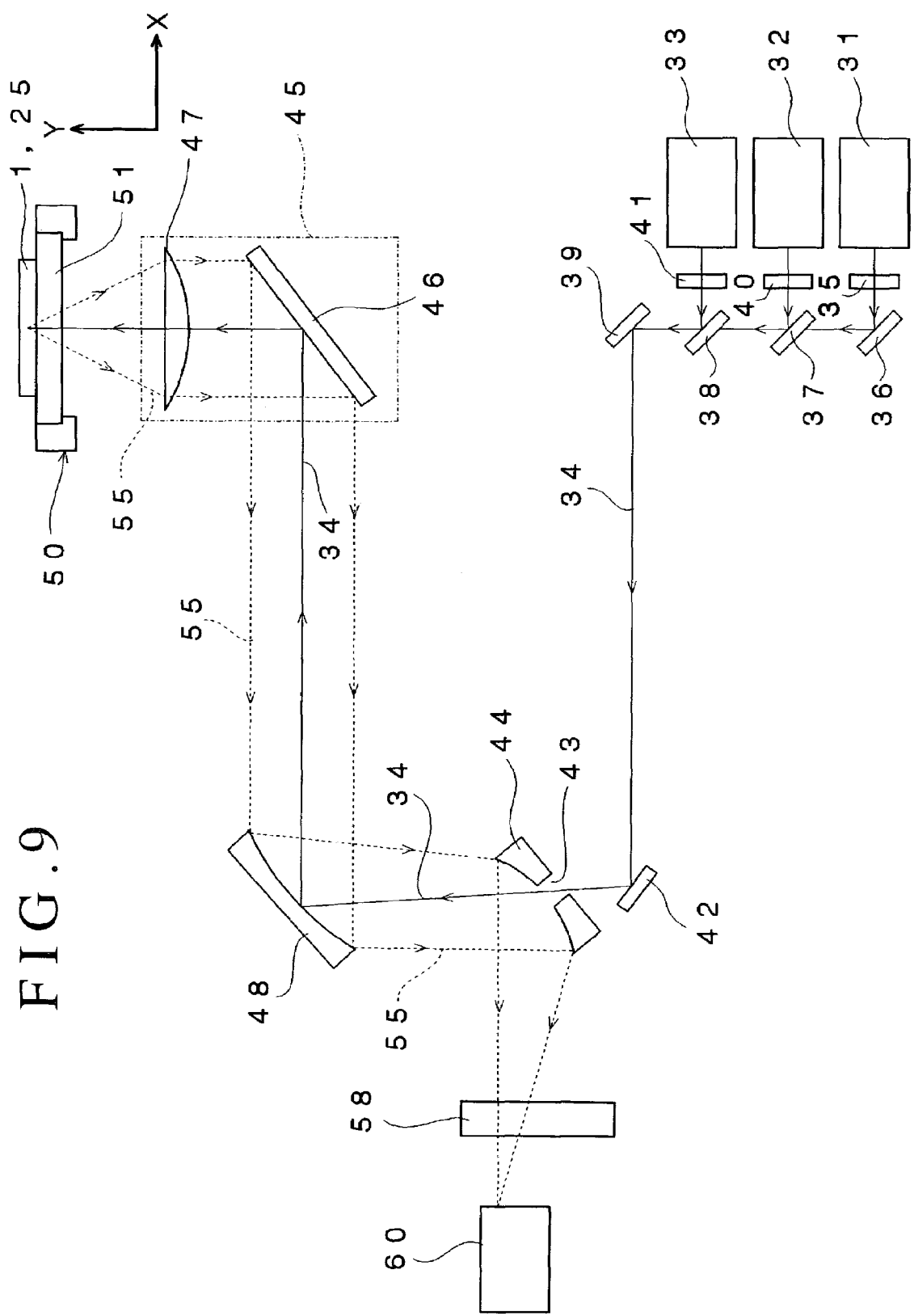
FIG. 9 is a schematic view showing a scanner.
Figure 10:
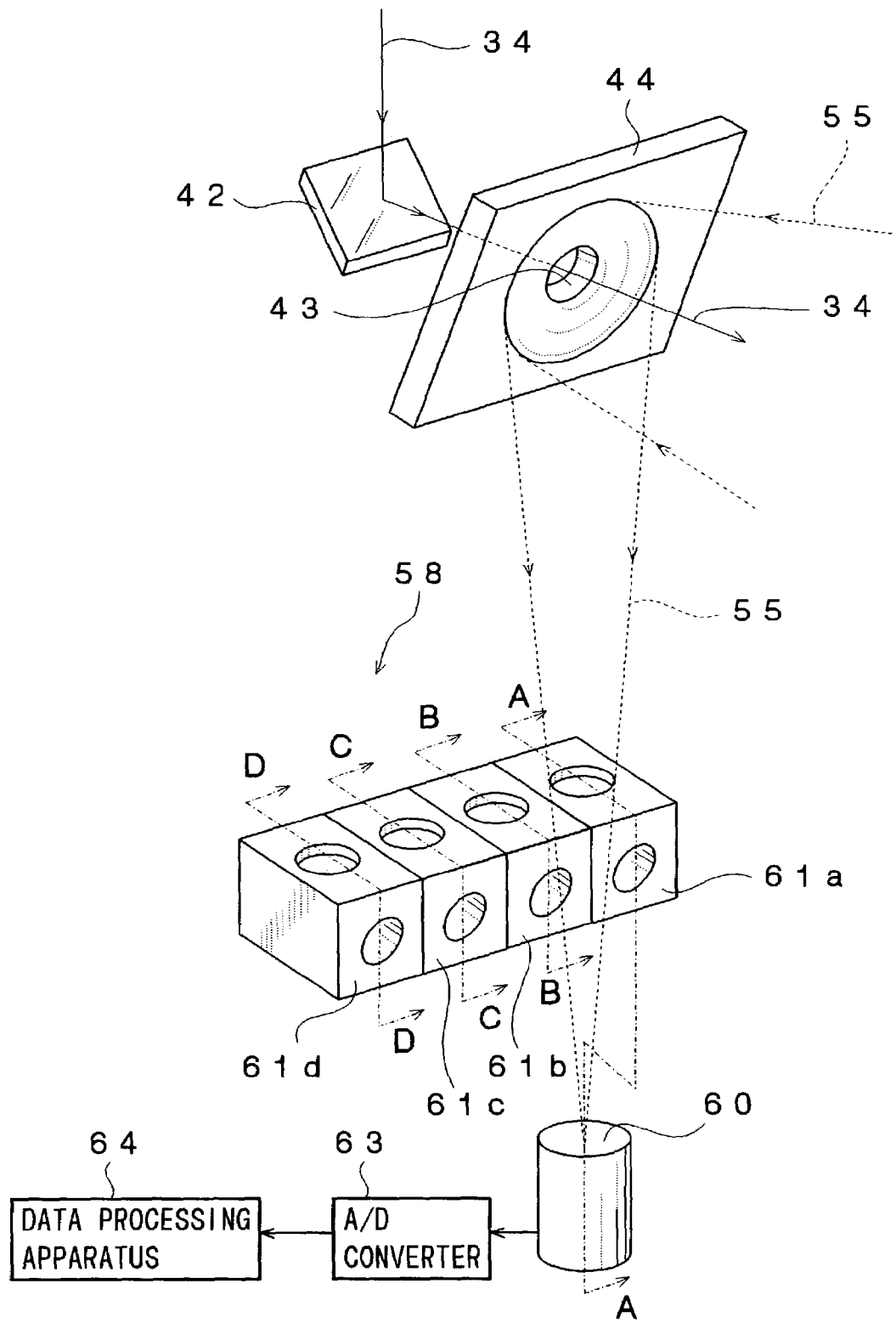
FIG. 10 is a schematic perspective view showing details in the vicinity of a photomultiplier of a scanner shown in FIG. 9.

FIG. 9 is a schematic view showing a scanner for reading radiation data of a radioactive labeling substance recorded in a number of the stimulable phosphor layer regions 27 formed in the stimulable phosphor sheet 25 and fluorescence data of a fluorescent substance such as a fluorescent dye recorded in a number of the absorptive regions 4 formed in the biochemical analysis unit 1 and producing biochemical analysis data, and FIG. 10 is a schematic perspective view showing details in the vicinity of a photomultiplier of the scanner.

The scanner shown in FIG. 9 is constituted so as to read radiation data of a radioactive labeling substance recorded in a number of the stimulable phosphor layer regions 27 formed in the stimulable phosphor sheet 25 and fluorescence data of a fluorescent substance such as a fluorescent dye recorded in a number of the absorptive regions 4 of the biochemical analysis unit 1 to produce biochemical analysis data and includes a first laser stimulating ray source 31 for emitting a laser beam 34 having a wavelength of 640 nm, a second laser stimulating ray source 32 for emitting a laser beam 34 having a wavelength of 532 nm and a third laser stimulating ray source 33 for emitting a laser beam 34 having a wavelength of 473 nm.

In this embodiment, the first laser stimulating ray source 31 is constituted by a semiconductor laser beam source and the second laser stimulating ray source 32 and the third laser stimulating ray source 33 are constituted by a second harmonic generation element.

A laser beam 34 emitted from the first laser stimulating source 31 passes through a collimator lens 35, thereby being made a parallel beam, and is reflected by a mirror 36. A first dichroic mirror 37 for transmitting light having a wavelength of 640 nm but reflecting light having a wavelength of 532 nm and a second dichroic mirror 38 for transmitting light having a wavelength equal to and longer than 532 nm but reflecting light having a wavelength of 473 nm are provided in the optical path of the laser beam 34 emitted from the first laser stimulating ray source 31. The laser beam 34 emitted from the first laser stimulating ray source 31 and reflected by the mirror 36 passes through the first dichroic mirror 37 and the second dichroic mirror 38 and advances to a mirror 39.

On the other hand, the laser beam 34 emitted from the second laser stimulating ray source 32 passes through a collimator lens 40, thereby being made a parallel beam, and is reflected by the first dichroic mirror 37, thereby changing its direction by 90 degrees. The laser beam 34 then passes through the second dichroic mirror 38 and advances to the mirror 39.

Further, the laser beam 34 emitted from the third laser stimulating ray source 33 passes through a collimator lens 41, thereby being made a parallel beam, and is reflected by the second dichroic mirror 38, thereby changing its direction by 90 degrees. The laser beam 34 then advances to the mirror 39.

The laser beam 34 advancing to the mirror 39 is reflected by the mirror 39 and advances to a mirror 42 to be reflected thereby.

A perforated mirror 44 formed with a hole 43 at the center portion thereof is provided in the optical path of the laser beam 34 reflected by the mirror 42. The laser beam 34 reflected by the mirror 42 passes through the hole 43 of the perforated mirror 44 and advances to a concave mirror 48.

The laser beam 34 advancing to the concave mirror 48 is reflected by the concave mirror 48 and enters an optical head 45.

The optical head 45 includes a mirror 46 and an aspherical lens 47. The laser beam 34 entering the optical head 45 is reflected by the mirror 46 and impinged by the aspherical lens 47 onto one of a number of the stimulable phosphor layer regions 27 of the stimulable phosphor sheet 25 or one of a number of the absorptive regions 4 of the biochemical analysis unit 1 placed on the glass plate 51 of a stage 50.

When the laser beam 34 impinges on one of the stimulable phosphor layer regions 27 formed in the support 26 of the stimulable phosphor sheet 25, stimulable phosphor contained in the stimulable phosphor layer region 27 is excited, thereby releasing stimulated emission 55. On the other hand, when the laser beam 34 impinges on one of the absorptive regions 4 formed in the substrate 2 of the biochemical analysis unit 1, a fluorescent substance such as a fluorescent dye contained in the absorptive region 4 is excited, thereby releasing fluorescence emission 55.

The stimulated emission 55 released from the stimulable phosphor layer region 27 formed in the stimulable phosphor 25 or the fluorescence emission 55 released from the absorptive region 4 formed in the biochemical analysis unit 1 is condensed onto the mirror 46 by the aspherical lens 47 provided in the optical head 45 and reflected by the mirror 46 on the side of the optical path of the laser beam 34, thereby being made a parallel beam to advance to the concave mirror 48.

The stimulated emission 55 or the fluorescence emission 55 advancing to the concave mirror 48 is reflected by the concave mirror 48 and advances to the perforated mirror 44.

As shown in FIG. 10, the stimulated emission 55 or the fluorescence emission 55 advancing to the perforated mirror 44 is reflected downward by the perforated mirror 44 formed as a concave mirror and advances to a filter unit 58, whereby light having a predetermined wavelength is cut. The stimulated emission 55 or the fluorescence emission 55 then impinges on a photomultiplier 60, thereby being photoelectrically detected.

As shown in FIG. 10, the filter unit 58 is provided with four filter members 61a, 61b, 61c and 61d and is constituted to be laterally movable in FIG. 10 by a motor (not shown).

Figure 11:
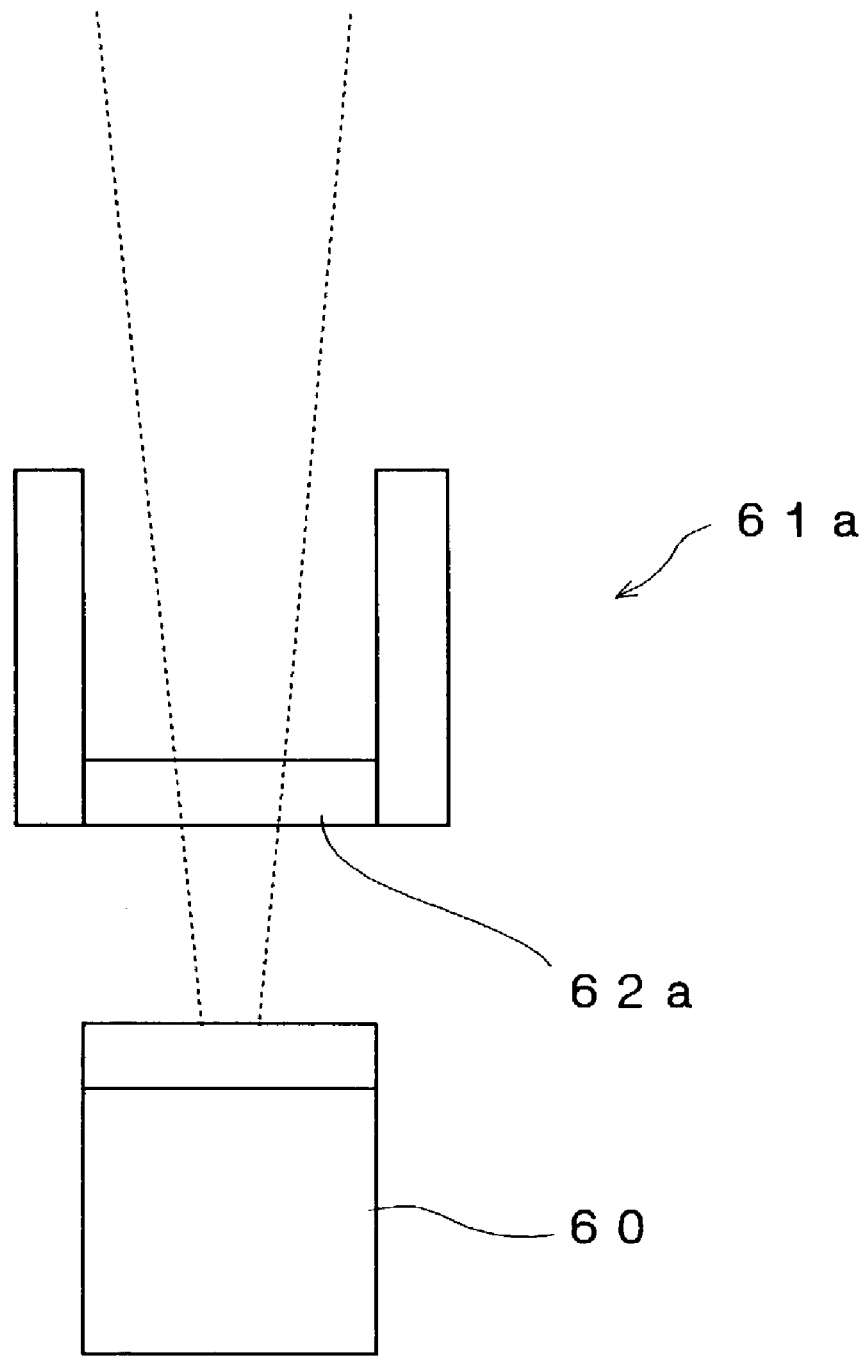
FIG. 11 is a schematic cross-sectional view taken along a line AA in FIG. 10.

FIG. 11 is a schematic cross-sectional view taken along a line A-A in FIG. 10.

As shown in FIG. 11, the filter member 61a includes a filter 62a and the filter 62a is used for reading fluorescence emission 55 by stimulating a fluorescent substance such as a fluorescent dye contained in a number of the absorptive regions 4 formed in the biochemical analysis unit 1 using the first laser stimulating ray source 31 and has a property of cutting off light having a wavelength of 640 nm but transmitting light having a wavelength longer than 640 nm.

Figure 12:
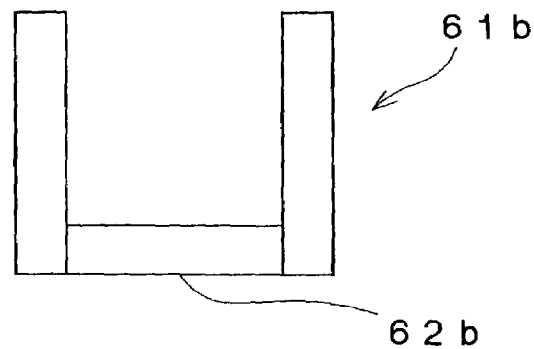
FIG. 12 is a schematic cross-sectional view taken along a line BB in FIG. 10.

FIG. 12 is a schematic cross-sectional view taken along a line BB in FIG. 10.

As shown in FIG. 12, the filter member 61b includes a filter 62b and the filter 62b is used for reading fluorescence emission 55 by stimulating a fluorescent substance such as a fluorescent dye contained in a number of the absorptive regions 4 formed in the biochemical analysis unit 1 using the second laser stimulating ray source 32 and has a property of cutting off light having a wavelength of 532 nm but transmitting light having a wavelength longer than 532 nm.

Figure 13:
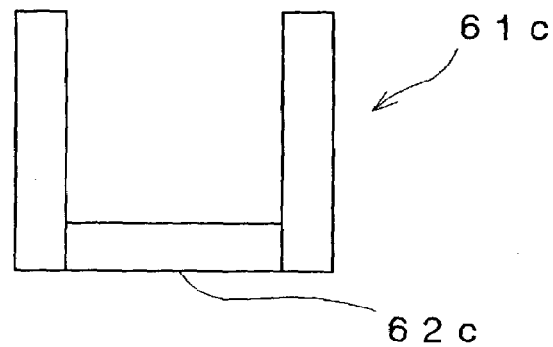
FIG. 13 is a schematic cross-sectional view taken along a line CC in FIG. 10.

FIG. 13 is a schematic cross-sectional view taken along a line CC in FIG. 10.

As shown in FIG. 13, the filter member 61c includes a filter 62c and the filter 62c is used for reading fluorescence emission 55 by stimulating a fluorescent substance such as a fluorescent dye contained in a number of the absorptive regions 4 formed in the biochemical analysis unit 1 using the third laser stimulating ray source 33 and has a property of cutting off light having a wavelength of 473 nm but transmitting light having a wavelength longer than 473 nm.

Figure 14:
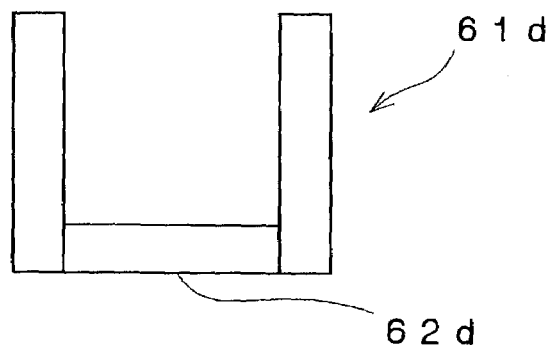
FIG. 14 is a schematic cross-sectional view taken along a line DD in FIG. 10.

FIG. 14 is a schematic cross-sectional view taken along a line DD in FIG. 10.

As shown in FIG. 13, the filter member 61d includes a filter 62d and the filter 62d is used for reading stimulated emission 55 released from stimulable phosphor contained in a number of the dot-like stimulable phosphor layer regions 27 formed in the stimulable phosphor sheet 25 upon being stimulated using the first laser stimulating ray source 31 and has a property of transmitting only light having a wavelength corresponding to that of stimulated emission 55 emitted from stimulable phosphor and cutting off light having a wavelength of 640 nm.

Therefore, in accordance with the kind of a stimulating ray source to be used, one of these filter members 61a, 61b, 61c, 61d is selectively positioned in front of the photomultiplier 60, thereby enabling the photomultiplier 60 to photoelectrically detect only light to be detected.

The analog data produced by photoelectrically detecting stimulated emission 55 or fluorescence emission 55 with the photomultiplier 60 are converted by an A/D converter 63 into digital data and the digital data are fed to a data processing apparatus 64.

Although not shown in FIG. 9, the optical head 45 is constituted to be movable by a scanning mechanism in a main scanning direction indicated by an arrow X and a sub-scanning direction indicated by an arrow Y in FIG. 9 so that all of the dot-like stimulable phosphor layer regions 27 formed in the stimulable phosphor sheet 25 or all of the absorptive regions 4 formed in the biochemical analysis unit 1 can be scanned by the laser beam 34.

Figure 15:
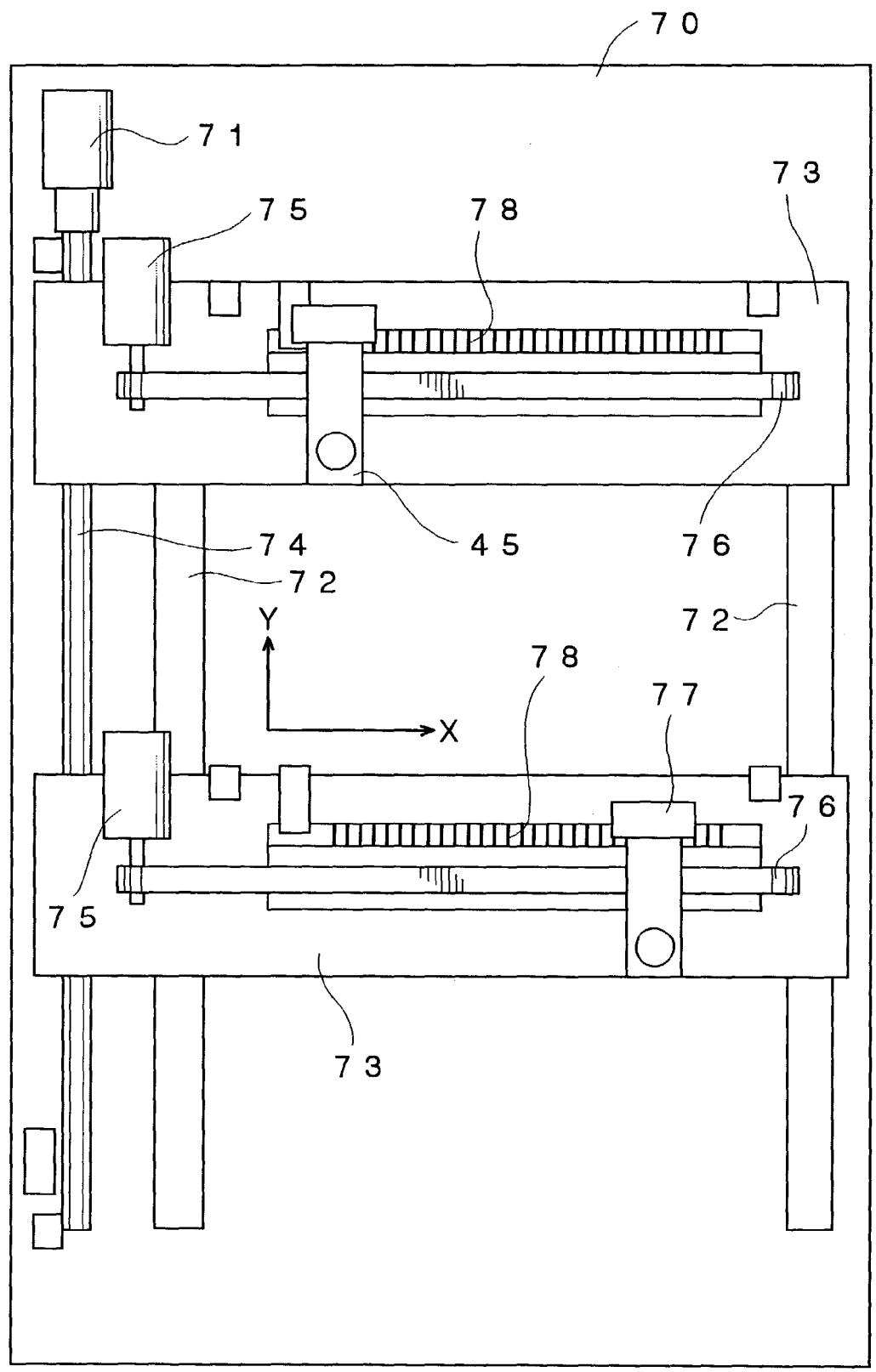
FIG. 15 is a schematic plan view showing a scanning mechanism of an optical head.

FIG. 15 is a schematic plan view showing the scanning mechanism of the optical head 45.

In FIG. 15, optical systems other than the optical head 45 and the paths of the laser beam 34 and stimulated emission 55 or fluorescence emission 55 are omitted for simplification.

As shown in FIG. 15, the scanning mechanism of the optical head 45 includes a base plate 70, and a sub-scanning pulse motor 71 and a pair of rails 72, 72 are fixed on the base plate 70. A movable base plate 73 is further provided so as to be movable in the sub-scanning direction indicated by an arrow Y in FIG. 15.

The movable base plate 73 is formed with a threaded hole (not shown) and a threaded rod 74 rotated by the sub-scanning pulse motor 71 is engaged with the inside of the hole.

A main scanning stepping motor 75 is provided on the movable base plate 73. The main scanning stepping motor 75 is adapted for intermittently driving an endless belt 76 by a pitch equal to the distance between neighboring absorptive regions 4 formed in the biochemical analysis unit 1, namely, the distance between neighboring stimulable phosphor layer regions 27 formed in the stimulable phosphor sheet 25. The optical head 45 is fixed to the endless belt 76 and when the endless belt 76 is driven by the main scanning stepping motor 75, the optical head 45 is moved in the main scanning direction indicated by an arrow X in FIG. 15.

In FIG. 15, the reference numeral 77 designates a linear encoder for detecting the position of the optical head 45 in the main scanning direction and the reference numeral 78 designates slits of the linear encoder 77.

Therefore, when the endless belt 76 is driven in the main scanning direction by the main scanning stepping motor 75 and the scanning of one line is completed, the substrate 73 is intermittently moved in the sub-scanning direction by the sub-scanning pulse motor 71, whereby the optical head 45 is moved in the main scanning direction indicated by the arrow X and the sub-scanning direction indicated by the arrow Y in FIG. 15 and all of the stimulable phosphor layer regions 27 formed in the support 26 of the stimulable phosphor sheet 25 or all of the absorptive regions 4 formed in the substrate 2 of the biochemical analysis unit 1 are scanned with the laser beam 34.

Figure 16:
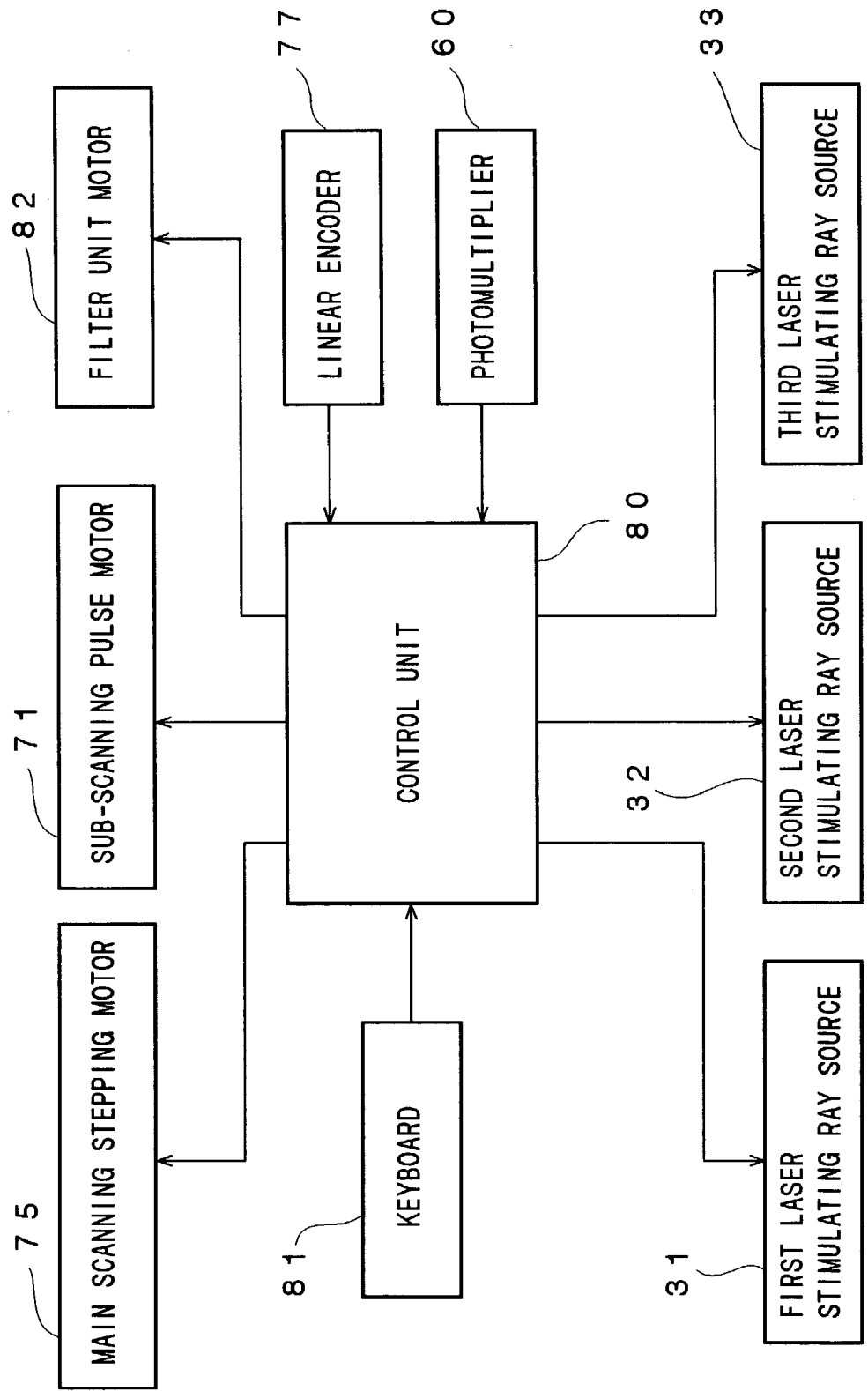
FIG. 16 is a block diagram of a control system, an input system, a drive system and a detection system of the scanner shown in FIG. 9.

FIG. 16 is a block diagram of a control system, an input system, a drive system and a detection system of the scanner shown in FIG. 9.

As shown in FIG. 16, the control system of the scanner includes a control unit 80 for controlling the overall operation of the scanner and the input system of the scanner includes a keyboard 81 which can be operated by a user and through which various instruction signals can be input.

As shown in FIG. 16, the drive system of the scanner includes the main scanning stepping motor 75 for intermittently moving the optical head 45 in the main scanning direction, the sub-scanning pulse motor 71 for moving the optical head 45 in the sub-scanning direction and a filter unit motor 82 for moving the filter unit 58 provided with the four filter members 61a, 61b, 61c and 61d.

The control unit 80 is adapted for selectively outputting a drive signal to the first laser stimulating ray source 31, the second laser stimulating ray source 32 or the third laser stimulating ray source 33 and outputting a drive signal to the filter unit motor 82.

As shown in FIG. 16, the detection system of the scanner includes the photomultiplier 60 and the linear encoder 77 for detecting the position of the optical head 45 in the main scanning direction.

In this embodiment, the control unit 80 is adapted to control the on and off operation of the first laser stimulating ray source 31, the second laser stimulating ray source 32 or the third laser stimulating ray source 33 in accordance with a detection signal indicating the position of the optical head 45 input from the linear encoder 77.

The thus constituted scanner reads radiation data of a radioactive labeling substance recorded in a stimulable phosphor sheet 25 by exposing a number of the stimulable phosphor layer regions 27 to a radioactive labeling substance contained in a number of the absorptive regions 4 formed in the biochemical analysis unit 1 and produces biochemical analysis data in the following manner.

A stimulable phosphor sheet 25 is first set on the glass plate 51 of the stage 50 by a user.

An instruction signal indicating that a number of the stimulable phosphor regions 27 of the stimulable phosphor sheet 25 are to be scanned with the laser beam 34 is then input through the keyboard 81.

The instruction signal input through the keyboard 81 is input to the control unit 80 and the control unit 80 outputs a drive signal to the filter unit motor 82 in accordance with the instruction signal, thereby moving the filter unit 58 so as to locate the filter member 61d provided with the filter 62d having a property of transmitting only light having a wavelength corresponding to that of stimulated emission emitted from stimulable phosphor but cutting off light having a wavelength of 640 nm in the optical path of stimulated emission 55.

The control unit 80 further outputs a drive signal to the main scanning stepping motor 75 to move the optical head 45 in the main scanning direction and when it determines based on a detection signal indicating the position of the optical head 45 input from the linear encoder 77 that the optical head 45 has reached a position where a laser beam 34 can be projected onto a first stimulable phosphor layer region 27 among a number of the stimulable phosphor layer regions 27 formed in the stimulable phosphor sheet 25, it outputs a drive stop signal to the main scanning stepping motor 75 and a drive signal to the first stimulating ray source 31, thereby actuating it to emit a laser beam 34 having a wavelength of 640 nm.

A laser beam 34 emitted from the first laser stimulating source 31 passes through the collimator lens 35, thereby being made a parallel beam, and is reflected by the mirror 36.

The laser beam 34 reflected by the mirror 36 passes through the first dichroic mirror 37 and the second dichroic mirror 38 and advances to the mirror 39.

The laser beam 34 advancing to the mirror 39 is reflected by the mirror 39 and advances to the mirror 42 to be reflected thereby.

The laser beam 34 reflected by the mirror 42 passes through the hole 43 of the perforated mirror 44 and advances to the concave mirror 48.

The laser beam 34 advancing to the concave mirror 48 is reflected by the concave mirror 48 and enters the optical head 45.

The laser beam 34 entering the optical head 45 is reflected by the mirror 46 and condensed by the aspherical lens 47 onto the first stimulable phosphor layer region 27 of the stimulable phosphor sheet 25 placed on the glass plate 51 of a stage 50.

As a result, stimulable phosphor contained in the first stimulable phosphor layer region 27 formed in the support 26 of the stimulable phosphor sheet 25 is excited by the laser beam 34, thereby releasing stimulated emission 55 from the first stimulable phosphor layer region 27.

The stimulated emission 55 released from the first stimulable phosphor layer region 27 is condensed onto the mirror 46 by the aspherical lens 47 provided in the optical head 45 and reflected by the mirror 46 on the side of the optical path of the laser beam 34, thereby being made a parallel beam to advance to the concave mirror 48.

The stimulated emission 55 advancing to the concave mirror 48 is reflected by the concave mirror 48 and advances to the perforated mirror 44.

As shown in FIG. 10, the stimulated emission 55 advancing to the perforated mirror 44 is reflected downward by the perforated mirror 44 formed as a concave mirror and advances to the filter 62d of the filter unit 58.

Since the filter 62d has a property of transmitting only light having a wavelength corresponding to that of stimulated emission 55 emitted from stimulable phosphor and cutting off light having a wavelength of 640 nm, light having a wavelength of 640 nm corresponding to that of the stimulating ray is cut off by the filter 62d and only light having a wavelength corresponding to that of stimulated emission 55 passes through the filter 62d to be photoelectrically detected by the photomultiplier 60.

Analog data produced by photoelectrically detecting stimulated emission 55 with the photomultiplier 60 are converted by an A/D converter 63 into digital data and the digital data are fed to a data processing apparatus 64.

When a predetermined time, for example, several microseconds, has passed after the first stimulating ray source 31 was turned on, the control unit 80 outputs a drive stop signal to the first stimulating ray source 31, thereby turning it off and outputs a drive signal to the main scanning stepping motor 75, thereby moving the optical head 45 by one pitch equal to the distance between neighboring stimulable phosphor layer regions 27 formed in the support 26 of the stimulable phosphor sheet 25.

When the control unit 80 determines based on a detection signal indicating the position of the optical head 45 input from the linear encoder 77 that the optical head 45 has been moved by one pitch equal to the distance between neighboring stimulable phosphor layer regions 27 and has reached a position where a laser beam 34 can be projected onto a second stimulable phosphor layer region 27 next to the first stimulable phosphor layer region 27 formed in the support 26 of the stimulable phosphor sheet 25, it outputs a drive signal to the first stimulating ray source 31 to turn it on, thereby causing the laser beam 34 to excite stimulable phosphor contained in the second stimulable phosphor layer region 27 formed in the support 26 of the stimulable phosphor sheet 25 next to the first stimulable phosphor layer region 27.

Similarly to the above, the second stimulable phosphor layer region 27 formed in the support 26 of the stimulable phosphor sheet 27 is irradiated with the laser beam 34 for a predetermined time, whereby stimulable phosphor contained in the second stimulable phosphor layer region 27 is excited and when stimulated emission 55 released from the second stimulable phosphor layer region 27 is photoelectrically detected by the photomultiplier 60 and analog data are produced, the control unit 80 outputs a drive stop signal to the first stimulating ray source 31, thereby turning it off and outputs a drive signal to the main scanning stepping motor 75, thereby moving the optical head 45 by one pitch equal to the distance between neighboring stimulable phosphor layer regions 27.

In this manner, the on and off operation of the first stimulating ray source 31 is repeated in synchronism with the intermittent movement of the optical head 45 and when the control unit 80 determines based on a detection signal indicating the position of the optical head 45 input from the linear encoder 77 that the optical head 45 has been moved by one scanning line in the main scanning direction and that the stimulable phosphor layer regions 27 included in a first line of the stimulable phosphor layer regions 27 formed in the support 26 of the stimulable phosphor sheet 25 have been scanned with the laser beam 34, it outputs a drive signal to the main scanning stepping motor 75, thereby returning the optical head 45 to its original position and outputs a drive signal to the sub-scanning pulse motor 71, thereby causing it to move the movable base plate 73 by one scanning line in the sub-scanning direction.

When the control unit 80 determines based on a detection signal indicating the position of the optical head 45 input from the linear encoder 77 that the optical head 45 has been returned to its original position and determines that the movable base plate 73 has been moved by one scanning line in the sub-scanning direction, similarly to the manner in which the stimulable phosphor layer regions 27 included in the first line of the stimulable phosphor layer regions 27 formed in the support 26 of the stimulable phosphor sheet 25 were sequentially irradiated with the laser beam 34 emitted from the first laser stimulating ray source 31, the stimulable phosphor layer regions 27 included in a second line of the stimulable phosphor layer regions 27 formed in the support 26 of the stimulable phosphor sheet 25 are sequentially irradiated with the laser beam 34 emitted from the first laser stimulating ray source 31, thereby exciting stimulable phosphor contained in the stimulable phosphor layer regions 27 included in the second line and stimulated emission 55 released from the stimulable phosphor layer regions 27 included in the second line is sequentially and photoelectrically detected by the photomultiplier 60.

Analog data produced by photoelectrically detecting stimulated emission 55 with the photomultiplier 60 are converted by an A/D converter 63 into digital data and the digital data are fed to a data processing apparatus 64.

When all of the stimulable phosphor layer regions 27 formed in the support 26 of the stimulable phosphor sheet 25 have been scanned with the laser beam 34 to excite stimulable phosphor contained in the stimulable phosphor layer regions 27 and digital data produced by photoelectrically detecting stimulated emission 55 released from the stimulable phosphor layer regions 27 by the photomultiplier 60 to produce analog data and digitizing the analog data by the A/D converter 63 have been forwarded to the data processing apparatus 64, the control unit 80 outputs a drive stop signal to the first laser stimulating ray source 31, thereby turning it off.

As described above, radiation data recorded in a number of the stimulable phosphor layer regions 27 formed in the support 26 of the stimulable phosphor sheet 25 are read by the scanner to produce biochemical analysis data.

On the other hand, when fluorescence data of a fluorescent substance recorded in a number of the absorptive regions 4 formed in the biochemical analysis unit 1 are to be read to produce biochemical analysis data, the biochemical analysis unit 1 is first set by the user on the glass plate 51 of the stage 50.

A fluorescent substance identification signal for identifying the kind of a fluorescent substance used as a labeling substance and a reading instruction signal indicating that fluorescent data are to be read are then input by the user through the keyboard 81.

The fluorescent substance identification signal and the instruction signal input through the keyboard 81 are input to the control unit 80 and when the control unit 80 receives them, it determines the laser stimulating ray source to be used in accordance with a table stored in a memory (not shown) and also determines what filter is to be positioned in the optical path of fluorescence emission 55 among the filters 62a, 62b and 62c.

For example, when Rhodamine (registered trademark), which can be most efficiently stimulated by a laser beam having a wavelength of 532 nm, is used as a fluorescent substance for labeling a substance derived from a living organism and the fluorescent substance identification signal indicating such a fact is input, the control unit 80 selects the second laser stimulating ray source 32 and the filter 62b and outputs a drive signal to the filter unit motor 82, thereby moving the filter unit 58 so that the filter member 61b inserting the filter 62b having a property of cutting off light having a wavelength of 532 nm but transmitting light having a wavelength longer than 532 nm in the optical path of the fluorescence emission 55.

The control unit 80 further outputs a drive signal to the main scanning stepping motor 75 to move the optical head 45 in the main scanning direction and when it determines based on a detection signal indicating the position of the optical head 45 input from the linear encoder 77 that the optical head 45 has reached a position where a laser beam 34 can be projected onto a first absorptive region 4 among a number of the absorptive regions 4 formed in the biochemical analysis unit 1, it outputs a drive stop signal to the main scanning stepping motor 75 and a drive signal to the second laser stimulating ray source 32, thereby actuating it to emit a laser beam 34 having a wavelength of 532 nm.

The laser beam 34 emitted from the second laser stimulating ray source 32 is made a parallel beam by the collimator lens 40, advances to the first dichroic mirror 37 and is reflected thereby.

The laser beam 34 reflected by the first dichroic mirror 37 transmits through the second dichroic mirror 38 and advances to the mirror 39.

The laser beam 34 advancing to the mirror 39 is reflected by the mirror 39 and further advances to the mirror 42 to be reflected thereby.

The laser beam 34 reflected by the mirror 42 advances to the perforated mirror 44 and passes through the hole 43 of the perforated mirror 44. Then, the laser beam 34 advances to the concave mirror 48.

The laser beam 34 advancing to the concave mirror 48 is reflected thereby and enters the optical head 45.

The laser beam 34 entering the optical head 45 is reflected by the mirror 46 and condensed by the aspherical lens 47 onto the first absorptive region 4 of the biochemical analysis unit 1 placed on the glass plate 51 of the stage 50.

As a result, a fluorescent substance such as a fluorescent dye, for instance, Rhodamine, contained in the absorptive region 4 formed in the biochemical analysis unit 1 is stimulated by the laser beam 34 and fluorescence emission 55 is released from Rhodamine.

In this embodiment, a number of the absorptive regions 4 of the biochemical analysis unit 1 are formed to be spaced apart from each other in the substrate 2 made of aluminum and the substrate 2 is capable of attenuating light energy, it is possible to reliably prevent fluorescence emission 55 generated by exciting a fluorescent substance contained in each of the absorptive regions 4 with the laser beams 24 and released from each of the absorptive regions 4 from mixing fluorescence emission 55 generated by exciting a fluorescent substance contained in neighboring absorptive regions 4.

The fluorescence emission 55 released from Rhodamine is condensed by the aspherical lens 47 provided in the optical head 45 and reflected by the mirror 46 on the side of an optical path of the laser beam 34, thereby being made a parallel beam to advance to the concave mirror 48.

The fluorescence emission 55 advancing to the concave mirror 48 is reflected by the concave mirror 48 and advances to the perforated mirror 44.

As shown in FIG. 10, the fluorescence emission 55 advancing to the perforated mirror 44 is reflected downward by the perforated mirror 44 formed as a concave mirror and advances to the filter 62b of a filter unit 58.

Since the filter 62b has a property of cutting off light having a wavelength of 532 nm but transmitting light having a wavelength longer than 532 nm, light having the same wavelength of 532 nm as that of the stimulating ray is cut off by the filter 62b and only light in the wavelength of the fluorescence emission 55 released from Rhodamine passes through the filter 62b to be photoelectrically detected by the photomultiplier 60.

Analog data produced by photoelectrically detecting fluorescence emission 55 with the photomultiplier 60 are converted by the A/D converter 63 into digital data and the digital data are fed to a data processing apparatus 64.

When a predetermined time, for example, several microseconds, has passed after the second laser stimulating ray source 32 was turned on, the control unit 80 outputs a drive stop signal to the second laser stimulating ray source 32, thereby turning it off and outputs a drive signal to the main scanning stepping motor 75, thereby moving the optical head 45 by one pitch equal to the distance between neighboring absorptive regions 4 formed in the biochemical analysis unit 1.

When the control unit 80 determines based on a detection signal indicating the position of the optical head 45 input from the linear encoder 77 that the optical head 45 has been moved by one pitch equal to the distance between neighboring absorptive regions 4 formed in the biochemical analysis unit 1 and has reached a position where a laser beam 34 can be projected onto a second absorptive region 4 next to the first absorptive region 4 formed in the substrate 2 of the biochemical analysis unit 1, it outputs a drive signal to the second laser stimulating ray source 32 to turn it on, thereby causing the laser beam 34 to excite a fluorescent substance, for example, Rhodamine, contained in the second absorptive region 4 formed in the substrate 2 of the biochemical analysis unit 1 next to the first absorptive region 4.

Similarly to the above, the second absorptive region 4 formed in the substrate 2 of the biochemical analysis unit 1 is irradiated with the laser beam 34 for a predetermined time and when fluorescence emission 55 released from the second absorptive region 4 is photoelectrically detected by the photomultiplier 60 and analog data are produced, the control unit 80 outputs a drive stop signal to the second laser stimulating ray source 32, thereby turning it off and outputs a drive signal to the main scanning stepping motor 75, thereby moving the optical head 45 by one pitch equal to the distance between neighboring absorptive regions 4 formed in the substrate 2 of the biochemical analysis unit 1.

In this manner, the on and off operation of the second laser stimulating ray source 32 is repeated in synchronism with the intermittent movement of the optical head 45 and when the control unit 80 determines based on a detection signal indicating the position of the optical head 45 input from the linear encoder 77 that the optical head 45 has been moved by one scanning line in the main scanning direction and that the absorptive regions 4 included in a first line of the absorptive regions 4 formed in the substrate 2 of the biochemical analysis unit 1 have been scanned with the laser beam 34, it outputs a drive signal to the main scanning stepping motor 75, thereby returning the optical head 45 to its original position and outputs a drive signal to the sub-scanning pulse motor 71, thereby causing it to move the movable base plate 73 by one scanning line in the sub-scanning direction.

When the control unit 80 determines based on a detection signal indicating the position of the optical head 45 input from the linear encoder 77 that the optical head 45 has been returned to its original position and determines that the movable base plate 73 has been moved by one scanning line in the sub-scanning direction, similarly to the manner in which the absorptive regions 4 included in the first line of the absorptive regions 4 formed in the substrate 2 of the biochemical analysis unit 1 were sequentially irradiated with the laser beam 34 emitted from the second laser stimulating ray source 32, the absorptive regions 4 included in a second line of the absorptive regions 4 formed in the substrate 2 of the biochemical analysis unit 1 are sequentially irradiated with the laser beam 34 emitted from the second laser stimulating ray source 32, thereby exciting Rhodamine contained in the absorptive regions 4 included in the second line and fluorescence emission 55 released from the absorptive regions 4 included in the second line is sequentially and photoelectrically detected by the photomultiplier 60.

Analog data produced by photoelectrically detecting fluorescence emission 55 with the photomultiplier 60 are converted by the A/D converter 63 into digital data and the digital data are fed to the data processing apparatus 64.

When all of the absorptive regions 4 formed in the substrate 2 of the biochemical analysis unit 1 have been scanned with the laser beam 34 to excite Rhodamine contained in the absorptive regions 4 formed in the substrate 2 of the biochemical analysis unit 1 and digital data produced by photoelectrically detecting fluorescence emission 55 released from the absorptive regions 4 by the photomultiplier 60 to produce analog data and digitizing the analog data by the A/D converter 63 have been forwarded to the data processing apparatus 64, the control unit 80 outputs a drive stop signal to the second laser stimulating ray source 32, thereby turning it off.

As described above, fluorescence data recorded in a number of the absorptive regions 4 formed in the substrate 2 of the biochemical analysis unit 1 are read by the scanner to produce biochemical analysis data.

On the other hand, chemiluminescent data recorded in a number of the absorptive regions 4 formed in the substrate 2 of the biochemical analysis unit 1 are read by a data producing system including a cooled CCD camera to produce biochemical analysis data.

Figure 17:
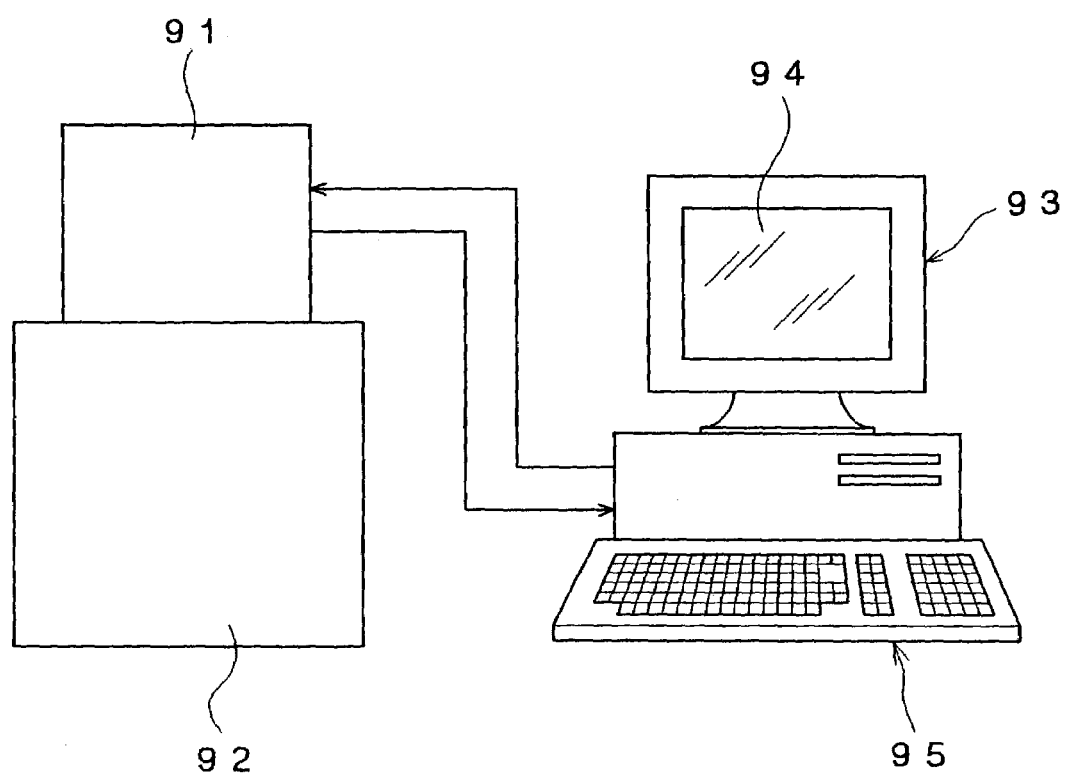
FIG. 17 is a schematic front view showing a data producing system for reading chemiluminescence data recorded in a number of the absorptive regions formed in a substrate of a biochemical analysis unit, and producing biochemical analysis data.

FIG. 17 is a schematic front view showing a data producing system for reading chemiluminescence data recorded in a number of the absorptive regions 4 formed in the substrate 2 of the biochemical analysis unit 1, and producing biochemical analysis data.

The data producing system shown in FIG. 17 is constituted to be able to also read fluorescence data of a fluorescent substance such as a fluorescent dye recorded in a number of the absorptive regions 4 formed in the biochemical analysis unit 1.

As shown in FIG. 17, the data producing system includes a cooled CCD camera 91, a dark box 92 and a personal computer 93. As shown in FIG. 17, the personal computer 93 is equipped with a CRT 94 and a keyboard 95.

Figure 18:
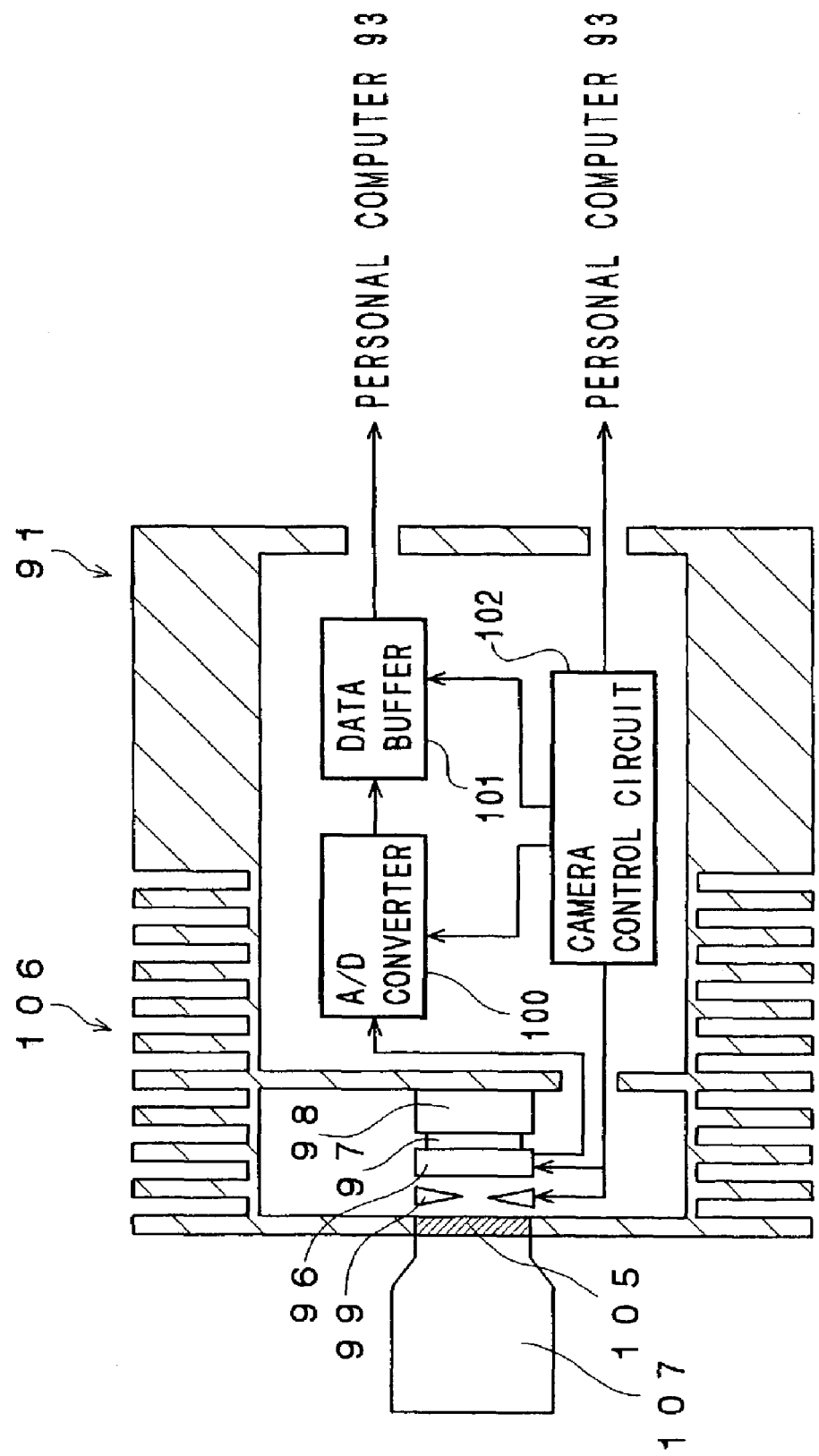
FIG. 18 is a schematic longitudinal cross sectional view showing a cooled CCD camera of a data producing system.

FIG. 18 is a schematic longitudinal cross sectional view showing the cooled CCD camera 91 of the data producing system.

As shown in FIG. 18, the cooled CCD camera 91 includes a CCD 96, a heat transfer plate 97 made of metal such as aluminum, a Peltier element 98 for cooling the CCD 96, a shutter 99 disposed in front of the CCD 96, an A/D converter 100 for converting analog data produced by the CCD 96 to digital data, a data buffer 101 for temporarily storing the data digitized by the A/D converter 100, and a camera control circuit 102 for controlling the operation of the cooled CCD camera 91. An opening formed between the dark box 92 and the cooled CCD camera 91 is closed by a glass plate 105 and the periphery of the cooled CCD camera 91 is formed with heat dispersion fins 106 over substantially its entire length for dispersing heat.

A camera lens 107 disposed in the dark box 92 is mounted on the front surface of the glass plate 105 disposed in the cooled CCD camera 91.

Figure 19:
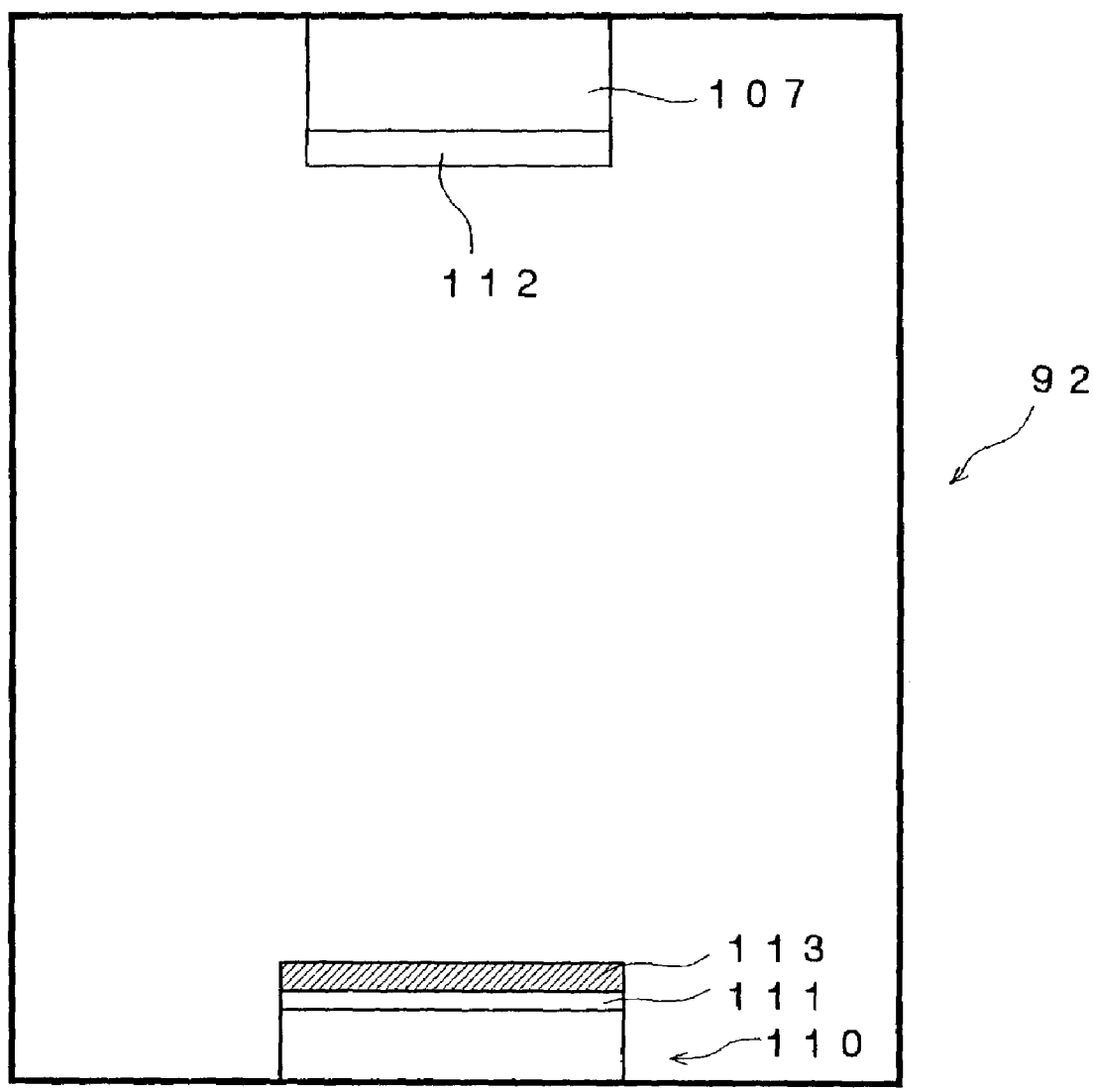
FIG. 19 is a schematic vertical cross sectional view showing a dark box of a data producing system.

FIG. 19 is a schematic vertical cross sectional view showing the dark box 92 of the data producing system.

As shown in FIG. 19, the dark box 92 is equipped with a light emitting diode stimulating ray source 110 for emitting a stimulating ray. The light emitting diode stimulating ray source 110 is provided with a filter 111 detachably mounted thereon and a diffusion plate 113 mounted on the upper surface of the filter 111. The stimulating ray is emitted via the diffusion plate 113 toward a biochemical analysis unit (not shown) placed on the diffusion plate 113 so as to ensure that the biochemical analysis unit can be uniformly irradiated with the stimulating ray. The filter 111 has a property of cutting light components having a wavelength not close to that of the stimulating ray and harmful to the stimulation of a fluorescent substance and transmitting through only light components having a wavelength in the vicinity of that of the stimulating ray. A filter 112 for cutting light components having a wavelength in the vicinity of that of the stimulating ray is detachably provided on the front surface of the camera lens 107.

Figure 20:
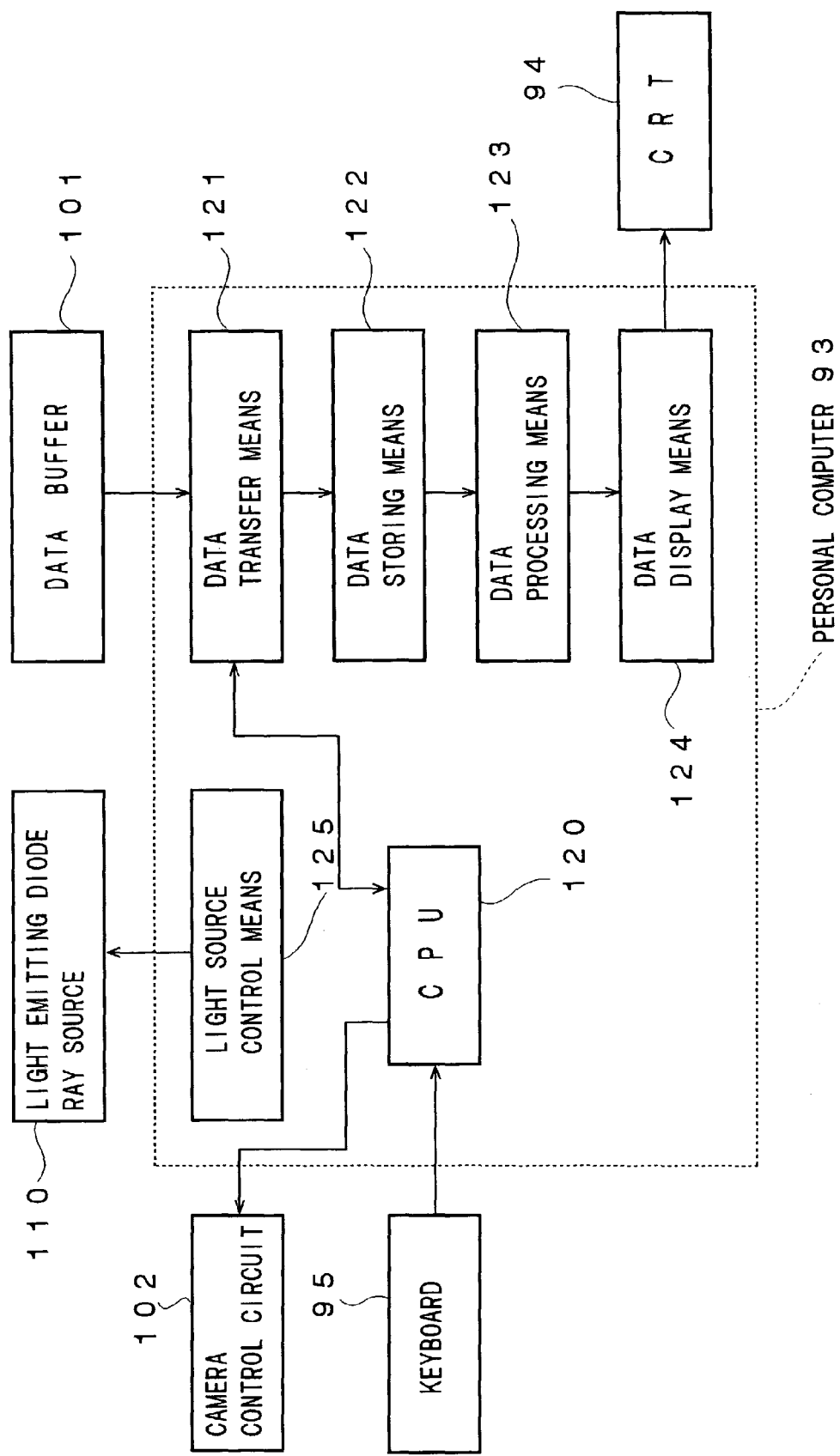
FIG. 20 is a block diagram of a personal computer of a data producing system and peripheral devices thereof.

FIG. 20 is a block diagram of the personal computer 93 of the data producing system and peripheral devices thereof.

As shown in FIG. 20, the personal computer 93 includes a CPU 120 for controlling the exposure of the cooled CCD camera 91, a data transferring means 121 for reading the data produced by the cooled CCD camera 91 from the data buffer 101, a storing means 122 for storing data, a data processing means 123 for effecting data processing on the digital data stored in the data storing means 122, and a data displaying means 124 for displaying visual data on the screen of the CRT 94 based on the digital data stored in the data storing means 122. The light emitting diode stimulating ray source 110 is controlled by a light source control means 125 and an instruction signal can be input via the CPU 120 to the light source control means 125 through the keyboard 85. The CPU 120 is constituted so as to output various signals to the camera controlling circuit 103 of the cooled CCD camera 91.

The data producing system shown in FIGS. 17 to 20 is constituted so as to detect chemiluminescence emission generated by the contact of a labeling substance contained in a number of the absorptive regions 4 formed in the substrate 2 of the biochemical analysis unit 1 and a chemiluminescent substrate, with the CCD 96 of the cooled CCD camera 91 through the camera lens 107, thereby reading chemiluminescence data to produce biochemical analysis data, and irradiate the biochemical analysis unit 1 with a stimulating ray emitted from the light emitting diode stimulating ray source 110 and detect fluorescence emission released from a fluorescent substance such as a fluorescent dye contained in a number of the absorptive regions 4 formed in the substrate 2 of the biochemical analysis unit 1 upon being stimulated, with the CCD 96 of the cooled CCD camera 91 through a camera lens 107, thereby reading fluorescence data to produce biochemical analysis data.

When biochemical analysis data are to be produced by reading chemiluminescence data, the filter 112 is removed and while the light emitting diode stimulating ray source 110 is kept off, the biochemical analysis unit 1 is placed on the diffusion plate 113. At this time, the biochemical analysis unit 1 is releasing chemiluminescence emission as a result of contact of a labeling substance contained in a number of the absorptive regions 4 formed in the substrate 2 of the biochemical analysis unit 1 and a chemiluminescent substrate.

The lens focus is then adjusted by the user using the camera lens 107 and the dark box 92 is closed.

When an exposure start signal is input by the user through the keyboard 95, the exposure start signal is input through the CPU 120 to the camera control circuit 102 of the cooled CCD camera 91 so that the shutter 99 is opened by the camera control circuit 102, whereby the exposure of the CCD 96 is started.

Chemiluminescence emission released from a number of the absorptive regions 4 of the biochemical analysis unit 1 impinges on the light receiving surface of the CCD 96 of the cooled CCD camera 91 via the camera lens 107, thereby forming an image on the light receiving surface. The CCD 96 receives light of the thus formed image and accumulates it in the form of electric charges therein.

In this embodiment, since the substrate 2 made of aluminum and capable of attenuating light energy are present around each of the absorptive regions 4 formed in the biochemical analysis unit 1, it is possible to reliably prevent chemiluminescence emission released from the labeling substance contained in each of the absorptive regions 4 from being mixed with chemiluminescence emission released from a labeling substance contained in the neighboring absorptive regions 4.

When a predetermined exposure time has passed, the CPU 120 outputs an exposure completion signal to the camera control circuit 102 of the cooled CCD camera 91.

When the camera controlling circuit 102 receives the exposure completion signal from the CPU 120, it transfers analog data accumulated in the CCD 96 in the form of electric charge to the A/D converter 100 to cause the A/D converter 100 to digitize the data and to temporarily store the thus digitized data in the data buffer 101.

At the same time, the CPU 120 outputs a data transfer signal to the data transferring means 121 to cause it to read out the digital data from the data buffer 101 of the cooled CCD camera 91 and to input them to the data storing means 122.

When the user inputs a data producing signal through the keyboard 95, the CPU 120 outputs the digital data stored in the data storing means 122 to the data processing means 123 and causes the data processing means 123 to effect data processing on the digital data in accordance with the user's instructions. The CPU 120 then outputs a data display signal to the displaying means 124 and causes the displaying means 124 to display biochemical analysis data on the screen of the CRT 94 based on the thus processed digital data.

On the other hand, when biochemical analysis data are to be produced by reading fluorescence data, the biochemical analysis unit 1 is first placed on the diffusion plate 113.

The light emitting diode stimulating ray source 110 is then turned on by the user and the lens focus is adjusted using the camera lens 107. The dark box 92 is then closed.

When the user inputs an exposure start signal through the keyboard 95, the light emitting diode stimulating ray source 110 is again turned on by the light source control means 125, thereby emitting a stimulating ray toward the biochemical analysis unit 1.

At the same time, the exposure start signal is input via the CPU 120 to the camera control circuit 102 of the cooled CCD camera 91 and the shutter 99 is opened by the camera control circuit 102, whereby the exposure of the CCD 96 is started.

The stimulating ray emitted from the light emitting diode stimulating ray source 110 passes through the filter 111, whereby light components of wavelengths not in the vicinity of that of the stimulating ray are cut. The stimulating ray then passes through the diffusion plate 113 to be made uniform light and the biochemical analysis unit 1 is irradiated with the uniform stimulating ray.

When the biochemical analysis unit 1 is irradiated with the stimulating ray, a fluorescent substance such as a fluorescent dye contained in a number of the absorptive regions 4 of the biochemical analysis unit 1 is stimulated by the stimulating ray, thereby releasing fluorescence emission from a number of the absorptive regions 4 of the biochemical analysis unit 1.

The fluorescence emission released from a number of the absorptive regions 4 of the biochemical analysis unit 1 impinges on the light receiving surface of the CCD 96 of the cooled CCD camera 91 through the filter 112 and the camera lens 107 and forms an image thereon. The CCD 96 receives light of the thus formed image and accumulates it in the form of electric charges therein. Since light components of wavelength equal to the stimulating ray wavelength are cut by the filter 112, only fluorescence emission released from the fluorescent substance such as a fluorescent dye contained in a number of the absorptive regions 4 of the biochemical analysis unit 1 is received by the CCD 96.

In this embodiment, since the substrate 2 made of aluminum and capable of attenuating light energy are present around each of the absorptive regions 4 formed in the biochemical analysis unit 1, it is possible to reliably prevent fluorescence emission released from a fluorescent substance contained in each of the absorptive regions 4 from being mixed with fluorescence emission released from a fluorescent substance contained in the neighboring absorptive regions 4.

When a predetermined exposure time has passed, the CPU 120 outputs an exposure completion signal to the camera control circuit 102 of the cooled CCD camera 91.

When the camera controlling circuit 102 receives the exposure completion signal from the CPU 120, it transfers analog data accumulated in the CCD 96 in the form of electric charge to the A/D converter 100 to cause the AID converter 100 to digitize the data and to temporarily store the thus digitized data in the data buffer 101.

At the same time, the CPU 120 outputs a data transfer signal to the data transferring means 121 to cause it to read out the digital data from the data buffer 101 of the cooled CCD camera 91 and to input them to the data storing means 122.

When the user inputs a data producing signal through the keyboard 95, the CPU 120 outputs the digital data stored in the data storing means 122 to the data processing apparatus 123 and causes the data processing apparatus 123 to effect data processing on the digital data in accordance with the user's instructions. The CPU 120 then outputs a data display signal to the displaying means 124 and causes the displaying means 124 to display biochemical analysis data on the screen of the CRT 94 based on the thus processed digital data.

When the production of biochemical analysis data has been completed in this manner, the biochemical analysis unit 1 is washed.

In this embodiment, the electric field generating device 10 provided with the electrodes 9aa, 9ab, 9ac, . . . , 9am, . . . , 9nm at positions corresponding to those of the absorptive regions 4 formed in the biochemical analysis unit 1 is moved to the electric field applying position and the electrodes 9aa, 9ab, 9ac, . . . , 9am, . . . , 9nm are inserted into the corresponding absorptive regions 4 of the biochemical analysis unit 1. While the field generating device is so positioned, the switching operation of the switches 16aa, 16ab, 16ac, . . . , 16am, . . . , 16nm is controlled so that the electrodes 9aa, 9ab, 9ac, . . . , 9am, . . . , 9nm provided in the electric field generating device 10 are sequentially connected to the positive power source 11 one at a time and that the other electrodes are connected to the ground terminal 12 and a positive voltage is applied to only one of the electrodes 9aa, 9ab, 9ac, . . . , 9am, . . . , 9nm from the positive power source 11. As a result, a substance derived from a living organism and contained in the reaction solution 19 is selectively attracted to the electrode applied with a positive voltage and the substance is forcibly brought into contact with a specific binding substance absorbed in the absorptive region 4 of the biochemical analysis unit 1 into which the electrode applied with a positive voltage is inserted to hybridize it with the specific binding substance.

Therefore, according to this embodiment, it is possible to markedly improve the efficiency of hybridization and since it is possible to markedly increase the possibility of association of a substance derived from a living organism and contained in the reaction solution 19 with a specific binding substance as a target absorbed in the absorptive region 4 of the biochemical analysis unit 1 into which the electrode applied with a positive voltage is inserted, it is possible to selectively hybridize in a desired manner the substance derived from a living organism and contained in the reaction solution 19 with the specific binding substance absorbed in the absorptive region 4 of the biochemical analysis unit 1 into which the electrode applied with a positive voltage is inserted.

Moreover, according to this embodiment, since a positive voltage is sequentially applied from the positive power source 11 to the electrodes 9aa, 9ab, 9ac, . . . , 9am, . . . , 9nm one at a time and the positive power source 11 is turned off when a predetermined time period has passed, a substance derived from a living organism which was attracted to the absorptive region 4 of the biochemical analysis unit 1 into which the electrode applied with a positive voltage is inserted but was nevertheless not hybridized with a specific binding substance absorbed in the absorptive region 4 leaves the absorptive region 4 to be returned to the reaction solution 19 when the positive power source 11 is turned off and is attracted to an electrode next applied with a positive voltage from the positive power source 11. Therefore, since the substance derived from a living organism is moved in the reaction solution 19 in response to the on and off operation of the positive power source 11 similarly to the case where the reaction solution 19 is agitated, it is possible to markedly increase the possibility of association of the substance derived from a living organism and contained in the reaction solution 19 with specific binding substances as a target contained in a number of the absorptive regions 4 of the biochemical analysis unit 1.

Furthermore, according this embodiment, the switching operation of the switches 16aa, 16ab, 16ac, . . . , 16am, . . . , 16nm is controlled so that the electrodes 9aa, 9ab, 9ac, . . . , 9am, . . . , 9nm provided in the electric field generating device 10 are sequentially connected to the positive power source 11 one at a time and that other electrodes are connected to the ground terminal 12 and a positive voltage is applied to only one of the electrodes 9aa, 9ab, 9ac, . . . , 9am, . . . , 9nm from the positive power source 11. As a result, an antibody to the hapten labeled with an enzyme which generates chemiluminescence emission when it contacts a chemiluminescent substrate and contained in the reaction solution 19 is selectively attracted to only the electrode applied with a positive voltage and is forcibly brought into contact with a hapten labeling a substance derived from a living organism and selectively hybridized with a specific biding substance absorbed in the absorptive region 4 of the biochemical analysis unit 1 into which the electrode applied with a positive voltage is inserted, thereby being bound with the hapten by an antigen-antibody reaction. Therefore, it is possible to markedly improve the efficiency of an antigen-antibody reaction and since it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with a specific biding substance absorbed in the absorptive region 4 of the biochemical analysis unit 1 into which the electrode applied with a positive voltage is inserted, it is possible to bind an antibody to the hapten labeled with an enzyme which generates chemiluminescence emission when it contacts a chemiluminescent substrate and contained in the reaction solution 19 with a hapten labeling a substance derived from a living organism and selectively hybridized with a specific biding substance absorbed in the absorptive region 4 of the biochemical analysis unit 1 into which the electrode applied with a positive voltage is inserted by an antigen-antibody reaction in a desired manner.

Moreover, according to this embodiment, since a positive voltage is sequentially applied from the positive power source 11 to the electrodes 9aa, 9ab, 9ac, . . . , 9am, . . . , 9nm one at a time and the positive power source 11 is turned off when a predetermined time period has passed, an antibody to the hapten labeled with an enzyme which generates chemiluminescence emission when it contacts a chemiluminescent substrate which was attracted to the absorptive region 4 of the biochemical analysis unit 1 into which the electrode applied with a positive voltage is inserted but nevertheless did not bind with a hapten labeling a substance derived from a living organism and selectively hybridized with a specific binding substance absorbed in the absorptive region 4 leaves the absorptive region 4 to be returned to the reaction solution 19 when the positive power source 11 is turned off and is attracted to an electrode next applied with a positive voltage from the positive power source 11. Therefore, since an antibody to the hapten labeled with an enzyme which generates chemiluminescence emission when it contacts a chemiluminescent substrate is moved in the reaction solution 19 in response to the on and off operation of the positive power source 11 similarly to the case where the reaction solution 19 is agitated, it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with a specific biding substance absorbed in the absorptive region 4 of the biochemical analysis unit 1 into which the electrode applied with a positive voltage is inserted.

Figure 21:
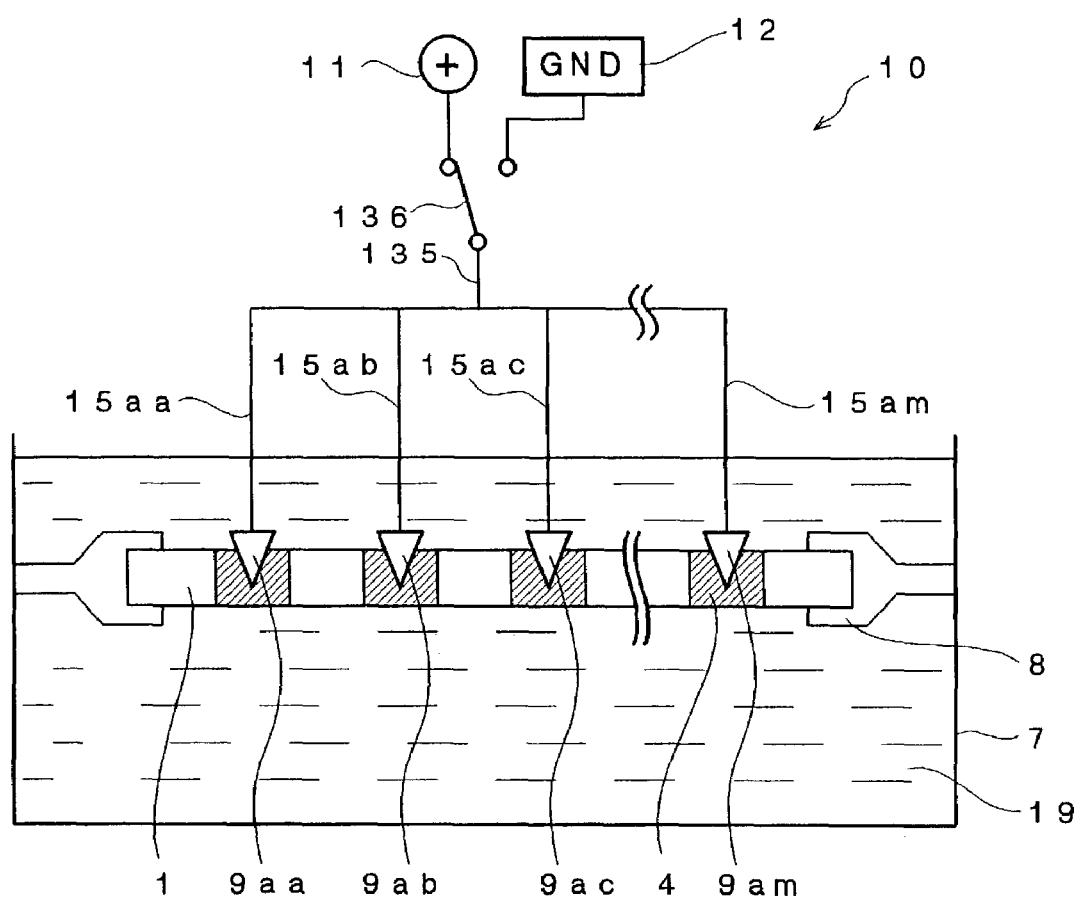
FIG. 21 is a schematic cross-sectional view showing an apparatus for conducting a receptor-ligand association reaction which is another preferred embodiment of the present invention.
Figure 22:
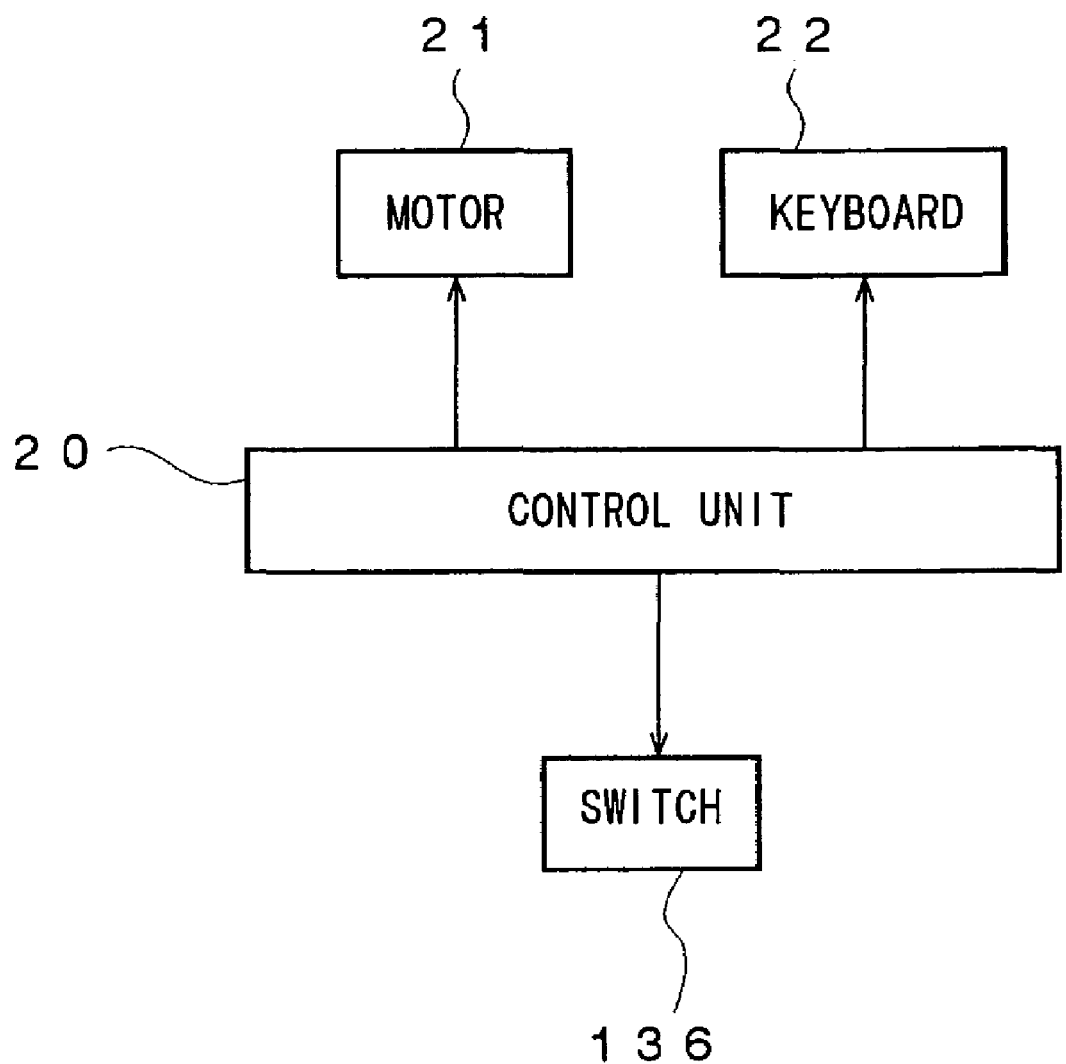
FIG. 22 is a block diagram of a control system, a drive system and an input system of an apparatus for conducting a receptor-ligand association reaction which is another preferred embodiment of the present invention.

FIG. 21 is a schematic cross-sectional view showing an apparatus for conducting a receptor-ligand association reaction which is another preferred embodiment of the present invention and FIG. 22 is a block diagram of a control system, a drive system and an input system of the apparatus for conducting a receptor-ligand association reaction.

Similarly to the apparatus for conducting a receptor-ligand association reaction shown in FIGS. 3 to 5, the apparatus for conducting a receptor-ligand association reaction according to this embodiment also includes an electric field generating device 10 provided with m×n electrodes 9aa, 9ab, 9ac, . . . , 9am, . . . , 9nm (nm=m×n), a positive power source 11 and a ground terminal 12.

As shown in FIG. 21, in the apparatus for conducting a receptor-ligand association reaction according to this embodiment, electric conductors 15aa, 15ab, 15ac, . . . , 15am, . . . , 15nm connected to the electrodes 9aa, 9ab, 9ac, . . . , 9am, . . . , 9nm incorporated in the electric field generating device 10 are connected to an electric conductor 135 and a switch 136 is provided in the electric conductor 135 for selectively connecting the positive power source 11 or the ground terminal 12 to the electrodes 9aa, 9ab, 9ac, . . . , 9am, . . . , 9nm so that the electrodes 9aa, 9ab, 9ac, . . . , 9am, . . . , 9nm can be simultaneously connected to the positive power source 11 or the ground terminal 12.

Therefore, as shown in FIG. 22, the control unit 20 is constituted so as to control only the switching operation of the switch 136 instead of the switches 16aa, 16ab, 16ac, . . . , 16am, . . . , 16nm.

In the thus constituted apparatus for conducting receptor-ligand association according to this embodiment, a substance derived from a living organism and labeled with a labeling substance is selectively hybridized with specific binding substances absorbed in a number of the absorptive regions 4 of the biochemical analysis unit 1 in the following manner.

While the electric field generating device 10 is held at the retracted position, the biochemical analysis unit 1 formed with a number of the absorptive regions 4 in which specific binding substances are absorbed is first set at the biochemical analysis unit holding section 8.

A reaction solution 19 is then prepared and accommodated in the reaction vessel 7.

In this embodiment, a reaction solution 19 containing a substance derived from a living organism and labeled with a radioactive labeling substance, a substance derived from a living organism and labeled with a hapten such as digoxigenin and a substance derived from a living organism and labeled with a fluorescent substance such as a fluorescent dye is prepared and accommodated in the reaction vessel 7.

When the reaction solution 19 is prepared and accommodated in the reaction vessel 7, a start signal is input by a user through the keyboard 22.

The start signal is output to the control unit 20 and when the control unit 20 receives the start signal, it outputs a drive signal to the motor 21, thereby causing it to move the electric field generating device 10 from the retracted position to the electric field applying position.

As a result, the cone-like electrodes $9aa$, $9ab$, $9ac$, ..., $9am$, ..., $9nm$ formed in the electric field generating device 10 at positions corresponding to a number of the absorptive regions 4 of the biochemical analysis unit 1 are inserted into the corresponding absorptive regions 4 of the biochemical analysis unit 1.

The control unit 20 then switches the switch 136 so that the electric conductor 135 is connected to the positive power source 11, thereby connecting the electrodes $9aa$, $9ab$, $9ac$, ..., $9am$, ..., $9nm$ to the positive power source 11.

When the switch 136 has been switched and the electrodes $9aa$, $9ab$, $9ac$, ..., $9am$, ..., $9nm$ have been connected to the positive power source 11, the control unit 20 turns the positive power source 11 on.

As a result, a positive voltage is simultaneously applied to the electrodes $9aa$, $9ab$, $9ac$, ..., $9am$, ..., $9nm$, thereby generating an electric field and a substance derived from a living organism and contained in the reaction solution 19 is attracted to the electrodes $9aa$, $9ab$, $9ac$, ..., $9am$, ..., $9nm$.

Since the electric field generating device 10 has been moved to the electric field applying position and the electrodes $9aa$, $9ab$, $9ac$, ..., $9am$, ..., $9nm$ are inserted into the corresponding absorptive region 4 of the biochemical analysis unit 1, a substance derived from a living organism and contained in the reaction solution 19 is forcibly brought into contact with specific binding substances absorbed in the absorptive regions 4 of the biochemical analysis unit 1 into which the electrodes $9aa$, $9ab$, $9ac$, ..., $9am$, ..., $9nm$ applied with a positive voltage are inserted and selectively hybridized with the specific binding substances.

Therefore, it is possible to markedly improve the efficiency of hybridization and since it is possible to markedly increase the possibility of association of the substance derived from a living organism and contained in the reaction solution 19 with the specific binding substances as a target absorbed in the absorptive regions 4 of the biochemical analysis unit 1 into which the electrodes $9aa$, $9ab$, $9ac$, ..., $9am$, ..., $9nm$ are inserted, it is possible to selectively hybridize in a desired manner the substance derived from a living organism and contained in the reaction solution 19 with the specific binding substances absorbed in the absorptive regions 4 of the biochemical analysis unit 1 into which the electrodes $9aa$, $9ab$, $9ac$, ..., $9am$, ..., $9nm$ are inserted.

When a predetermined time period has passed, the control unit 20 turns the positive power source 11 off and switches the switch 136 so that the electric conductor 135 is connected to the ground terminal 12.

As a result, a substance derived from a living organism and contained in the reaction solution 19 is no longer attracted to the electrodes $9aa$, $9ab$, $9ac$, ..., $9am$, ..., $9nm$ and a substance derived from a living organism which was not hybridized with specific binding substances contained in the absorptive regions 4 of the biochemical analysis unit 1 leaves the absorptive regions 4.

In this manner, a substance derived from a living organism and contained in the reaction solution 19 can be selectively hybridized with specific binding substances contained in the absorptive regions 4 of the biochemical analysis unit 1 by repeating, as occasion demands, the steps of connecting the electrodes $9aa$, $9ab$, $9ac$, ..., $9am$, ..., $9nm$ to the positive power source 11, disconnecting the electrodes $9aa$, $9ab$, $9ac$, ..., $9am$, ..., $9nm$ from the positive power source 11 and connecting the electrodes $9aa$, $9ab$, $9ac$, ..., $9am$, ..., $9nm$ to the ground terminal 12.

When hybridization has been completed, the control unit 20 outputs a drive signal to the motor 21, thereby causing it to move the electric field generating device 10 from the electric field applying position to the retracted position.

In this manner, radiation data of a radioactive labeling substance and a fluorescence data of a fluorescent substance such as a fluorescent dye are recorded in a number of the absorptive regions 4 formed in the substrate 2 of the biochemical analysis unit 1.

Similarly to the previous embodiment, the fluorescence data recorded in a number of the absorptive regions 4 of the biochemical analysis unit 1 are read by the scanner shown in FIG. 9 and biochemical analysis data are produced.

On the other hand, the radiation data recorded in a number of the absorptive regions 4 of the biochemical analysis unit 1 are transferred into a number of the stimulable phosphor layer regions 27 in the stimulable phosphor sheet 25 shown in FIG. 7 and the radiation data transferred to a number of the stimulable phosphor layer regions 27 in the stimulable phosphor sheet 25 are read by the scanner shown in FIG. 9 similarly to the previous embodiment, whereby biochemical analysis data are produced.

To the contrary, in order to record chemiluminescence data in a number of the absorptive regions 4 formed in the substrate 2 of the biochemical analysis unit 1, a reaction solution 19 containing an antibody to the hapten such as digoxigenin labeled with an enzyme which generates chemiluminescence emission when it contacts a chemiluminescent substrate is further prepared and accommodated in the reaction vessel 7 and the antibody to the hapten such as digoxigenin labeled with an enzyme which generates chemiluminescence emission when it contacts a chemiluminescent substrate is bound with the hapten such as digoxigenin labeling a substance derived from a living organism selectively hybridized with specific binding substances absorbed in a number of the absorptive regions 4 formed in the substrate 2 of the biochemical analysis unit 1 by the an antigen-antibody reaction.

Specifically, a reaction solution 19 containing an antibody to the hapten such as digoxigenin labeled with an enzyme which generates chemiluminescence emission when it contacts a chemiluminescent substrate is first prepared and accommodated in the reaction vessel 7.

When the reaction solution 19 is prepared and accommodated in the reaction vessel 7, a start signal is input by a user through the keyboard 22.

The start signal is output to the control unit 20 and when the control unit 20 receives the start signal, it outputs a drive signal to the motor 21, thereby causing it to move the electric field generating device 10 from the retracted position to the electric field applying position. As a result, the cone-like electrodes 9aa, 9ab, 9ac, . . . , 9am, . . . , 9nm formed in the electric field generating device 10 at positions corresponding to a number of the absorptive regions 4 of the biochemical analysis unit 1 are inserted into the corresponding absorptive regions 4 of the biochemical analysis unit 1. The control unit 20 then switches the switch 136 so that the electric conductor 135 is connected to the positive power source 11, thereby connecting the electrodes 9aa, 9ab, 9ac, . . . , 9am, . . . , 9nm to the positive power source 11.

When the switch 136 has been switched and the electrodes 9aa, 9ab, 9ac, . . . , 9am, . . . , 9nm have been connected to the positive power source 11, the control unit 20 turns the positive power source 11 on.

As a result, a positive voltage is simultaneously applied to the electrodes 9aa, 9ab, 9ac, . . . , 9am, . . . , 9nm, thereby generating an electric field and an antibody to the hapten labeled with an enzyme which generates chemiluminescence emission when it contacts a chemiluminescent substrate and contained in the reaction solution 19 is attracted to the electrodes 9aa, 9ab, 9ac, . . . , 9am, . . . , 9nm.

Since the electric field generating device 10 has been moved to the electric field applying position and the electrodes 9aa, 9ab, 9ac, . . . , 9am, . . . , 9nm are inserted into the corresponding absorptive region 4 of the biochemical analysis unit 1, an antibody to the hapten labeled with an enzyme which generates chemiluminescence emission when it contacts a chemiluminescent substrate and contained in the reaction solution 19 is forcibly brought into contact with a hapten labeling a substance derived from a living organism and selectively hybridized with specific biding substances absorbed in the absorptive regions 4 of the biochemical analysis unit 1 into which the electrodes 9aa, 9ab, 9ac, . . . , 9am, . . . , 9nm applied with a positive voltage are inserted and selectively hybridized with the specific binding substances.

Therefore, it is possible to markedly improve the efficiency of a receptor-ligand association reaction and since it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with specific biding substances absorbed in the absorptive regions 4 of the biochemical analysis unit 1 into which the electrodes 9aa, 9ab, 9ac, . . . , 9am, . . . , 9nm are inserted, it is possible to bind by an antigen-antibody reaction in a desired manner with an antibody to the hapten labeled with an enzyme which generates chemiluminescence emission when it contacts a chemiluminescent substrate and contained in the reaction solution 19 with a hapten labeling a substance derived from a living organism and selectively hybridized with specific biding substances absorbed in the absorptive regions 4 of the biochemical analysis unit 1 into which the electrodes 9aa, 9ab, 9ac, . . . , 9am, . . . , 9nm are inserted.

When a predetermined time period has passed, the control unit 20 turns the positive power source 11 off and switches the switch 136 so that the electric conductor 135 is connected to the ground terminal 12.

As a result, an antibody to the hapten labeled with an enzyme which generates chemiluminescence emission when it contacts a chemiluminescent substrate and contained in the reaction solution 19 is no longer attracted to the electrodes 9aa, 9ab, 9ac, . . . , 9am, . . . , 9nm and the antibody to the hapten labeled with an enzyme which did not bind by an antigen-antibody reaction with a hapten labeling a substance derived from a living organism and selectively hybridized with specific biding substances absorbed in the absorptive regions 4 of the biochemical analysis unit 1 leaves the absorptive regions 4.

In this manner, an antibody to the hapten labeled with an enzyme which generates chemiluminescence emission when it contacts a chemiluminescent substrate and contained in the reaction solution 19 can be bound by an antigen-antibody reaction with a hapten labeling a substance derived from a living organism and selectively hybridized with specific biding substances absorbed in the absorptive regions 4 of the biochemical analysis unit 1 by repeating, as occasion demands, the steps of connecting the electrodes 9aa, 9ab, 9ac, . . . , 9am, . . . , 9nm to the positive power source 11, disconnecting the electrodes 9aa, 9ab, 9ac, . . . , 9am, . . . , 9nm to the positive power source 11 and connecting the electrodes 9aa, 9ab, 9ac, . . . , 9am, . . . , 9nm to the ground terminal 12.

Thus, chemiluminescent data are recorded in a number of the absorptive regions 4 of the biochemical analysis unit 1.

Similarly to the previous embodiment, the chemiluminescent data recorded in a number of the absorptive regions 4 of the biochemical analysis unit 1 by the cooled CCD camera 91 of the data producing system shown in FIGS. 17 to 20 and biochemical analysis data are produced.

According to this embodiment, while the electric field generating device 10 provided with the electrodes 9aa, 9ab, 9ac, . . . , 9am, . . . , 9nm at positions corresponding to those of the absorptive regions 4 formed in the biochemical analysis unit 1 is moved to the electric field applying position and the electrodes 9aa, 9ab, 9ac, . . . , 9am, . . . , 9nm are inserted into the corresponding absorptive regions 4 of the biochemical analysis unit 1, a positive voltage is simultaneously applied to the electrodes 9aa, 9ab, 9ac, . . . , 9am, . . . , 9nm so that a substance derived from a living organism and contained in the reaction solution 19 is attracted to each of the electrodes 9aa, 9ab, 9ac, . . . , 9am, . . . , 9nm and forcibly brought into contact with specific binding substances absorbed in the absorptive regions 4 of the biochemical analysis unit 1 into which the electrodes 9aa, 9ab, 9ac, . . . , 9am, . . . , 9nm are inserted, thereby hybridizing a substance derived from a living organism with specific binding substances. Therefore, it is possible to markedly improve the efficiency of hybridization and since it is possible to markedly increase the possibility of association of a substance derived from a living organism and contained in the reaction solution 19 with specific binding substances as a target contained in the absorptive regions 4 of the biochemical analysis unit 1 into which the electrodes 9aa, 9ab, 9ac, . . . , 9am, . . . , 9nm are inserted, it is possible to selectively hybridize in a desired manner the substance derived from a living organism and contained in the reaction solution 19 with the specific binding substance absorbed in the absorptive region 4 of the biochemical analysis unit 1 into which the electrodes 9aa, 9ab, 9ac, . . . , 9am, . . . , 9nm are inserted.

Moreover, according to this embodiment, while the electric field generating device 10 provided with the electrodes 9aa, 9ab, 9ac, . . . , 9am, . . . , 9nm at positions corresponding to those of the absorptive regions 4 formed in the biochemical analysis unit 1 is moved to the electric field applying position and the electrodes 9aa, 9ab, 9ac, ..., 9am, ..., 9nm are inserted into the corresponding absorptive regions 4 of the biochemical analysis unit 1, a positive voltage is simultaneously applied to the electrodes 9aa, 9ab, 9ac, ..., 9am, ..., 9nm so that an antibody to the hapten labeled with an enzyme which generates chemiluminescence emission when it contacts a chemiluminescent substrate and contained in the reaction solution 19 is attracted to each of the electrodes 9aa, 9ab, 9ac, ..., 9am, ..., 9nm and forcibly brought into contact with a hapten labeling a substance derived from a living organism and selectively hybridized with specific biding substances absorbed in the absorptive regions 4 of the biochemical analysis unit 1 into which the electrodes 9aa, 9ab, 9ac, ..., 9am, ..., 9nm are inserted, thereby binding an antibody to the hapten labeled with an enzyme with the hapten labeling a substance derived from a living organism and selectively hybridized with specific biding substances absorbed in the absorptive regions 4 of the biochemical analysis unit 1. Therefore, it is possible to markedly improve the efficiency of an antigen-antibody reaction and since it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with specific binding substances absorbed in the absorptive regions 4 of the biochemical analysis unit 1 into which the electrodes 9aa, 9ab, 9ac, ..., 9am, ..., 9nm are inserted, it is possible to bind by an antigen-antibody reaction in a desired manner an antibody to the hapten labeled with an enzyme which generates chemiluminescence emission when it contacts a chemiluminescent substrate and contained in the reaction solution 19 with a hapten labeling a substance derived from a living organism and selectively hybridized with specific binding substances absorbed in the absorptive regions 4 of the biochemical analysis unit 1 into which the electrodes 9aa, 9ab, 9ac, ..., 9am, ..., 9nm are inserted.

Figure 23:
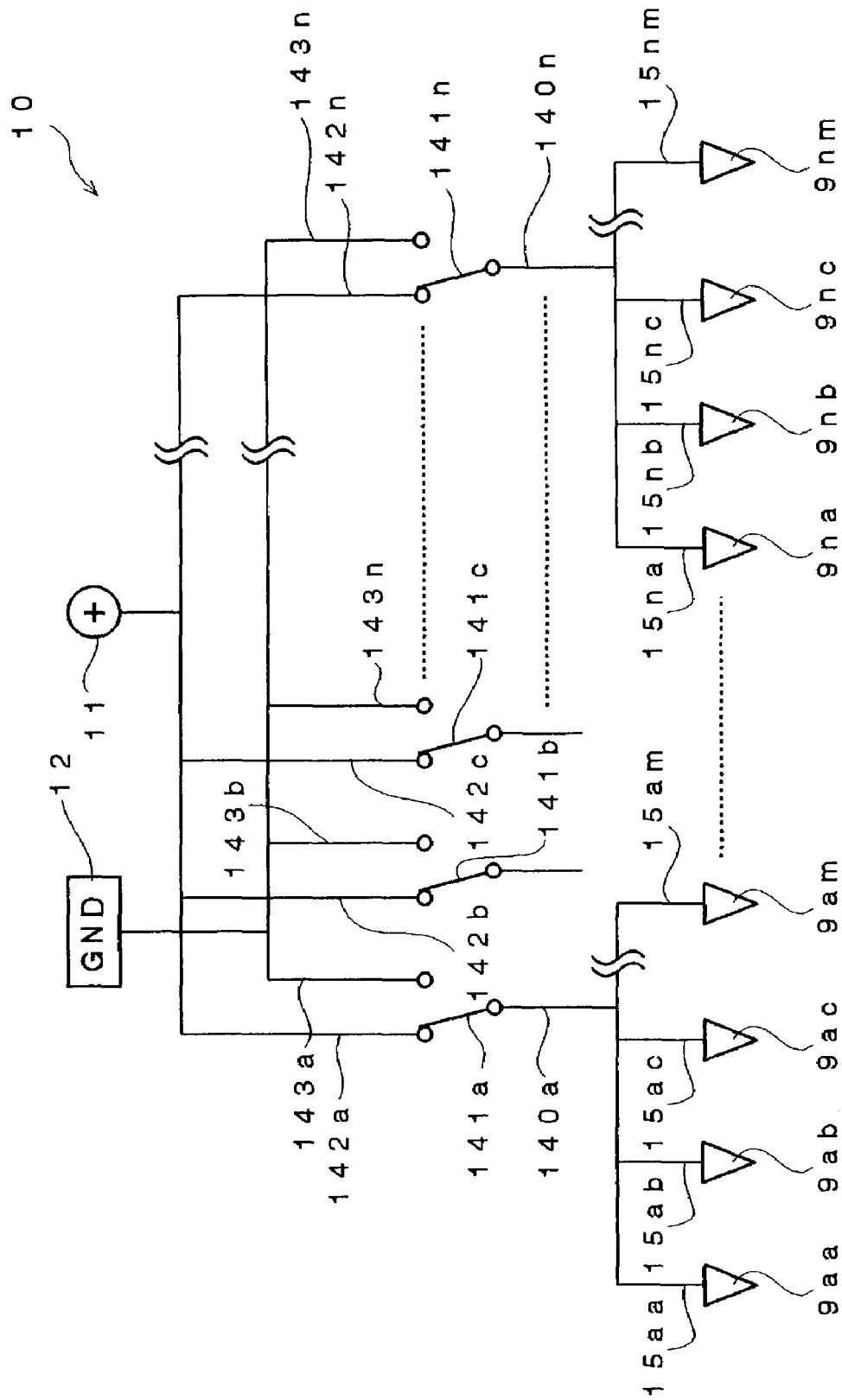
FIG. 23 is a connection wire diagram showing connection of electrodes, a positive power source and a ground terminal provided in an apparatus for conducting a receptor-ligand association reaction which is a further preferred embodiment of the present invention.
Figure 24:
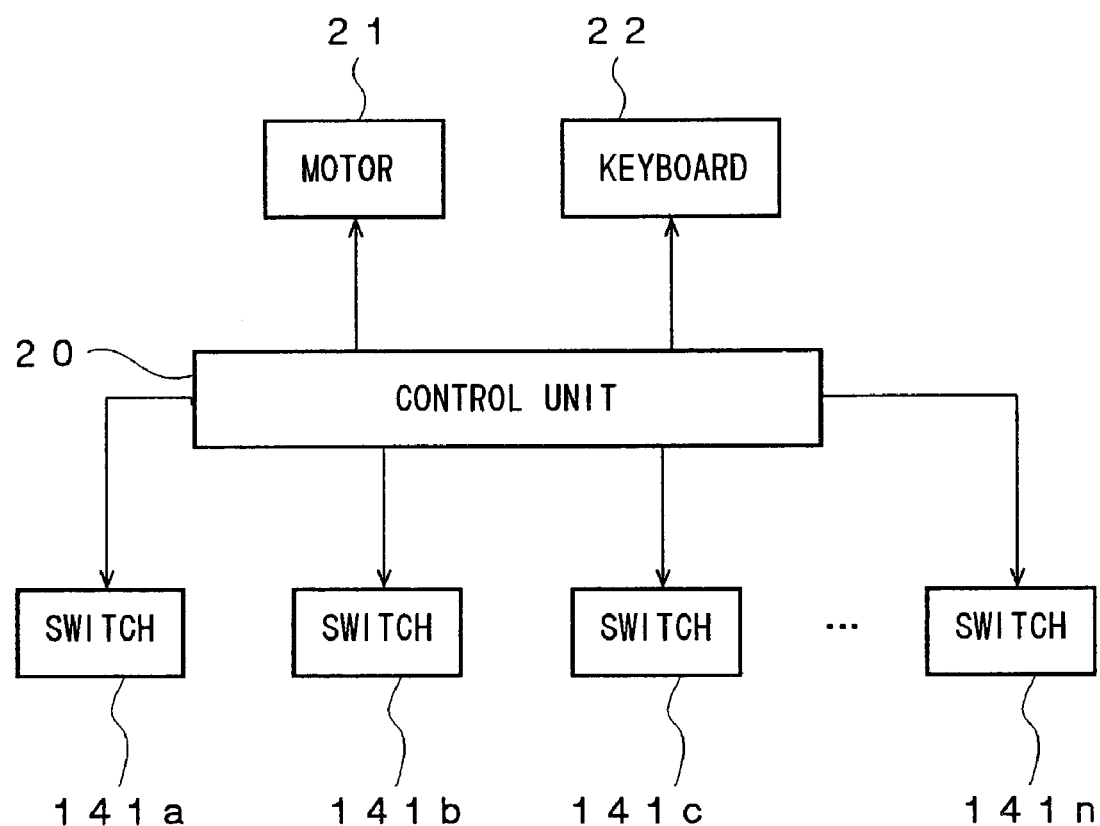
FIG. 24 is a block diagram of a control system, a drive system and an input system of an apparatus for conducting a receptor-ligand association reaction which is a further preferred embodiment of the present invention.

FIG. 23 is a connection wire diagram showing connection of electrodes, a positive power source and a ground terminal provided in an apparatus for conducting a receptor-ligand association reaction which is a further preferred embodiment of the present invention and FIG. 24 is a block diagram of a control system, a drive system and an input system of the apparatus for conducting a receptor-ligand association reaction.

Similarly to the apparatus for conducting a receptor-ligand association reaction shown in FIGS. 3 to 5, the apparatus for conducting a receptor-ligand association reaction according to this embodiment also includes an electric field generating device 10 provided with m×n electrodes 9aa, 9ab, 9ac, ..., 9am, ..., 9nm (nm=m×n), a positive power source 11 and a ground terminal 12.

As shown in FIG. 23, in the apparatus for conducting a receptor-ligand association reaction according to this embodiment, electric conductors 15aa, 15ab, 15ac, ..., 15am, ..., 15nm connected to the respective electrodes 9aa, 9ab, 9ac, ..., 9am, ..., 9na, 9nb, 9nc, ..., 9nm constituting electrode columns of the electric field generating device 10 are connected to electric conductors 140a, 140b, 140c, ..., 140n and switches 141a, 141b, 141c, ..., 141n are connected to the electric conductors 140b, 140c, ..., 140n so that the respective electrodes 9aa, 9ab, 9ac, ..., 9am, ..., 9na, 9nb, 9nc, ..., 9nm constituting electrode columns of the electric field generating device 10 can be selectively connected by switching the switches 141a, 141b, 141c, ..., 141n to electric conductors 142a, 142b, 142c, ..., 142n connected to the positive power source 11 or electric conductors 143a, 143b, 143c, ..., 143n connected to the ground terminal 12.

Therefore, as shown in FIG. 24, the control unit 20 is constituted so as to control the switching operation of the switches 141a, 141b, 141c, ..., 141n.

In the thus constituted apparatus for conducting receptor-ligand association according to this embodiment, a substance derived from a living organism and labeled with a labeling substance is selectively hybridized with specific binding substances absorbed in a number of the absorptive regions 4 of the biochemical analysis unit 1 in the following manner.

While the electric field generating device 10 is held at the retracted position, the biochemical analysis unit 1 formed with a number of the absorptive regions 4 in which specific binding substances are absorbed is first set at the biochemical analysis unit holding section 8.

A reaction solution 19 is then prepared and accommodated in the reaction vessel 7.

In this embodiment, a reaction solution 19 containing a substance derived from a living organism and labeled with a radioactive labeling substance, a substance derived from a living organism and labeled with a hapten such as digoxigenin and a substance derived from a living organism and labeled with a fluorescent substance such as a fluorescent dye is prepared and accommodated in the reaction vessel 7.

When the reaction solution 19 is prepared and accommodated in the reaction vessel 7, a start signal is input by a user through the keyboard 22.

The start signal is output to the control unit 20 and when the control unit 20 receives the start signal, it outputs a drive signal to the motor 21, thereby causing it to move the electric field generating device 10 from the retracted position to the electric field applying position.

As a result, the cone-like electrodes 9aa, 9ab, 9ac, ..., 9am, ..., 9nm formed in the electric field generating device 10 at positions corresponding to a number of the absorptive regions 4 of the biochemical analysis unit 1 are inserted into the corresponding absorptive regions 4 of the biochemical analysis unit 1. The control unit 20 then switches the switch 141a so that the electric conductor 140a connected to 9aa, 9ab, 9ac, ..., 9am constituting a first electrode column can be connected to the electric conductor 142a connected to the positive power source 11 and switches the switches 141b, 141c, ..., 141n so that the electric conductors 140b, 140c, ..., 140n connected to the electrodes 9ba, 9bb, 9bc, ..., 9bm, ..., 9na, 9nb, 9nc, ..., 9nm, i.e., the electrodes other than the electrodes 9aa, 9ab, 9ac, ..., 9am constituting the first electrode column, can be connected to the electric conductors 143b, 143c, ..., 143n connected to the ground terminal 12.

When the switches 141a, 140b, 140c, ..., 140n have been switched so that the electrodes 9aa, 9ab, 9ac, ..., 9am constituting the first electrode column have been connected to the positive power source 11 and that the electrodes 9ba, 9bb, 9bc, ..., 9bm, ..., 9na, 9nb, 9nc, ..., 9nm, i.e., the electrodes other than the electrodes 9aa, 9ab, 9ac, ..., 9am constituting the first electrode column, have been connected to the ground terminal 12, the control unit 20 turns the positive power source 11 on.

As a result, a positive voltage is applied to the electrodes 9aa, 9ab, 9ac, ..., 9am constituting the first electrode column, thereby generating an electric field and a substance derived from a living organism and contained in the reaction solution 19 is attracted to the electrodes 9aa, 9ab, 9ac, ..., 9am constituting the first electrode column.

Since the electric field generating device 10 has been moved to the electric field applying position and the electrodes 9aa, 9ab, 9ac, ..., 9am in the first electrode column are inserted into the corresponding absorptive region 4 of the biochemical analysis unit 1, a substance derived from a living organism and contained in the reaction solution 19 is forcibly brought into contact with specific binding substances absorbed in the absorptive regions 4 of the biochemical analysis unit 1 into which the electrodes 9aa, 9ab, 9ac, ..., 9am in the first electrode column are inserted and selectively hybridized with the specific binding substances.

Therefore, it is possible to markedly improve the efficiency of hybridization and since it is possible to markedly increase the possibility of association of the substance derived from a living organism and contained in the reaction solution 19 with the specific binding substances as a target absorbed in the absorptive regions 4 of the biochemical analysis unit 1 into which the electrodes 9aa, 9ab, 9ac, ..., 9am in the first electrode column are inserted, it is possible to selectively hybridize in a desired manner the substance derived from a living organism and contained in the reaction solution 19 with the specific binding substances absorbed in the absorptive regions 4 of the biochemical analysis unit 1 into which the electrodes 9aa, 9ab, 9ac, ..., 9am in the first electrode column are inserted.

When a predetermined time period has passed, the control unit 20 turns the positive power source 11 off.

As a result, a substance derived from a living organism and contained in the reaction solution 19 which was attracted to the absorptive regions 4 of the biochemical analysis unit 1 into which the electrodes 9aa, 9ab, 9ac, ..., 9am, ..., 9nm in the first electrode column are inserted but was nevertheless not hybridized with specific binding substances contained in the absorptive regions 4 of the biochemical analysis unit 1 leaves the absorptive regions 4 into which the electrodes 9aa, 9ab, 9ac, ..., 9am in the first electrode column are inserted.

The control unit 20 then switches the switch 141b so that the electric conductor 140b connected to the electrodes 9ba, 9bb, 9bc, ..., 9bm constituting a second electrode column can be connected to the electric conductor 142b connected to the positive power source 11 and switches the switch 141a connected to the electrodes 9aa, 9ab, 9ac, ..., 9am constituting the first electrode column so that the electric conductor 140a connected to the electrodes 9aa, 9ab, 9ac, ..., 9am constituting the first electrode column can be connected to the electric conductor 143a connected the ground terminal 12, thereby connecting the electrodes 9aa, 9ab, 9ac, ..., 9am, ..., 9na, 9nb, 9nc, ..., 9nm, i.e., the electrodes other than the electrodes 9ba, 9bb, 9bc, ..., 9bm constituting the second electrode column, to the ground terminal 12.

When the switches 141a and 141b have been switched so that the electrodes 9ba, 9bb, 9bc, ..., 9bm constituting the second electrode column have been connected to the positive power source 11 and that the electrodes 9aa, 9ab, 9ac, ..., 9am, ..., 9na, 9nb, 9nc, ..., 9nm, i.e., the electrodes other than the electrodes 9ba, 9bb, 9bc, ..., 9bm in second electrode column, have been connected to the ground terminal 12, the control unit 20 turns the positive power source 11 on.

As a result, a positive voltage is applied to the electrodes 9ba, 9bb, 9bc, ..., 9bm constituting the second electrode column, thereby generating an electric field and a substance derived from a living organism and contained in the reaction solution 19 is attracted to the electrodes 9ba, 9bb, 9bc, ..., 9bm constituting the second electrode column, whereby a substance derived from a living organism and contained in the reaction solution 19 is forcibly brought into contact with specific binding substances absorbed in the absorptive regions 4 of the biochemical analysis unit 1 into which the electrodes 9ba, 9bb, 9bc, ..., 9bm in the second electrode column are inserted and selectively hybridized with the specific binding substances.

Therefore, it is possible to markedly improve the efficiency of hybridization and since it is possible to markedly increase the possibility of association of the substance derived from a living organism and contained in the reaction solution 19 with the specific binding substances as a target absorbed in the absorptive regions 4 of the biochemical analysis unit 1 into which the electrodes 9ba, 9bb, 9bc, ..., 9bm in the second electrode column are inserted, it is possible to selectively hybridize in a desired manner the substance derived from a living organism and contained in the reaction solution 19 with the specific binding substances absorbed in the absorptive regions 4 of the biochemical analysis unit 1 into which the electrodes 9ba, 9bb, 9bc, ..., 9bm in the second electrode column are inserted.

When a predetermined time period has passed, the control unit 20 turns the positive power source 11 off. Similarly to the above, the control unit 20 controls the switching operation of the switches 141a, 141b, 141c, ..., 141n so that each of a third electrode column to an nth electrode column can be sequentially connected to the positive power source 11 while other electrode columns can be connected to the ground terminal 12 and sequentially applies a positive voltage to electrodes of each of the electrode columns connected to the positive power source 11, thereby generating an electric field.

As a result, a substance derived from a living organism and contained in the reaction solution 19 is sequentially attracted to electrodes of each of the electrode columns and is forcibly brought into contact with specific binding substances absorbed in the absorptive regions 4 of the biochemical analysis unit 1 into which the electrodes of the electrode column are inserted, whereby a substance derived from a living organism and contained in the reaction solution 19 is selectively hybridized with the specific binding substances.

In this manner, according to this embodiment, the switching operation of the switches 141a, 141b, 141c, ..., 141n is controlled so that electrodes of each of the electrode columns can be sequentially connected to the positive power source 11 while other electrode columns can be connected to the ground terminal 12 and a positive voltage is sequentially applied to electrodes of each of the electrode columns connected to the positive power source 11, thereby selectively attracting a substance derived from a living organism and contained in the reaction solution 19 to the electrodes of the electrode column applied with a positive voltage and forcibly bringing it into contact with specific binding substances contained in the absorptive regions 4 of the biochemical analysis unit 1 into which the electrodes of the electrode column to be hybridized with the specific binding substances. Therefore, it is possible to markedly improve the efficiency of hybridization and since it is possible to markedly increase the possibility of association of the substance derived from a living organism and contained in the reaction solution 19 with the specific binding substances as a target absorbed in the absorptive regions 4 of the biochemical analysis unit 1 into which the electrodes of the electrode column applied with a positive voltage are inserted, it is possible to selectively hybridize in a desired manner the substance derived from a living organism and contained in the reaction solution 19 with the specific binding substances absorbed in the absorptive regions 4 of the biochemical analysis unit 1 into which the electrodes of the electrode column applied with a positive voltage are inserted.

Moreover, according to this embodiment, since a positive voltage is sequentially applied from the positive power source 11 to electrodes of each of the electrode columns and the positive power source 11 is turned off when a predetermined time period has passed, a substance derived from a living organism which was attracted to the absorptive regions 4 of the biochemical analysis unit 1 into which the electrodes of the electrode column applied with a positive voltage are inserted but was nevertheless not hybridized with specific binding substances contained in the absorptive regions 4 of the biochemical analysis unit 1 leaves the absorptive regions 4 when the positive power source 11 is turned off to be returned to the reaction solution 19 and is attracted to electrodes of an electrode column next applied with a positive voltage. Therefore, since a substance derived from a living organism are moved in the reaction solution 19 in response to the on and off operation of the positive power source 11 similarly to the case where the reaction solution 19 is agitated, it is possible to markedly increase the possibility of association of the substance derived from a living organism and contained in the reaction solution 19 with specific binding substances as a target contained in a number of the absorptive regions 4 of the biochemical analysis unit 1.

When hybridization has been completed, the control unit 20 outputs a drive signal to the motor 21, thereby causing it to move the electric field generating device 10 from the electric field applying position to the retracted position.

In this manner, radiation data of a radioactive labeling substance and a fluorescence data of a fluorescent substance such as a fluorescent dye are recorded in a number of the absorptive regions 4 formed in the substrate 2 of the biochemical analysis unit 1.

Similarly to the previous embodiments, the fluorescence data recorded in a number of the absorptive regions 4 of the biochemical analysis unit 1 are read by the scanner shown in FIG. 9 and biochemical analysis data are produced.

On the other hand, the radiation data recorded in a number of the absorptive regions 4 of the biochemical analysis unit 1 are transferred into a number of the stimulable phosphor layer regions 27 the stimulable phosphor sheet 25 shown in FIG. 7 and the radiation data into a number of the stimulable phosphor layer regions 27 the stimulable phosphor sheet 25 are read by the scanner shown in FIG. 9 similarly to the previous embodiment, whereby biochemical analysis data are produced.

To the contrary, in order to record chemiluminescence data in a number of the absorptive regions 4 formed in the substrate 2 of the biochemical analysis unit 1, a reaction solution 19 containing an antibody to the hapten such as digoxigenin labeled with an enzyme which generates chemiluminescence emission when it contacts a chemiluminescent substrate is further prepared and accommodated in the reaction vessel 7 and the antibody to the hapten such as digoxigenin labeled with an enzyme which generates chemiluminescence emission when it contacts a chemiluminescent substrate is bound with the hapten such as digoxigenin labeling a substance derived from a living organism selectively hybridized with specific binding substances absorbed in a number of the absorptive regions 4 formed in the substrate 2 of the biochemical analysis unit 1 by the an antigen-antibody reaction.

Specifically, a reaction solution 19 containing an antibody to the hapten such as digoxigenin labeled with an enzyme which generates chemiluminescence emission when it contacts a chemiluminescent substrate is first prepared and accommodated in the reaction vessel 7.

When the reaction solution 19 is prepared and accommodated in the reaction vessel 7, a start signal is input by a user through the keyboard 22.

The start signal is output to the control unit 20 and when the control unit 20 receives the start signal, it outputs a drive signal to the motor 21, thereby causing it to move the electric field generating device 10 from the retracted position to the electric field applying position.

As a result, the cone-like electrodes $9aa$, $9ab$, $9ac$, ..., $9am$, ..., $9nm$ formed in the electric field generating device 10 at positions corresponding to a number of the absorptive regions 4 of the biochemical analysis unit 1 are inserted into the corresponding absorptive regions 4 of the biochemical analysis unit 1.

The control unit 20 then switches the switch $141a$ so that the electric conductor $140a$ connected to $9aa$, $9ab$, $9ac$, ..., $9am$ constituting a first electrode column can be connected to the electric conductor $142a$ connected to the positive power source 11 and switches the switches $141b$, $141c$, ..., $141n$ so that the electric conductors $140b$, $140c$, ..., $140n$ connected to the electrodes $9ba$, $9bb$, $9bc$, ..., $9bm$, ..., $9na$, $9nb$, $9nc$, ..., $9nm$, i.e., the electrodes other than the electrodes $9aa$, $9ab$, $9ac$, ..., $9am$ constituting the first electrode column, can be connected to the electric conductors $143b$, $143c$, ..., $143n$ connected to the ground terminal 12.

When the switches $141a$, $140b$, $140c$, ..., $140n$ have been switched so that the electrodes $9aa$, $9ab$, $9ac$, ..., $9am$ constituting the first electrode column have been connected to the positive power source 11 and that the electrodes $9ba$, $9bb$, $9bc$, ..., $9bm$, ..., $9na$, $9nb$, $9nc$, ..., $9nm$, i.e., the electrodes other than the electrodes $9aa$, $9ab$, $9ac$, ..., $9am$ constituting the first electrode column, have been connected to the ground terminal 12, the control unit 20 turns the positive power source 11 on.

As a result, a positive voltage is applied to the electrodes $9aa$, $9ab$, $9ac$, ..., $9am$ constituting the first electrode column, thereby generating an electric field and an antibody to the hapten labeled with an enzyme which generates chemiluminescence emission when it contacts a chemiluminescent substrate and contained in the reaction solution 19 is attracted to the electrodes $9aa$, $9ab$, $9ac$, ..., $9am$ constituting the first electrode column.

Since the electric field generating device 10 has been moved to the electric field applying position and the electrodes $9aa$, $9ab$, $9ac$, ..., $9am$ in the first electrode column are inserted into the corresponding absorptive region 4 of the biochemical analysis unit 1, an antibody to the hapten labeled with an enzyme which generates chemiluminescence emission when it contacts a chemiluminescent substrate and contained in the reaction solution 19 is forcibly brought into contact with a hapten labeling a substance derived from a living organism and selectively hybridized with specific biding substances absorbed in the absorptive regions 4 of the biochemical analysis unit 1 into which the electrodes $9aa$, $9ab$, $9ac$, ..., $9am$, ..., $9nm$ in the first electrode column are inserted and is bound with the hapten an antigen-antibody reaction.

Therefore, it is possible to markedly improve the efficiency of an antigen-antibody reaction and since it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with specific biding substances as a target absorbed in the absorptive regions 4 of the biochemical analysis unit 1 into which the electrodes 9aa, 9ab, 9ac, . . . , 9am in the first electrode column are inserted, it is possible to bind by an antigen-antibody reaction in a desired manner an antibody to the hapten labeled with an enzyme which generates chemiluminescence emission when it contacts a chemiluminescent substrate and contained in the reaction solution 19 with a hapten labeling a substance derived from a living organism and selectively hybridized with specific biding substances absorbed in the absorptive regions 4 of the biochemical analysis unit 1 into which the electrodes 9aa, 9ab, 9ac, . . . , 9am in the first electrode column are inserted.

When a predetermined time period has passed, the control unit 20 turns the positive power source 11 off.

As a result, an antibody to the hapten labeled with an enzyme which generates chemiluminescence emission when it contacts a chemiluminescent substrate and contained in the reaction solution 19 which was attracted to the absorptive regions 4 of the biochemical analysis unit 1 into which the electrodes 9aa, 9ab, 9ac, . . . , 9am in the first electrode column are inserted but was nevertheless not bound with a hapten labeling a substance derived from a living organism and selectively hybridized with specific biding substances contained in the absorptive regions 4 of the biochemical analysis unit 1 leaves the absorptive regions 4 into which the electrodes 9aa, 9ab, 9ac, . . . , 9am in the first electrode column are inserted.

The control unit 20 then switches the switch 141b so that the electric conductor 140b connected to the electrodes 9ba, 9bb, 9bc, . . . , 9bm constituting a second electrode column can be connected to the electric conductor 142b connected to the positive power source 11 and switches the switches 141a connected to the electrodes 9aa, 9ab, 9ac, . . . , 9am constituting the first electrode column so that the electric conductor 140a connected to the electrodes 9aa, 9ab, 9ac, . . . , 9am constituting the first electrode column can be connected to the electric conductor 143a connected the ground terminal 1, thereby connecting the electrodes 9aa, 9ab, 9ac, . . . , 9am, . . . , 9na, 9nb, 9nc, . . . , 9nm, i.e., the electrodes other than the electrodes 9ba, 9bb, 9bc, . . . , 9bm constituting the second electrode column, to the ground terminal 12.

When the switches 141a and 141b have been switched so that the electrodes 9ba, 9bb, 9bc, . . . , 9bm constituting the second electrode column have been to the positive power source 11 and that the electrodes 9aa, 9ab, 9ac, . . . , 9am, . . . , 9na, 9nb, 9nc, . . . , 9nm, i.e. the electrodes other than the electrodes 9ba, 9bb, 9bc, . . . , 9bm in second electrode column, have been connected to the ground terminal 12, the control unit 20 turns the positive power source 11 on.

As a result, a positive voltage is applied to the electrodes 9ba, 9bb, 9bc, . . . , 9bm constituting the second electrode column, thereby generating an electric field and an antibody to the hapten labeled with an enzyme which generates chemiluminescence emission when it contacts a chemiluminescent substrate and contained in the reaction solution 19 is attracted to the electrodes 9ba, 9bb, 9bc, . . . , 9bm constituting the second electrode column, whereby an antibody to the hapten labeled with an enzyme which generates chemiluminescence emission when it contacts a chemiluminescent substrate and contained in the reaction solution 19 is forcibly brought into contact with a hapten labeling a substance derived from a living organism and selectively hybridized with specific biding substances absorbed in the absorptive regions 4 of the biochemical analysis unit 1 into which the electrodes 9ba, 9bb, 9bc, . . . , 9bm in the second electrode column are inserted and bound with a hapten by an antigen-antibody reaction.

Therefore, it is possible to markedly improve the efficiency of an antigen-antibody reaction and since it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with specific biding substances as a target absorbed in the absorptive regions 4 of the biochemical analysis unit 1 into which the electrodes 9ba, 9bb, 9bc, . . . , 9bm in the second electrode column are inserted, it is possible to bind by an antigen-antibody reaction in a desired manner an antibody to the hapten labeled with an enzyme which generates chemiluminescence emission when it contacts a chemiluminescent substrate and contained in the reaction solution 19 with a hapten labeling a substance derived from a living organism and selectively hybridized with specific biding substances absorbed in the absorptive regions 4 of the biochemical analysis unit 1 into which the electrodes 9ba, 9bb, 9bc, . . . , 9bm in the second electrode column are inserted.

When a predetermined time period has passed, the control unit 20 turns the positive power source 11 off. Similarly to the above, the control unit 20 controls the switching operation of the switches 141a, 141b, 141c, . . . , 141n so that each electrode column of a third electrode column to an nth electrode column can be sequentially connected to the positive power source 11 while other electrode columns can be connected to the ground terminal 12 and sequentially applies a positive voltage to electrodes of each of the electrode columns connected to the positive power source 11, thereby generating an electric field.

As a result, an antibody to the hapten labeled with an enzyme which generates chemiluminescence emission when it contacts a chemiluminescent substrate and contained in the reaction solution 19 is sequentially attracted to electrodes of each of the electrode columns and is forcibly brought into contact with a hapten labeling a substance derived from a living organism and selectively hybridized with specific binding substances absorbed in the absorptive regions 4 of the biochemical analysis unit 1 into which the electrodes of the electrode column are inserted, whereby a substance derived from a living organism and contained in the reaction solution 19 is bound with a hapten by an antigen-antibody reaction.

In this manner, according to this embodiment, the switching operation of the switches 141a, 141b, 141c, . . . , 141n is controlled so that electrodes of each of the electrode columns can be sequentially connected to the positive power source 11 while other electrode columns can be connected to the ground terminal 12 and a positive voltage is sequentially applied to electrodes of each of the electrode columns connected to the positive power source 11, thereby selectively attracting an antibody to the hapten labeled with an enzyme which generates chemiluminescence emission when it contacts a chemiluminescent substrate and contained in the reaction solution 19 to the electrodes of the electrode column applied with a positive voltage and forcibly bringing it into contact with a hapten labeling a substance derived from a living organism and selectively hybridized with specific binding substances contained in the absorptive regions 4 of the biochemical analysis unit 1 into which the electrodes of the electrode column to be bound with a hapten by an antigen-antibody reaction. Therefore, it is possible to markedly improve the efficiency of an antigen-antibody reaction and since it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with specific binding substances as a target absorbed in the absorptive regions 4 of the biochemical analysis unit 1 into which the electrodes of the electrode column applied with a positive voltage are inserted, it is possible to bind by an antigen-antibody reaction in a desired manner an antibody to the hapten labeled with an enzyme which generates chemiluminescence emission when it contacts a chemiluminescent substrate and contained in the reaction solution 19 with a hapten labeling a substance derived from a living organism and selectively hybridized with specific binding substances absorbed in the absorptive regions 4 of the biochemical analysis unit 1 into which the electrodes of the electrode column applied with a positive voltage are inserted.

Moreover, according to this embodiment, since a positive voltage is sequentially applied from the positive power source 11 to electrodes of each of the electrode columns and the positive power source 11 is turned off when a predetermined time period has passed, an antibody to the hapten labeled with an enzyme which generates chemiluminescence emission when it contacts a chemiluminescent substrate which was attracted to the absorptive regions 4 of the biochemical analysis unit 1 into which the electrodes of the electrode column applied with a positive voltage are inserted but was nevertheless not bound by an antigen-antibody reaction with a hapten labeling a substance derived from a living organism and selectively hybridized with specific binding substances contained in the absorptive regions 4 of the biochemical analysis unit 1 leaves the absorptive regions 4 when the positive power source 11 is turned off to be returned to the reaction solution 19 and is attracted to electrodes of an electrode column next applied with a positive voltage. Therefore, since an antibody to the hapten labeled with an enzyme which generates chemiluminescence emission when it contacts a chemiluminescent substrate are moved in the reaction solution 19 in response to the on and off operation of the positive power source 11 similarly to the case where the reaction solution 19 is agitated, it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with specific binding substances as a target contained in a number of the absorptive regions 4 of the biochemical analysis unit 1.

Thus, chemiluminescent data are recorded in a number of the absorptive regions 4 of the biochemical analysis unit 1.

Similarly to the previous embodiments, the chemiluminescent data recorded in a number of the absorptive regions 4 of the biochemical analysis unit 1 by the cooled CCD camera 91 of the data producing system shown in FIGS. 17 to 20 and biochemical analysis data are produced.

In this embodiment, while the electric field generating device 10 provided with the electrodes 9aa, 9ab, 9ac, . . . , 9am, . . . , 9nm at positions corresponding to those of the absorptive regions 4 formed in the biochemical analysis unit 1 is moved to the electric field applying position and the electrodes 9aa, 9ab, 9ac, . . . , 9am, . . . , 9nm are inserted into the corresponding absorptive regions 4 of the biochemical analysis unit 1, the switching operation of the switches 141a, 141b, 141c, . . . , 141n is controlled so that electrodes of each of the electrode columns are sequentially connected to the positive power source 11 and that electrodes of other electrode columns are sequentially connected to the ground terminal 12 and a positive voltage is applied to the electrodes of the electrode column connected to the positive power source 11, thereby selectively attracting a substance derive from a living organism and contained in the reaction solution 19 to only the electrodes of the electrode column applied with a positive voltage, forcibly bringing it into contact with specific binding substances contained in the absorptive regions 4 of the biochemical analysis unit 1 into which the electrodes of the electrode column are inserted and hybridizing it with the specific binding substances.

Therefore, according to this embodiment, it is possible to markedly improve the efficiency of hybridization and since it is possible to markedly increase the possibility of association of a substance derived from a living organism and contained in the reaction solution 19 with specific binding substances as a target contained in the absorptive regions 4 of the biochemical analysis unit 1 into which the electrodes of the electrode column applied with a positive voltage are inserted, it is possible to selectively hybridize in a desired manner the substance derived from a living organism and contained in the reaction solution 19 with the specific binding substance absorbed in t he absorptive region 4 of the biochemical analysis unit 1 into which the electrodes of the electrode column applied with a positive voltage are inserted.

Moreover, according to this embodiment, since a positive voltage is sequentially applied from the positive power source 11 to electrodes of each of the electrode columns, a substance derived from a living organism which was attracted to the absorptive regions 4 of the biochemical analysis unit 1 into which the electrodes of the electrode column applied with a positive voltage are inserted but was nevertheless not hybridized with specific binding substances contained in the absorptive regions 4 of the biochemical analysis unit 1 is moved in the reaction solution 19 by applying a positive voltage to electrodes of a next electrode column. Therefore, it is possible to markedly increase the possibility of association of the substance derived from a living organism and contained in the reaction solution 19 with specific binding substances as a target contained in a number of the absorptive regions 4 of the biochemical analysis unit 1.

Furthermore, in this embodiment, while the electric field generating device 10 provided with the electrodes 9aa, 9ab, 9ac, . . . , 9am, . . . , 9nm at positions corresponding to those of the absorptive regions 4 formed in the biochemical analysis unit 1 is moved to the electric field applying position and the electrodes 9aa, 9ab, 9ac, . . . , 9am, . . . , 9nm are inserted into the corresponding absorptive regions 4 of the biochemical analysis unit 1, the switching operation of the switches 141a, 141b, 141c, . . . , 141n is controlled so that electrodes of each of the electrode columns are sequentially connected to the positive power source 11 and that electrodes of other electrode columns are sequentially connected to the ground terminal 12 and a positive voltage is applied to the electrodes of the electrode column connected to the positive power source 11, thereby selectively attracting an antibody to the hapten labeled with an enzyme which generates chemiluminescence emission when it contacts a chemiluminescent substrate and contained in the reaction solution 19 to only the electrodes of the electrode column applied with a positive voltage, forcibly bringing it into contact with a hapten labeling a substance derived from a living organism and selectively hybridized with specific binding substances contained in the absorptive regions 4 of the biochemical analysis unit 1 into which the electrodes of the electrode column are inserted and binding it with the hapten by an antigen-antibody reaction.

Therefore, according to this embodiment, it is possible to markedly improve the efficiency of an antigen-antibody reaction and since it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with specific binding substances as a target contained in the absorptive regions 4 of the biochemical analysis unit 1 into which the electrodes of the electrode column applied with a positive voltage are inserted, it is possible to bind by an antigen-antibody reaction in a desired manner an antibody to the hapten labeled with an enzyme which generates chemiluminescence emission when it contacts a chemiluminescent substrate and contained in the reaction solution 19 with a hapten labeling a substance derived from a living organism and selectively hybridized with specific binding substance absorbed in the absorptive region 4 of the biochemical analysis unit 1 into which the electrodes of the electrode column applied with a positive voltage are inserted.

Moreover, according to this embodiment, since a positive voltage is sequentially applied from the positive power source 11 to electrodes of each of the electrode columns, an antibody to the hapten labeled with an enzyme which generates chemiluminescence emission when it contacts a chemiluminescent substrate which was attracted to the absorptive regions 4 of the biochemical analysis unit 1 into which the electrodes of the electrode column applied with a positive voltage are inserted but was nevertheless not bound by an antigen-antibody reaction with a hapten labeling a substance derived from a living organism and selectively hybridized with specific binding substances contained in the absorptive regions 4 of the biochemical analysis unit 1 is moved in the reaction solution 19 by applying a positive voltage to electrodes of a next electrode column. Therefore, it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with specific binding substances as a target contained in a number of the absorptive regions 4 of the biochemical analysis unit 1.

Figure 25:
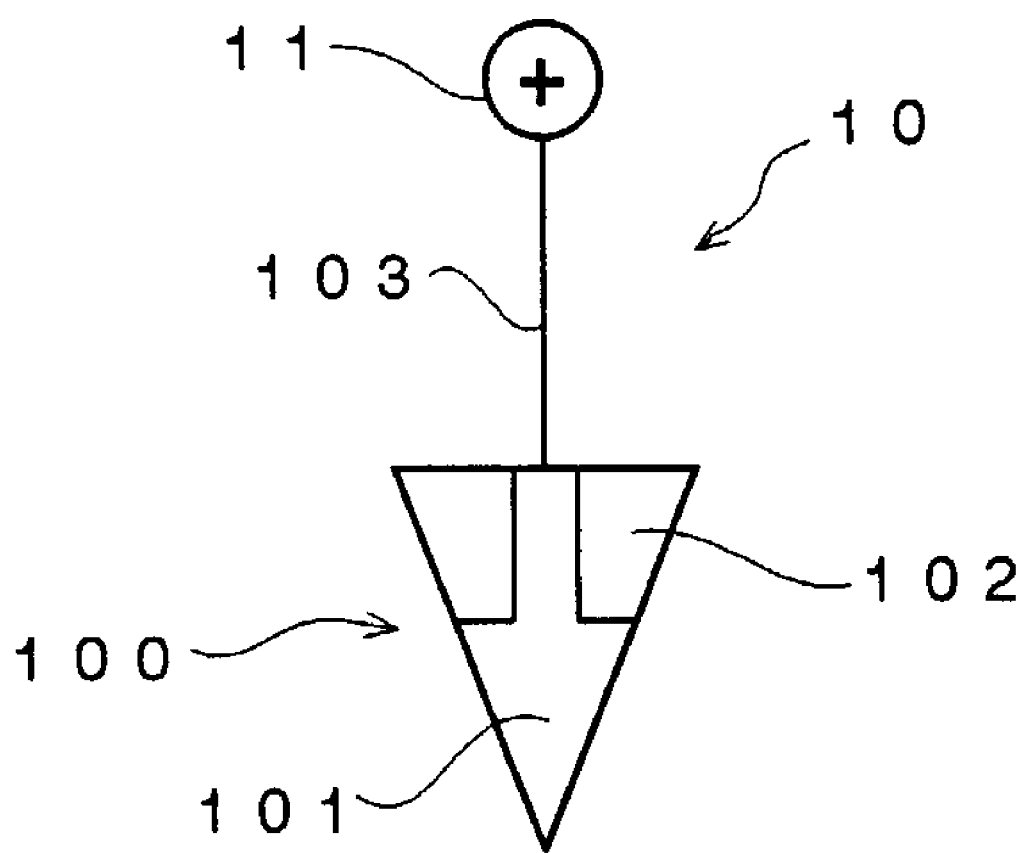
FIG. 25 is a schematic cross-sectional view showing electrodes provided in an electric field generating device of an apparatus for conducting a receptor-ligand association reaction which is a further preferred embodiment of the present invention.
Figure 26:
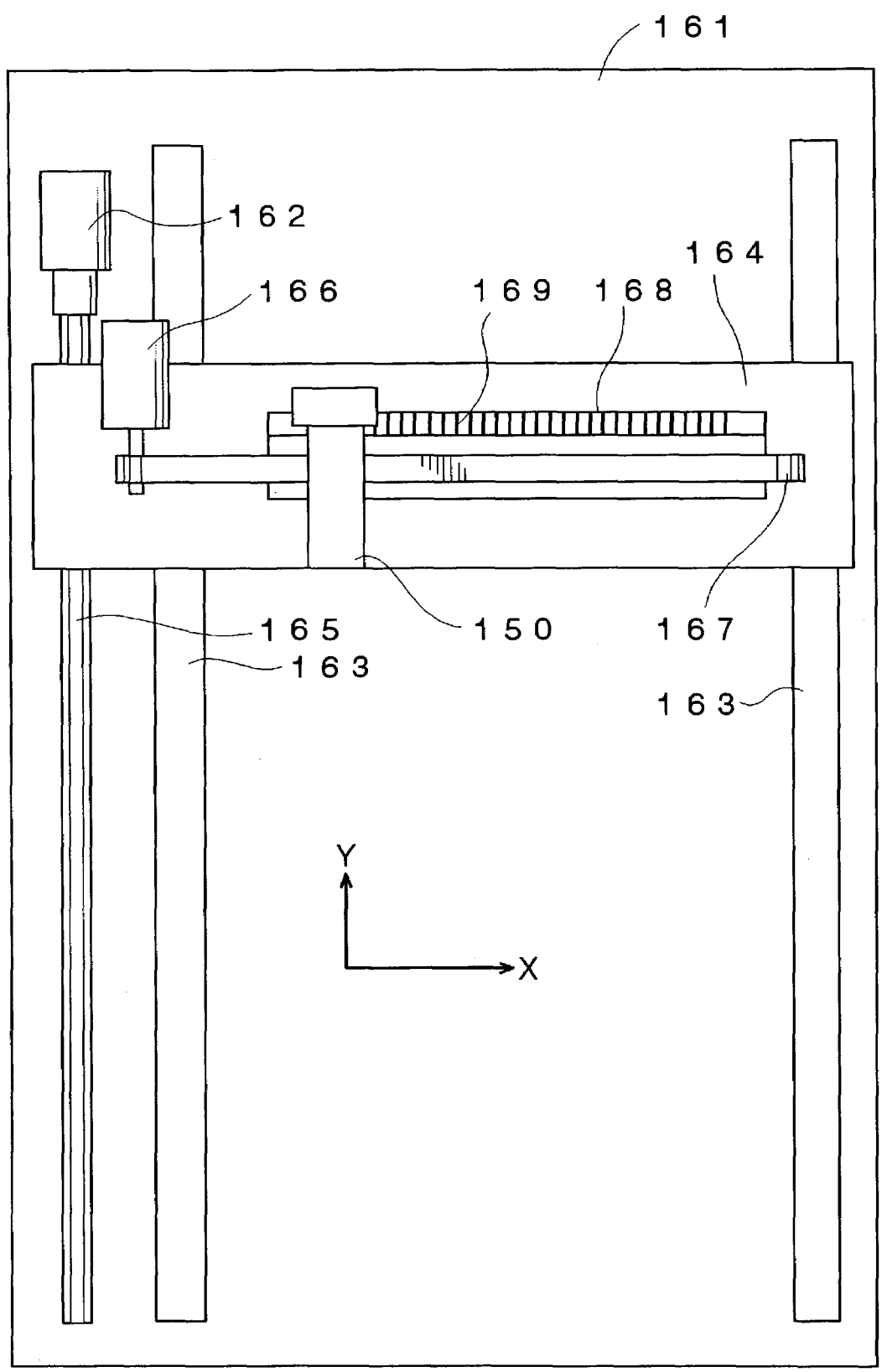
FIG. 26 is a schematic plan view showing an electric field generating device of an apparatus for conducting a receptor-ligand association reaction which is a further preferred embodiment of the present invention.

FIG. 25 is a schematic cross-sectional view showing an electrode provided in an electric field generating device of an apparatus for conducting a receptor-ligand association reaction which is a further preferred embodiment of the present invention and FIG. 26 is a schematic plan view showing the electric field generating device.

As shown in FIG. 25, an electric field generating device 10 of an apparatus for conducting a receptor-ligand association reaction according to this embodiment includes a single electrode 150 that has a cone-like shape and is constituted by a pin-like conductive member 151 and an insulating member 152 covering a portion of the conductive member 151 other than a tip end portion thereof. An electric conductor 153 connected to the positive power source 11 is connected to the conductive member 151 of the electrode 150.

As shown in FIG. 26, the electrode 150 of the electric field generating device 10 of the apparatus for conducting a receptor-ligand association reaction according to this embodiment is constituted so as to be movable by a drive mechanism in a main scanning direction indicated by an arrow X and a sub-scanning direction indicated by an arrow Y in FIG. 26.

The driving mechanism of the electric field generating device 10 is mounted on a frame 161 of the reaction vessel 7 of the apparatus for conducting a receptor-ligand association reaction.

As shown in FIG. 26, a sub-scanning pulse motor 162 and a pair of rails 163, 163 are fixed on the frame 161 and a movable base plate 164 is further provided on the frame 161 so as to be movable along the pair of rails 163, 163 in the sub-scanning direction indicated by the arrow Y in FIG. 26.

The movable base plate 164 is formed with a threaded hole (not shown) and a threaded rod 165 rotated by the sub-scanning pulse motor 162 is engaged with the inside of the hole.

A main scanning pulse motor 166 is provided on the movable base plate 164. The main scanning pulse motor 166 is adapted for intermittently driving an endless belt 167 at a predetermined pitch.

The electrode 150 of the electric field generating device 10 is mounted on the endless belt 167 so as to be movable by a solenoid (not shown) in the vertical direction and when the endless belt 167 is driven by the main scanning pulse motor 166, the electrode 150 is moved in the main scanning direction indicated by the arrow X in FIG. 26.

In FIG. 26, the reference numeral 168 designates a linear encoder for detecting the position of the electrode 150 in the main scanning direction and the reference numeral 169 designates slits of the linear encoder 168.

Figure 27:
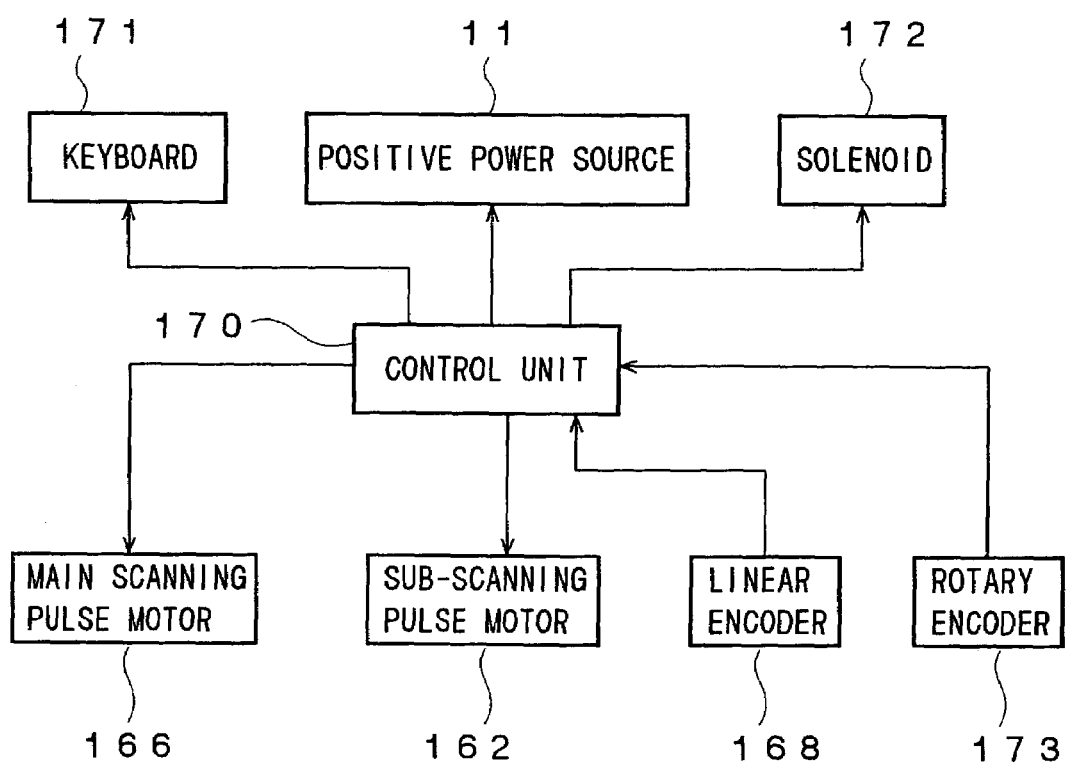
FIG. 27 is a block diagram of a control system, an input system, a drive system and a detection system of an electric field generating device of an apparatus for conducting a receptor-ligand association reaction which is a further preferred embodiment of the present invention.

FIG. 27 is a block diagram of a control system, an input system, a drive system and a detection system of the electric field generating device 10 of the apparatus for conducting a receptor-ligand association reaction according to this embodiment.

As shown in FIG. 27, the control system of the electric field generating device 10 includes a control unit 170 for controlling the overall operation of the electric field generating device 10 and the input system of the electric field generating device 10 includes a keyboard 171.

The control unit 170 is adapted to control the on and off operation of the positive power source 11.

As shown in FIG. 27, the drive system of the electric field generating device 10 includes the main scanning pulse motor 166, the sub-scanning pulse motor 162 and a solenoid 172 for moving the electrode 150 in the vertical direction, and the detection system of the electric field generating device 10 includes the linear encoder 168 for detecting the position of the electrode 150 in the main scanning direction and a rotary encoder 173 for detecting an amount of rotation of the rod 165.

The thus constituted electric field generating device 10 of the apparatus for conducting a receptor-ligand association reaction according to this embodiment selectively hybridizes a substance derived from a living organism and contained in the reaction solution 19 with specific binding substances such as cDNAs absorbed in the absorptive regions 4 of the biochemical analysis unit 1 in the following manner.

The biochemical analysis unit 1 formed with a number of the absorptive regions 4 in which specific binding substances are absorbed is first set at the biochemical analysis unit holding section 8.

A reaction solution 19 is then prepared and accommodated in the reaction vessel 7.

In this embodiment, a reaction solution 19 containing a substance derived from a living organism and labeled with a radioactive labeling substance, a substance derived from a living organism and labeled with a hapten such as digoxigenin and a substance derived from a living organism and labeled with a fluorescent substance such as a fluorescent dye is prepared and accommodated in the reaction vessel 7.

Position data regarding positions of the absorptive regions 4 formed in the substrate 2 of the biochemical analysis unit 1 are then input through the keyboard 171.

The position data input through the keyboard 171 are input to the control unit 170 and when the control unit 170 receives the position data, it calculates drive pulses to be sent to the main scanning pulse motor 166 and the sub-scanning pulse motor 162 in order to move the electrode 150 to the position of each of the absorptive regions 4 of the biochemical analysis unit 1 and stores driving pulse data in the memory.

In this embodiment, since 19,200 absorptive regions 4 are formed in the substrate 2 of the biochemical analysis unit 1 so as to be spaced apart from each other by a constant interval in a regular pattern and in the manner of a matrix, the drive pulses to be sent to the main scanning pulse motor 166 and the sub-scanning pulse motor 162 in order to move the electrode 150 to a position where the electrode 150 faces a third or a subsequent absorptive region 4 are equal to the drive pulses to be sent to the main scanning pulse motor 166 and the sub-scanning pulse motor 162 in order to move the electrode 150 from the position where the electrode 150 faces a first absorptive region 4 to the position where the electrode 150 faces a second absorptive region 4. Therefore, it is sufficient to calculate drive pulses to be sent to the main scanning pulse motor 166 and the sub-scanning pulse motor 162 in order to move the electrode 150 to the position where the electrode 150 faces the first absorptive region 4 and drive pulses to be sent to the main scanning pulse motor 166 and the sub-scanning pulse motor 162 in order to move the electrode 150 from the position where the electrode 150 faces the first absorptive region 4 to the position where the electrode 150 faces the second absorptive region 4 and store them in the memory.

When the position data have been input through the keyboard 171 and drive pulses to be sent to the main scanning pulse motor 166 and the sub-scanning pulse motor 162 in order to move the electrode 150 to the position where the electrode 150 faces each of the absorptive regions 4 of the biochemical analysis unit 1 have been calculated and stored in the memory, a start signal is input by a user through the keyboard 171.

The start signal is output to the control unit 170 and when the control unit 170 receives the start signal, it sends predetermined drive pulses to the main scanning pulse motor 166 and the sub-scanning pulse motor 162 based on the drive pulse data stored in the memory, thereby moving the electrode 150. When the electrode 150 has reached the position where the electrode 150 faces the first absorptive region 4, the control unit 170 outputs drive stop signals to the main scanning pulse motor 166 and the sub-scanning pulse motor 162, thereby stopping the electrode 150 and outputs a drive signal to the solenoid 172, thereby causing it to lower the electrode 150 so as to be inserted into the first absorptive region 4 of the biochemical analysis unit 1.

The control unit 170 then turns the positive power source 11 on.

As a result, a positive voltage is applied to the electrode 150 and an electric field is generated by the electrode 150 so that a substance derived from a living organism and contained in the reaction solution 19 is attracted to the electrode 150.

Since the electrode 150 of the electric field generating device 10 has been lowered by the solenoid 172 and inserted into the first absorptive region 4 of the biochemical analysis unit 1, a substance derived from a living organism and contained in the reaction solution 19 is forcibly brought into contact with a specific binding substance absorbed in the first absorptive region 4 of the biochemical analysis unit 1 and selectively hybridized with the specific binding substance.

Therefore, it is possible to markedly improve the efficiency of hybridization and since it is possible to markedly increase the possibility of association of the substance derived from a living organism and contained in the reaction solution 19 with a specific binding substance as a target absorbed in the first absorptive region 4 of the biochemical analysis unit 1 into which the electrode is inserted, it is possible to selectively hybridize in a desired manner the substance derived from a living organism and contained in the reaction solution 19 with the specific binding substance absorbed in the first absorptive region 4 of the biochemical analysis unit 1 into which the electrode is inserted.

When a predetermined time period has passed, the control unit 170 turns the positive power source 11 off and outputs a drive stop signal to the solenoid 172, thereby causing it to raise the electrode 150 so as to be retracted from the first absorptive region 4 of the biochemical analysis unit 1.

As a result, a substance derived from a living organism which was attracted to the first absorptive region 4 of the biochemical analysis unit 1 but was not hybridized with a specific binding substance absorbed in the first absorptive region 4 of the biochemical analysis unit 1 leaves the first absorptive region 4 of the biochemical analysis unit 1 and is returned into the reaction solution 19.

The control unit 170 then sends predetermined drive pulses to the main scanning pulse motor 166 and the sub-scanning pulse motor 162 based on the drive pulse data stored in the memory, thereby moving the electrode 150 to the position where the electrode 150 faces the second absorptive region 4 of the biochemical analysis unit 1. When the electrode 150 has reached the position where the electrode 150 faces the second absorptive region 4, the control unit 170 outputs drive stop signals to the main scanning pulse motor 166 and the sub-scanning pulse motor 162, thereby stopping the electrode 150 and outputs a drive signal to the solenoid 172, thereby causing it to lower the electrode 150 so as to be inserted into the second absorptive region 4 of the biochemical analysis unit 1.

When the electrode 150 has been inserted into the second absorptive region 4 of the biochemical analysis unit 1, the control unit 170 turns the positive power source 11 on.

As a result, a positive voltage is applied to the electrode 150 and an electric field is generated by the electrode 150 so that a substance derived from a living organism and contained in the reaction solution 19 is attracted to the electrode 150. Therefore, a substance derived from a living organism and contained in the reaction solution 19 is forcibly brought into contact with a specific binding substance absorbed in the second absorptive region 4 of the biochemical analysis unit 1 and selectively hybridized with the specific binding substance.

When a predetermined time period has passed, the control unit 170 turns the positive power source 11 off and outputs a drive stop signal to the solenoid 172, thereby causing it to raise the electrode 150 so as to be retracted from the second absorptive region 4 of the biochemical analysis unit 1.

As a result, a substance derived from a living organism which was attracted to the second absorptive region 4 of the biochemical analysis unit 1 but was not hybridized with a specific binding substance absorbed in the second absorptive region 4 of the biochemical analysis unit 1 leaves the first absorptive region 4 of the biochemical analysis unit 1 and is returned into the reaction solution 19.

Similarly to the above, hybridization is performed by moving the electrode 150 by a constant pitch by the main scanning pulse motor 166 and the sub-scanning pulse motor 162 in the main scanning direction indicated by the arrow X and the sub-scanning direction indicated by the arrow Y in FIG. 27 and sequentially inserting the electrode 150 into a third or a subsequent absorptive region 4 of the biochemical analysis unit 1.

In this embodiment, since the electrode 150 is inserted into a particular absorptive region 4 of the biochemical analysis unit 1 and a positive voltage is applied to the electrode 150, thereby performing a hybridization reaction for a predetermined time period and the positive power source 11 is then turned off, a substance derived from a living organism which was attracted to the absorptive region 4 of the biochemical analysis unit 1 but was not hybridized with a specific binding substance absorbed in the absorptive region 4 of the biochemical analysis unit 1 leaves the absorptive region 4 of the biochemical analysis unit 1 and is returned into the reaction solution 19. Therefore, since a substance derived from a living organism is moved in the reaction solution 19 in response to the operation for inserting the electrode 150 into the absorptive regions 4 and retracting the electrode 150 from the absorptive regions 4 similarly to the case where the reaction solution 19 is agitated, it is possible to markedly increase the possibility of association of the substance derived from a living organism and contained in the reaction solution 19 with specific binding substances as a target absorbed in a number of the absorptive regions 4 of the biochemical analysis unit 1.

In this manner, radiation data of a radioactive labeling substance and a fluorescence data of a fluorescent substance such as a fluorescent dye are recorded in a number of the absorptive regions 4 formed in the substrate 2 of the biochemical analysis unit 1.

Similarly to the previous embodiments, the fluorescence data recorded in a number of the absorptive regions 4 of the biochemical analysis unit 1 are read by the scanner shown in FIG. 9 and biochemical analysis data are produced.

On the other hand, the radiation data recorded in a number of the absorptive regions 4 of the biochemical analysis unit 1 are transferred into a number of the stimulable phosphor layer regions 27 the stimulable phosphor sheet 25 shown in FIG. 7 and the radiation data into a number of the stimulable phosphor layer regions 27 the stimulable phosphor sheet 25 are read by the scanner shown in FIG. 9 similarly to the previous embodiment, whereby biochemical analysis data are produced.

To the contrary, in order to record chemiluminescence data in a number of the absorptive regions 4 formed in the substrate 2 of the biochemical analysis unit 1, a reaction solution 19 containing an antibody to the hapten such as digoxigenin labeled with an enzyme which generates chemiluminescence emission when it contacts a chemiluminescent substrate is further prepared and accommodated in the reaction vessel 7 and the antibody to the hapten such as digoxigenin labeled with an enzyme which generates chemiluminescence emission when it contacts a chemiluminescent substrate is bound with the hapten such as digoxigenin labeling a substance derived from a living organism selectively hybridized with specific binding substances absorbed in a number of the absorptive regions 4 formed in the substrate 2 of the biochemical analysis unit 1 by the an antigen-antibody reaction.

Specifically, a reaction solution 19 containing an antibody to the hapten such as digoxigenin labeled with an enzyme which generates chemiluminescence emission when it contacts a chemiluminescent substrate is first prepared and accommodated in the reaction vessel 7.

When the reaction solution 19 is prepared and accommodated in the reaction vessel 7, a start signal is input by a user through the keyboard 171.

The start signal is output to the control unit 170 and when the control unit 170 receives the start signal, it sends predetermined drive pulses to the main scanning pulse motor 166 and the sub-scanning pulse motor 162 based on the drive pulse data stored in the memory, thereby moving the electrode 150. When the electrode 150 has reached the position where the electrode 150 faces the first absorptive region 4, the control unit 170 outputs drive stop signals to the main scanning pulse motor 166 and the sub-scanning pulse motor 162, thereby stopping the electrode 150 and outputs a drive signal to the solenoid 172, thereby causing it to lower the electrode 150 so as to be inserted into the first absorptive region 4 of the biochemical analysis unit 1.

The control unit 170 then turns the positive power source 11 on.

As a result, a positive voltage is applied to the electrode 150 and an electric field is generated by the electrode 150 so that an antibody to the hapten labeled with an enzyme which generates chemiluminescence emission when it contacts a chemiluminescent substrate and contained in the reaction solution 19 is attracted to the electrode 150.

Since the electrode 150 of the electric field generating device 10 has been lowered by the solenoid 172 and inserted into the first absorptive region 4 of the biochemical analysis unit 1, an antibody to the hapten labeled with an enzyme which generates chemiluminescence emission when it contacts a chemiluminescent substrate and contained in the reaction solution 19 is forcibly brought into contact with a hapten labeling a substance derived from a living organism and selectively hybridized with a specific binding substance absorbed in the first absorptive region 4 of the biochemical analysis unit 1 and bound with the hapten by an antigen-antibody reaction.

Therefore, it is possible to markedly improve the efficiency of an antigen-antibody reaction and since it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with a specific binding substance as a target absorbed in the first absorptive region 4 of the biochemical analysis unit 1 into which the electrode is inserted, it is possible to bind by an antigen-antibody reaction in a desired manner an antibody to the hapten labeled with an enzyme which generates chemiluminescence emission when it contacts a chemiluminescent substrate and contained in the reaction solution 19 with a hapten labeling a substance derived from a living organism and selectively hybridized with a specific binding substance absorbed in the first absorptive region 4 of the biochemical analysis unit 1 into which the electrode is inserted.

When a predetermined time period has passed, the control unit 170 turns the positive power source 11 off and outputs a drive stop signal to the solenoid 172, thereby causing it to raise the electrode 150 so as to be retracted from the first absorptive region 4 of the biochemical analysis unit 1.

As a result, an antibody to the hapten labeled with an enzyme which generates chemiluminescence emission when it contacts a chemiluminescent substrate which was attracted to the first absorptive region 4 of the biochemical analysis unit 1 but was nevertheless not bound by an antigen-antibody reaction with a hapten labeling a substance derived from a living organism and selectively hybridized with a specific binding substance absorbed in the first absorptive region 4 of the biochemical analysis unit 1 leaves the first absorptive region 4 of the biochemical analysis unit 1 and is returned into the reaction solution 19.

The control unit 170 then sends predetermined drive pulses to the main scanning pulse motor 166 and the sub-scanning pulse motor 162 based on the drive pulse data stored in the memory, thereby moving the electrode 150 to the position where the electrode 150 faces the second absorptive region 4 of the biochemical analysis unit 1. When the electrode 150 has reached the position where the electrode 150 faces the second absorptive region 4, the control unit 170 outputs drive stop signals to the main scanning pulse motor 166 and the sub-scanning pulse motor 162, thereby stopping the electrode 150 and outputs a drive signal to the solenoid 172, thereby causing it to lower the electrode 150 so as to be inserted into the second absorptive region 4 of the biochemical analysis unit 1.

When the electrode 150 has been inserted into the second absorptive region 4 of the biochemical analysis unit 1, the control unit 170 turns the positive power source 11 on.

As a result, a positive voltage is applied to the electrode 150 and an electric field is generated by the electrode 150 so that an antibody to the hapten labeled with an enzyme which generates chemiluminescence emission when it contacts a chemiluminescent substrate and contained in the reaction solution 19 is attracted to the electrode 150. Therefore, an antibody to the hapten labeled with an enzyme which generates chemiluminescence emission when it contacts a chemiluminescent substrate and contained in the reaction solution 19 is forcibly brought into contact with a hapten labeling a substance derived from a living organism and selectively hybridized with a specific binding substance absorbed in the second absorptive region 4 of the biochemical analysis unit 1 and bound with the hapten by an antigen-antibody reaction.

When a predetermined time period has passed, the control unit 170 turns the positive power source 11 off and outputs a drive stop signal to the solenoid 172, thereby causing it to raise the electrode 150 so as to be retracted from the second absorptive region 4 of the biochemical analysis unit 1.

As a result, an antibody to the hapten labeled with an enzyme which generates chemiluminescence emission when it contacts a chemiluminescent substrate which was attracted to the first absorptive region 4 of the biochemical analysis unit 1 but was nevertheless not bound by an antigen-antibody reaction with a hapten labeling a substance derived from a living organism and selectively hybridized with a specific binding substance absorbed in the second absorptive region 4 of the biochemical analysis unit 1 leaves the first absorptive region 4 of the biochemical analysis unit 1 and is returned into the reaction solution 19.

Similarly to the above, an antigen-antibody reaction is performed by moving the electrode 150 by a constant pitch by the main scanning pulse motor 166 and the sub-scanning pulse motor 162 in the main scanning direction indicated by the arrow X and the sub-scanning direction indicated by the arrow Y in FIG. 27 and sequentially inserting the electrode 150 into a third or a subsequent absorptive region 4 of the biochemical analysis unit 1.

In this embodiment, since the electrode 150 is inserted into a particular absorptive region 4 of the biochemical analysis unit 1 and a positive voltage is applied to the electrode 150, thereby performing a hybridization reaction for a predetermined time period and the positive power source 11 is then turned off, an antibody to the hapten labeled with an enzyme which generates chemiluminescence emission when it contacts a chemiluminescent substrate which was attracted to the absorptive region 4 of the biochemical analysis unit 1 but was nevertheless not bound by an antigen-antibody reaction with a hapten labeling a substance derived from a living organism and selectively hybridized with a specific binding substance absorbed in the absorptive region 4 of the biochemical analysis unit 1 leaves the absorptive region 4 of the biochemical analysis unit 1 and is returned into the reaction solution 19. Therefore, since an antibody to the hapten labeled with an enzyme which generates chemiluminescence emission when it contacts a chemiluminescent substrate and contained in the reaction solution 19 in response to the operation for inserting the electrode 150 into the absorptive regions 4 and retracting the electrode 150 from the absorptive regions 4 similarly to the case where the reaction solution 19 is agitated, it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with specific binding substances as a target absorbed in a number of the absorptive regions 4 of the biochemical analysis unit 1.

In this manner, chemiluminescent data are recorded in a number of the absorptive regions 4 of the biochemical analysis unit 1.

Similarly to the previous embodiments, the chemiluminescent data recorded in a number of the absorptive regions 4 of the biochemical analysis unit 1 by the cooled CCD camera 91 of the data producing system shown in FIGS. 17 to 20 and biochemical analysis data are produced.

In this embodiment, the cone-like electrode 150 connected to the positive power source 11 is sequentially moved by the main scanning pulse motor 166 and the sub-scanning pulse motor 162 in the main scanning direction indicated by the arrow X and the sub-scanning direction indicated by the arrow Y in FIG. 26 and the solenoid 172 is actuated every time the electrode 150 faces one of the absorptive regions 4 formed in the substrate 2 of the biochemical analysis unit 1, thereby inserting the electrode 150 into the absorptive region 4 it faces and when a predetermined time period has passed, the electrode 150 is retracted from the absorptive region 4.

Therefore, according to this embodiment, a substance derived from a living organism and contained in the reaction solution 19 is selectively attracted to only the absorptive region 4 of the biochemical analysis unit 1 into which the electrode 150 is inserted and is forcibly brought into contact with a specific binding substance absorbed in the absorptive region 4 of the biochemical analysis unit 1 into which the electrode 150 is inserted, thereby being hybridized with the specific binding substance. Accordingly, it is possible to markedly improve the efficiency of hybridization and since it is possible to markedly increase the possibility of association of a substance derived from a living organism and contained in the reaction solution 19 with specific binding substances as a target absorbed in the absorptive regions 4 of the biochemical analysis unit 1 into which the electrode applied with a positive voltage is inserted, it is possible to selectively hybridize in a desired manner a substance derived from a living organism and contained in the reaction solution 19 with specific binding substances absorbed in the absorptive regions 4 of the biochemical analysis unit 1 into which the electrode applied with a positive voltage is inserted.

Moreover, according to this embodiment, since the electrode 150 is sequentially inserted into each of the absorptive regions 4 of the biochemical analysis unit 1 and a positive voltage is applied to the electrode 150, thereby performing a hybridization reaction for a predetermined time period and the positive power source 11 is then turned off, a substance derived from a living organism which was attracted to each of the absorptive regions 4 of the biochemical analysis unit 1 but was not hybridized with a specific binding substance absorbed in the absorptive region 4 of the biochemical analysis unit 1 leaves the absorptive region 4 of the biochemical analysis unit 1 and is returned into the reaction solution 19. Therefore, since a substance derived from a living organism is moved in the reaction solution 19 in response to the operation for inserting the electrode 150 into the absorptive regions 4 and retracting the electrode 150 from the absorptive regions 4 similarly to the case where the reaction solution 19 is agitated, it is possible to markedly increase the possibility of association of the substance derived from a living organism and contained in the reaction solution 19 with specific binding substances as a target absorbed in a number of the absorptive regions 4 of the biochemical analysis unit 1.

Furthermore, according to this embodiment, an antibody to the hapten labeled with an enzyme which generates chemiluminescence emission when it contacts a chemiluminescent substrate and contained in the reaction solution 19 is selectively attracted to only the absorptive region 4 of the biochemical analysis unit 1 into which the electrode 150 is inserted and is forcibly brought into contact with a hapten labeling a substance derived from a living organism and selectively hybridized with a specific binding substance absorbed in the absorptive region 4 of the biochemical analysis unit 1 into which the electrode 150 is inserted, thereby being bound with the specific binding substance by an antigen-antibody reaction. Accordingly, it is possible to markedly improve the efficiency of an antigen-antibody reaction and since it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with specific binding substances as a target absorbed in the absorptive regions 4 of the biochemical analysis unit 1 into which the electrode applied with a positive voltage is inserted, it is possible to bind by an antigen-antibody reaction in a desired manner an antibody to the hapten labeled with an enzyme which generates chemiluminescence emission when it contacts a chemiluminescent substrate and contained in the reaction solution 19 with a hapten labeling a substance derived from a living organism and selectively hybridized with specific binding substances absorbed in the absorptive regions 4 of the biochemical analysis unit 1 into which the electrode applied with a positive voltage is inserted.

Moreover, according to this embodiment, since the electrode 150 is sequentially inserted into each of the absorptive regions 4 of the biochemical analysis unit 1 and a positive voltage is applied to the electrode 150, thereby performing a hybridization reaction for a predetermined time period and the positive power source 11 is then turned off, an antibody to the hapten labeled with an enzyme which generates chemiluminescence emission when it contacts a chemiluminescent substrate which was attracted to each of the absorptive regions 4 of the biochemical analysis unit 1 but was nevertheless not bound by an antigen-antibody reaction with a hapten labeling a substance derived from a living organism and selectively hybridized with a specific binding substance absorbed in the absorptive region 4 of the biochemical analysis unit 1 leaves the absorptive region 4 of the biochemical analysis unit 1 and is returned into the reaction solution 19. Therefore, since an antibody to the hapten labeled with an enzyme which generates chemiluminescence emission when it contacts a chemiluminescent substrate is moved in the reaction solution 19 in response to the operation for inserting the electrode 150 into the absorptive regions 4 and retracting the electrode 150 from the absorptive regions 4 similarly to the case where the reaction solution 19 is agitated, it is possible to markedly increase the possibility of association of an antibody to the hapten labeled with an enzyme which generates chemiluminescence emission when it contacts a chemiluminescent substrate and contained in the reaction solution 19 with a hapten labeling a substance derived from a living organism and selectively hybridized with specific binding substances as a target absorbed in a number of the absorptive regions 4 of the biochemical analysis unit 1.

The present invention has thus been shown and described with reference to specific embodiments. However, it should be noted that the present invention is in no way limited to the details of the described arrangements but changes and modifications may be made without departing from the scope of the appended claims, For example, in the above described embodiments, radiation data, fluorescence data and chemiluminescence data are selectively recorded in a number of the absorptive regions 4 of the biochemical analysis unit 1 by selectively hybridizing a substance derived from a living organism and labeled with a radioactive labeling substance and a fluorescent substance with specific labeling substances fixed in a number of the absorptive regions 4 of the biochemical analysis unit 1, selectively hybridizing a substance derived from a living organism and labeled with a hapten such as digoxigenin with specific labeling substances fixed in a number of the absorptive regions 4 of the biochemical analysis unit 1 and further binding an antibody for the hapten labeled with an enzyme which generates chemiluminescence emission when it contacts a chemiluminescent substrate with the hapten labeling a substance derived from a living organism selectively hybridized with the specific binding substances by an antigen-antibody reaction. However, the application of the present invention is not limited to such reaction and the present invention can be applied to various kinds of a receptor-ligand association reactions.

Further, in the above described embodiments, chemiluminescence data are selectively recorded in a number of the absorptive regions 4 of the biochemical analysis unit 1 by selectively hybridizing a substance derived from a living organism and labeled with a hapten such as digoxigenin with specific labeling substances fixed in a number of the absorptive regions 4 of the biochemical analysis unit 1 and further binding an antibody for the hapten labeled with an enzyme which generates chemiluminescence emission when it contacts a chemiluminescent substrate with the hapten labeling a substance derived from a living organism and selectively hybridized with the specific binding substances fixed in a number of the absorptive regions 4 of the biochemical analysis unit 1 by an antigen-antibody reaction. However, chemiluminescence data may be selectively recorded in a number of the absorptive regions 4 of the biochemical analysis unit 1 by selectively hybridizing a substance derived from a living body and labeled with a labeling substance which generates chemiluminescence emission when it contacts a chemiluminescent substrate with specific binding substances fixed in a number of the absorptive regions 4 of the biochemical analysis unit 1.

Furthermore, in the above described embodiments, fluorescence data are selectively recorded in a number of the absorptive regions 4 of the biochemical analysis unit 1 by selectively hybridizing a substance derived from a living organism and labeled with a fluorescent substance with specific labeling substances fixed in a number of the absorptive regions 4 of the biochemical analysis unit 1. However, fluorescence data may be selectively recorded in a number of the absorptive regions 4 of the biochemical analysis unit 1 by selectively hybridizing a substance derived from a living organism and labeled with a hapten such as digoxigenin with specific labeling substances fixed in a number of the absorptive regions 4 of the biochemical analysis unit 1 and further binding an antibody for the hapten labeled with an enzyme which generates a fluorescence substance when it contacts a fluorescent substrate with the hapten labeling a substance derived from a living organism and selectively hybridized with the specific binding substances fixed in a number of the absorptive regions 4 of the biochemical analysis unit 1 by an antigen-antibody reaction.

Further, in the above described embodiments, the reaction solution 19 containing a substance derived from a living organism and labeled with a radioactive labeling substance, a fluorescent substance and a hapten such as digoxigenin is prepared and the substance derived from a living organism and labeled with a radioactive labeling substance, a fluorescent substance and a hapten such as digoxigenin is selectively hybridized with specific binding substances fixed in a number of the absorptive regions 4 of the biochemical analysis unit 1. However, it is not absolutely necessary for the reaction solution 19 to contain a substance derived from a living organism and labeled with a radioactive labeling substance, a fluorescent substance and a hapten such as digoxigenin and it is sufficient for the reaction solution 19 to contain a substance derived from a living organism and labeled with at least one of a radioactive labeling substance, a fluorescent substance and a hapten such as digoxigenin.

Moreover, in the above described embodiments, as specific binding substances, cDNAs each of which has a known base sequence and is different from the others are used. However, specific binding substances usable in the present invention are not limited to cDNAs but all specific binding substances capable of specifically binding with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, can be employed in the present invention as a specific binding substance.

Further, in the above described embodiments, although each of the electrodes 9$aa$, 9$ab$, 9$ac$, ..., 9$am$, ..., 9$nm$ and 150 is formed to have a cone-like shape, it is not absolutely necessary to form each of the electrodes 9$aa$, 9$ab$, 9$ac$, ..., 9$am$, ..., 9$nm$ and 150 so as have a cone-like shape and each of the electrodes 9$aa$, 9$ab$, 9$ac$, ..., 9$am$, ..., 9$nm$ and 150 may be formed in an arbitrary shape insofar as it can be inserted into each of the absorptive regions 4 formed in the substrate 2 of the biochemical analysis unit 1.

Furthermore, in the embodiment shown in FIGS. 1 to 20, the apparatus for conducting a receptor-ligand association reaction is constituted so as to control the switching operation of the switches 16$aa$, 16$ab$, 16$ac$, ..., 16$am$, ..., 16$nm$ of the electric field generating device 10, thereby sequentially connecting the electrodes 9$aa$, 9$ab$, 9$ac$, ..., 9$am$, ..., 9$nm$ to the positive power source 11 one at a time and connecting other electrodes to the ground terminal 12 and apply a positive voltage to the one electrode connected to the positive power source 11, thereby performing a hybridization reaction or an antigen-antibody reaction. However, the apparatus for conducting a receptor-ligand association reaction may be constituted so as to sequentially connect the electrodes 9$aa$, 9$ab$, 9$ac$, ..., 9$am$, ..., 9$nm$ to the positive power source 11 two or more at a time, connect other electrodes to the ground terminal 12 and apply a positive voltage to the two or more electrodes 9$aa$, 9$ab$, 9$ac$, ..., 9$am$, ..., 9$nm$ connected to the positive power source 11, thereby performing a hybridization reaction or an antigen-antibody reaction.

Moreover, in the embodiment shown in FIGS. 23 and 24, the apparatus for conducting a receptor-ligand association reaction is constituted so as to control the switching operation of the switches 141$a$, 141$b$, 141$c$, ..., 141$n$ of the electric field generating device 10, thereby sequentially connecting the electrodes of each of the electrode columns to the positive power source 11 and connecting the electrodes of other electrode columns to the ground terminal 12 and apply a positive voltage to the electrodes of the electrode column connected to the positive power source 11, thereby performing a hybridization reaction or an antigen-antibody reaction. However, the apparatus for conducting a receptor-ligand association reaction may be constituted so as to sequentially connect the electrodes of each of the electrode lines to the positive power source 11, connect the electrodes of other electrode lines to the ground terminal 12 and apply a positive voltage to the electrodes of the electrode line connected to the positive power source 11, thereby performing a hybridization reaction or an antigen-antibody reaction. Further, the apparatus for conducting a receptor-ligand association reaction may be constituted so as to sequentially connect electrodes included in sets of two or more electrode columns or sets of two or more electrode lines to the positive power source 11 at a time, connect the electrodes of other electrode columns or electrode lines to the ground terminal 12 and apply a positive voltage to the electrodes included in the two or more electrode columns or the two or more electrode lines to the ground terminal 12, thereby performing a hybridization reaction or an antigen-antibody reaction. Moreover, the apparatus for conducting a receptor-ligand association reaction may be constituted so as to sequentially connect a certain number of electrodes included in two or more electrode columns or two or more electrode lines to the positive power source 11 at a time, connect other electrodes to the ground terminal 12 and apply a positive voltage to the part of electrodes included in the two or more electrode columns or the two or more electrode lines, thereby performing a hybridization reaction or an antigen-antibody reaction.

Furthermore, in the embodiment shown in FIGS. 25 to 27, the apparatus for conducting a receptor-ligand association reaction is constituted so as to conduct a hybridization reaction or an antigen-antibody reaction by moving the single electrode 150 connected to the positive power source 11 using the main scanning pulse motor 166 and the sub-scanning pulse motor 162 by a constant pitch in the main scanning direction indicated by the arrow X and the sub-scanning direction indicated by the arrow Y in FIG. 26 and sequentially inserting the electrode 150 into each of the absorptive regions 4 formed in the substrate 2 of the biochemical analysis unit 1. However, it is not absolutely necessary to conduct a hybridization reaction or an antigen-antibody reaction by providing a single electrode 150, moving the electrode 150 using the main scanning pulse motor 166 and the sub-scanning pulse motor 162 by a constant pitch in the main scanning direction indicated by the arrow X and the sub-scanning direction indicated by the arrow Y in FIG. 27 and sequentially inserting the electrode 150 into each of the absorptive regions 4 formed in the substrate 2 of the biochemical analysis unit 1 and it is possible to conduct a hybridization reaction or an antigen-antibody reaction by providing 2 to n/2 electrodes or 2 to m/2 electrodes, connecting the 2 to n/2 electrodes or the 2 to m/2 electrodes to the positive power source 11, moving the 2 to n/2 electrodes or the 2 to m/2 electrodes using the main scanning pulse motor 166 and the sub-scanning pulse motor 162 by a constant pitch in the main scanning direction indicated by the arrow X and the sub-scanning direction indicated by the arrow Y in FIG. 27 and sequentially inserting them into the absorptive regions 4 formed in the substrate 2 of the biochemical analysis unit 1. Further, it is possible to conduct a hybridization reaction or an antigen-antibody reaction by providing n electrodes or m electrodes, connecting the n electrodes or the m electrodes to the positive power source 11, moving the n electrodes or the m electrodes using the main scanning pulse motor 166 and the sub-scanning pulse motor 162 by a constant pitch in the main scanning direction indicated by the arrow X and the sub-scanning direction indicated by the arrow Y in FIG. 27 and sequentially inserting them into the absorptive regions 4 formed in the substrate 2 of the biochemical analysis unit 1. Moreover, it is possible to conduct a hybridization reaction or an antigen-antibody reaction by providing 2n to (n×m) electrodes or 2m to (m×n) electrodes, connecting the 2n to (n×m) electrodes or the 2m to (m×n) electrodes to the positive power source 11, moving the 2n to (n×m) electrodes or the 2m to (m×n) electrodes using the main scanning pulse motor 166 and the sub-scanning pulse motor 162 by a constant pitch in the main scanning direction indicated by the arrow X and the sub-scanning direction indicated by the arrow Y in FIG. 27 and sequentially inserting them into the absorptive regions 4 formed in the substrate 2 of the biochemical analysis unit 1.

Further, in the embodiment shown in FIGS. 25 to 27, although the apparatus for conducting a receptor-ligand association reaction includes the solenoid 172 so that the electrode 150 can be inserted by the solenoid 172 into each of the absorptive regions 4 of the biochemical analysis unit 1, it is not absolutely necessary to insert the electrode 150 into each of the absorptive regions 4 of the biochemical analysis unit 1 using the solenoid 172 and it is possible to insert the electrode 150 into each of the absorptive regions 4 of the biochemical analysis unit 1 using other drive means such as a motor.

Furthermore, in the above described embodiments, although 19,200 substantially circular absorptive regions 4 having a size of about 0.01 mm$^2$ are formed in the substrate 2 of the biochemical analysis unit 1 in a regular pattern and in the manner of a matrix, the shape of each of the absorptive regions 4 is not limited to substantially a circular shape but may be formed in an arbitrary shape, for example, a rectangular shape.

Moreover, in the above described embodiments, although 19,200 substantially circular absorptive regions 4 having a size of about 0.01 mm$^2$ are formed in the substrate 2 of the biochemical analysis unit 1 in a regular pattern and in the manner of a matrix, the number or size of the absorptive regions 4, 154 may be arbitrarily selected in accordance with the purpose. Preferably, 10 or more of the absorptive regions 4 having a size of 5 mm$^2$ or less are formed in the biochemical analysis unit 1, 150 at a density of 10/cm$^2$ or greater.

Further, in the above described embodiments, although 19,200 substantially circular absorptive regions 4 having a size of about 0.01 mm are formed in the substrate 2 of the biochemical analysis unit 1 in a regular pattern and in the manner of a matrix, it is not absolutely necessary to form the absorptive regions 4 in a regular pattern.

Furthermore, in the above described embodiments, although the biochemical analysis unit 1 includes a number of the absorptive regions 4 formed by charging nylon-6 in a number of the through-hole 3 formed in the substrate 2 made of aluminum, it is not absolutely necessary to form a number of the absorptive regions 4 of the biochemical analysis unit 1 of nylon-6 but a number of the absorptive regions 4 of the biochemical analysis unit 1 may be formed of a porous material capable of forming a membrane filter other than nylon-6. Illustrative examples of a porous material usable for forming a number of the absorptive regions 4 of the biochemical analysis unit 1 include nylons such as nylon-6,6, nylon-4,10; cellulose derivatives such as nitrocellulose, acetyl cellulose, butyric-acetyl cellulose; collagen; alginic acids such as alginic acid, calcium alginate, alginic acid/poly-L-lysine polyionic complex; polyolefins such as polyethylene, polypropylene; polyvinyl chloride; polyvinylidene chloride; polyfluoride such as polyvinylidene fluoride, polytetrafluoride; and copolymers or composite materials thereof, and a porous carbon material such as an activated carbon. A number of the absorptive regions 4 of the biochemical analysis unit 1 may be formed of inorganic porous materials such as metals such as platinum, gold, iron, silver, nickel, aluminum and the like; metal oxides such as alumina, silica, titania, zeolite and the like; metal salts such as hydroxy apatite, calcium sulfate and the like; and composite materials thereof, and a plurality of fiber bundles.

Moreover, in the above described embodiments, although the biochemical analysis unit 1 includes the substrate made of aluminum, it is not absolutely necessary to make the substrate 2 of the biochemical analysis unit 1 of aluminum but the substrate 2 of the biochemical analysis unit 1 may be made of other kinds of material. The substrate 2 of the biochemical analysis unit 1 is preferably made of material capable of attenuating radiation energy and light energy but the material for forming the substrate 2 of the biochemical analysis unit 1 is not particularly limited. The substrate 2 of the biochemical analysis unit 1 can be formed of either inorganic compound material or organic compound material and is preferably formed of a metal material, a ceramic material or a plastic material. Illustrative examples of inorganic compound materials preferably usable for forming the substrate 2 of the biochemical analysis unit 1 include metals such as gold, silver, copper, zinc, aluminum, titanium, tantalum, chromium, steel, nickel, cobalt, lead, tin, selenium and the like; alloys such as brass, stainless, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. These may have either a monocrystal structure or a polycrystal sintered structure such as amorphous, ceramic or the like. High molecular compounds are preferably used as organic compound material for forming the substrate 2 of the biochemical analysis unit 1 and illustrative examples thereof include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifluoroethylene; polycarbonate; polyesters such as polyethylene naphthalate, polyethylene terephthalate and the like; nylons such as nylon-6, nylon-6,6, nylon-4,10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Further, in the above described embodiments, although a number of the absorptive regions 4 of the biochemical analysis unit 1 are formed by charging nylon-6 in a number of the through-hole 3 formed in the substrate 2 made of aluminum, a number of the absorptive regions 4 may be formed by charging nylon-6 in a number of recesses formed in the substrate 2 made of aluminum so as to be spaced apart from each other instead the through-holes 3.

Furthermore, in the above described embodiments, although a number of the absorptive regions 4 of the biochemical analysis unit 1 are formed by charging nylon-6 in a number of the through-hole 3 formed in the substrate 2 made of aluminum, a number of the absorptive regions 4 may be formed by pressing an absorptive membrane formed of an absorptive material such as nylon-6 into a number of the through-holes 3 formed in the substrate 2 made of aluminum.

Moreover, in the above described embodiments, although a number of the absorptive regions 4 of the biochemical analysis unit 1 are formed by charging nylon-6 in a number of the through-hole 3 formed in the substrate 2 made of aluminum, a number of absorptive regions may be formed by bringing a substrate formed with a number of through-holes into close contact with at least one surface of an absorptive substrate formed of an absorptive material and dropping a solution containing specific binding substances on the absorptive substrate within a number of the through-holes of the substrate.

Further, in the above described embodiments, although a number of the absorptive regions 4 of the biochemical analysis unit 1 are formed by charging nylon-6 in a number of the through-hole 3 formed in the substrate 2 made of aluminum, a number of absorptive regions may be formed by dropping a solution containing specific binding substances onto different positions on an absorptive substrate formed of an absorptive material.

According to the present invention, it is possible to provide a method for conducting a receptor-ligand association reaction and a reactor used therefor which can efficiently react a ligand or receptor with receptors or ligands fixed in spot-like regions of a biochemical analysis unit and produce biochemical analysis data having an excellent quantitative characteristic with good repeatability.

The invention claimed is:

1. A method for conducting a receptor-ligand association reaction comprising steps of dipping a biochemical analysis unit including a substrate formed with a plurality of absorptive regions which contain receptors or ligands and are formed to be spaced apart from each other in a reaction solution containing a target ligand or receptor labeled with a labeling substance, inserting at least one electrode into at least one of the plurality of absorptive regions of the biochemical analysis unit and applying a positive voltage to the at least one electrode, thereby selectively associating the target ligand or receptor contained in the reaction solution with the receptors or the ligands contained in the plurality of absorptive regions of the biochemical analysis unit.

2. A method for conducting a receptor-ligand association reaction in accordance with claim 1, wherein during the step of inserting a plurality of electrodes into all of the plurality of absorptive regions containing the receptors or ligands, a positive voltage is simultaneously applied to all of the plurality of electrodes, thereby conducting a receptor-ligand association reaction.

3. A method for conducting a receptor-ligand association reaction in accordance with claim 1, wherein during the step of inserting a plurality of electrodes into all of the plurality of absorptive regions containing the receptors or ligands, a positive voltage is sequentially applied to each of the plurality of electrodes at least one time while electrodes other than said each of the plurality of electrodes are grounded, thereby conducting a receptor-ligand association reaction.

4. A method for conducting a receptor-ligand association reaction in accordance with claim 1, wherein during the step of inserting a plurality of electrodes into all of the plurality of absorptive regions containing the receptors or ligands, a positive voltage is sequentially applied to at least two of the plurality of electrodes at a time while the plurality of electrodes other than said at least two of the plurality of electrodes are grounded, thereby conducting a receptor-ligand association reaction.

5. A method for conducting a receptor-ligand association reaction in accordance with claim 1 wherein the plurality of absorptive regions containing receptors or ligands are formed in the substrate of the biochemical analysis unit in the manner of a matrix consisting of m columns and n lines wherein m and n are integers equal to or greater than 2 and
   wherein during the step of simultaneously inserting a plurality of electrodes into all of the plurality of absorptive regions containing the receptors or ligands, a positive voltage is sequentially applied to the plurality of absorptive regions constituting individual columns of absorptive regions one column at a time while the absorptive regions constituting other columns of absorptive regions other than said one column are grounded, thereby conducting a receptor-ligand association reaction.

6. A method for conducting a receptor-ligand association reaction in accordance with claim 1 wherein the plurality of absorptive regions containing the receptors or ligands are formed in the substrate of the biochemical analysis unit in the manner of a matrix consisting of m columns and n lines wherein m and n are integers equal to or greater than 2 and wherein during the step of simultaneously inserting a plurality of electrodes into all of the plurality of absorptive regions containing the receptors or ligands, a positive voltage is sequentially applied to the plurality of absorptive regions constituting two or more columns among the plurality of absorptive regions at a time while the absorptive regions constituting other columns other than said one column are grounded, thereby conducting a receptor-ligand association reaction.

7. A method for conducting a receptor-ligand association reaction in accordance with claim 1 wherein the plurality of absorptive regions containing the receptors or ligands are formed in the substrate of the biochemical analysis unit in the manner of a matrix consisting of m columns and n lines wherein m and n are integers equal to or greater than 2 and wherein during the step of simultaneously inserting a plurality of electrodes into all of the plurality of absorptive regions containing the receptors or ligands, a positive voltage is sequentially applied to the plurality of absorptive regions constituting each line of absorptive regions one line at a time while the absorptive regions constituting other lines other than said one column of absorptive regions are grounded, thereby conducting a receptor-ligand association reaction.

8. A method for conducting a receptor-ligand association reaction in accordance with claim 1 wherein the plurality of absorptive regions containing the receptors or ligands are formed in the substrate of the biochemical analysis unit in the manner of a matrix consisting of m columns and n lines wherein m and n and n are integers equal to or greater than 2 and wherein during the step of simultaneously inserting a plurality of electrodes into all of the plurality of absorptive regions containing the receptors or ligands, a positive voltage is sequentially applied to the plurality of absorptive regions constituting two or more lines among the plurality of absorptive regions at a time while the absorptive regions constituting other lines other than said one column are grounded, thereby conducting a receptor-ligand association reaction.

9. A method for conducting a receptor-ligand association reaction in accordance with claim 1, wherein a receptor-ligand association reaction is conducted by sequentially inserting at least one electrode applied with a positive voltage at a time into the plurality of absorptive regions of the biochemical analysis unit.

10. A method for conducting a receptor-ligand association reaction in accordance with claim 9, wherein a receptor-ligand association reaction is conducted by sequentially inserting at least one electrode applied with a positive voltage at a time into the plurality of absorptive regions of the biochemical analysis unit.

11. A method for conducting a receptor-ligand association reaction in accordance with claim 9, wherein a receptor-ligand association reaction is conducted by sequentially inserting at least one electrode applied with a positive voltage at a time into the plurality of absorptive regions of the biochemical analysis unit.

12. A method for conducting a receptor-ligand association reaction in accordance with claim 1 wherein the target ligand or receptor is labeled with at least one kind of a labeling substance selected from a group consisting of a radioactive labeling substance, a fluorescent substance and a labeling substance which generates chemiluminescence emission when it contacts a chemiluminescent substrate.

13. A method for conducting a receptor-ligand association reaction in accordance with claim 2 wherein specific binding substances whose structure or characteristics are known are fixed in the plurality of absorptive regions of the biochemical analysis unit as the receptors or ligands and the target ligand or receptor is unit in the reaction solution containing a substance derived from a living organism and labeled with a labeling substance and further comprising a step of selectively hybridizing the substance derived from a living organism, labeled with a labeling substance and contained in the reaction solution with the specific binding substances fixed in the plurality of absorptive regions of the biochemical analysis unit.

14. A method for conducting a receptor-ligand association reaction in accordance with claim 3 wherein specific binding substances whose structure or characteristics are known are fixed in the plurality of absorptive regions of the biochemical analysis unit as the receptors or ligands and the target ligand or receptor is unit in the reaction solution containing a substance derived from a living organism and labeled with a labeling substance and further comprising a step of selectively hybridizing the substance derived from a living organism, labeled with a labeling substance and contained in the reaction solution with the specific binding substances fixed in the plurality of absorptive regions of the biochemical analysis unit.

15. A method for conducting a receptor-ligand association reaction in accordance with claim 4 wherein specific binding substances whose structure or characteristics are known are fixed in the plurality of absorptive regions of the biochemical analysis unit as the receptors or ligands and the target ligand or receptor is unit in the reaction solution containing a substance derived from a living organism and labeled with a labeling substance and further comprising a step of selectively hybridizing the substance derived from a living organism, labeled with a labeling substance and contained in the reaction solution with the specific binding substances fixed in the plurality of absorptive regions of the biochemical analysis unit.

16. A method for conducting a receptor-ligand association reaction in accordance with claim 5 wherein specific binding substances whose structure or characteristics are known are fixed in the plurality of absorptive regions of the biochemical analysis unit as the receptors or ligands and the target ligand or receptor is unit in the reaction solution containing a substance derived from a living organism and labeled with a labeling substance and furhter comprising a step of selectively hybridizing the substance derived from a living organism, labeled with a labeling substance and contained in the reaction solution with the specific binding substances fixed in the plurality of absorptive regions of the biochemical analysis unit.

17. A method for conducting a receptor-ligand association reaction in accordance with claim 6 wherein specific binding substances whose structure or characteristics are known are fixed in the plurality of absorptive regions of the biochemical analysis unit as the receptors or ligands and the target ligand or receptor is unit in the reaction solution containing a substance derived from a living organism and labeled with a labeling substance and further comprising a step of selectively hybridizing the substance derived from a living organism, labeled with a labeling substance and contained in the reaction solution with the specific binding substances fixed in the plurality of absorptive regions of the biochemical analysis unit.

18. A method for conducting a receptor-ligand association reaction in accordance with claim 7 wherein specific binding substances whose structure or characteristics are known are fixed in the plurality of absorptive regions of the biochemical analysis unit as the receptors or ligands and the target ligand or receptor is unit in the reaction solution containing a substance derived from a living organism and labeled with a labeling substance and further comprising a step of selectively hybridizing the substance derived from a living organism, labeled with a labeling substance and contained in the reaction solution with the specific binding substances fixed in the plurality of absorptive regions of the biochemical analysis unit.

19. A method for conducting a receptor-ligand association reaction in accordance with claim 8 wherein specific binding substances whose structure or characteristics are known are fixed in the plurality of absorptive regions of the biochemical analysis unit as the receptors or ligands and the target ligand or receptor is unit in the reaction solution containing a substance derived from a living organism and labeled with a labeling substance and further comprising a step of selectively hybridizing the substance derived from a living organism, labeled with a labeling substance and contained in the reaction solution with the specific binding substances fixed in the plurality of absorptive regions of the biochemical analysis unit.

20. A method for conducting a receptor-ligand association reaction in accordance with claim 9 wherein specific binding substances whose structure or characteristics are known are fixed in the plurality of absorptive regions of the biochemical analysis unit as the receptors or ligands and the target ligand or receptor is unit in the reaction solution containing a substance derived from a living organism and labeled with a labeling substance and further comprising a step of selectively hybridizing the substance derived from a living organism, labeled with a labeling substance and contained in the reaction solution with the specific binding substances fixed in the plurality of absorptive regions of the biochemical analysis unit.

21. A method for conducting a receptor-ligand association reaction in accordance with claim 10 wherein specific binding substances whose structure or characteristics are known are fixed in the plurality of absorptive regions of the biochemical analysis unit as the receptors or ligands and the target ligand or receptor is unit in the reaction solution containing a substance derived from a living organism and labeled with a labeling substance and further comprising a step of selectively hybridizing the substance derived from a living organism, labeled with a labeling substance and contained in the reaction solution with the specific binding substances fixed in the plurality of absorptive regions of the biochemical analysis unit.

22. A method for conducting a receptor-ligand association reaction in accordance with claim 11 wherein specific binding substances whose structure or characteristics are known are fixed in the plurality of absorptive regions of the biochemical analysis unit as the receptor or ligands and the target ligand or receptor is unit in the reaction solution containing a substance derived from a living organism and labeled with a labeling substance and further comprising a step of selectively hybridizing the substance derived from a living organism, labeled with a labeling substance and contained in the reaction solution with the specific binding substances fixed in the plurality of absorptive regions of the biochemical analysis unit.

23. A method for conducting a receptor-ligand association reaction in accordance with claim 1 wherein said receptors or ligands comprise antigens or antibodies the target receptors or ligands comprise an antibody or an antigen labeled target antibody or antigen and binding the with the antigens or the antibodies fixed in the plurality of absorptive regions of the biochemical analysis unit.

24. A method for conducting a receptor-ligand association reaction in accordance with claim 2 wherein specific binding substances whose structure or characteristics are known are fixed in the plurality of absorptive regions of the biochemical analysis unit as the receptors or ligands and the reaction solution containing a substance derived from a living organism and labeled with hapten as the target ligand or receptor, selectively hybridizing the target ligand or receptor with the specific binding substances fixed in the plurality of absorptive regions of the biochemical analysis unit, and the reaction solution further comprising an antibody for the hapten, wherein the antibody is labeled with a labeling enzyme, and further comprising a step of binding the antibody for the hapten with the hapten of the target ligand or receptor fixed in the plurality of absorptive regions of the biochemical analysis unit by an antigen-antibody reaction.

25. A method for conducting a receptor-ligand association reaction in accordance with claim 3 wherein specific binding substances whose structure or characteristics are known are fixed in the plurality of absorptive regions of the biochemical analysis unit as the receptors or ligands and the reaction solution containing a substance derived from a living organism and labeled with hapten as the target ligand or receptor, selectively hybridizing the target ligand or receptor with the specific binding substances fixed in the plurality of absorptive regions of the biochemical analysis unit, and the reaction solution further comprising an antibody for the hapten, wherein the antibody is labeled with a labeling enzyme, and further comprising a step of binding the antibody for the hapten with the hapten of the target ligand or receptor fixed in the plurality of absorptive regions of the biochemical analysis unit by an antigen-antibody reaction.

26. A method for conducting a receptor-ligand association reaction in accordance with claim 4 wherein specific binding substances whose structure or characteristics are known are fixed in the plurality of absorptive regions of the biochemical analysis unit as the receptors and ligands and the reaction solution containing a substance derived from a living organism and labeled with hapten as the target ligand or receptor, selectively hybridizing the target ligand or receptor with the specific binding substances fixed in the plurality of absorptive regions of the biochemical analysis unit, and the reaction solution further comprising an antibody for the hapten, wherein the antibody is labeled with a labeling enzyme, and further comprising a step of binding the antibody for the hapten with the hapten of the target ligand or receptor fixed in the plurality of absorptive regions of the biochemical analysis unit by an antigen-antibody reaction.

27. A method for conducting a receptor-ligand association reaction in accordance with claim 5 wherein specific binding substances whose structure or characteristics are known are fixed in the plurality of absorptive regions of the biochemical analysis unit as the receptors and ligands and the reaction solution containing a substance derived from a living organism and labeled with hapten as the target ligand or receptor, selectively hybridizing the target ligand or receptor with the specific binding substances fixed in the plurality of absorptive regions of the biochemical analysis unit, and the reaction solution further comprising an antibody for the hapten, wherein the antibody is labeled with a labeling enzyme, and further comprising a step of binding the antibody for the hapten with the hapten of the target ligand or receptor fixed in the plurality of absorptive regions of the biochemical analysis unit by an antigen-antibody reaction.

28. A method for conducting a receptor-ligand association reaction in accordance with claim 6 wherein specific binding substances whose structure or characteristics are known are fixed in the plurality of absorptive regions of the biochemical analysis unit as the receptors and ligands and the reaction solution containing a substance derived from a living organism and labeled with hapten as the target ligand or receptor, selectively hybridizing the target ligand or receptor with the specific binding substances fixed in the plurality of absorptive regions of the biochemical analysis unit, and the reaction solution further comprising an antibody for the hapten, wherein the antibody is labeled with a labeling enzyme, and further comprising a step of binding the antibody for the hapten with the hapten of the target ligand or receptor fixed in the plurality of absorptive regions of the biochemical analysis unit by an antigen-antibody reaction.

29. A method for conducting a receptor-ligand association reaction in accordance with claim 7 wherein specific binding substances whose structure or characteristics are known are fixed in the plurality of absorptive regions of the biochemical analysis unit as the receptors and ligands and the reaction solution containing a substance derived from a living organism and labeled with hapten as the target ligand or receptor, selectively hybridizing the target ligand or receptor with the specific binding substances fixed in the plurality of absorptive regions of the biochemical analysis unit, and the reaction solution further comprising an antibody for the hapten, wherein the antibody is labeled with a labeling enzyme, and further comprising a step of binding the antibody for the hapten with the hapten of the target ligand or receptor fixed in the plurality of absorptive regions of the biochemical analysis unit by an antigen-antibody reaction.

30. A method for conducting a receptor-ligand association reaction in accordance with claim 8 wherein specific binding substances whose structure or characteristics are known are fixed in the plurality of absorptive regions of the biochemical analysis unit as the receptors and ligands and the reaction solution containing a substance derived from a living organism and labeled with hapten as the target ligand or receptor, selectively hybridizing the target ligand or receptor with the specific binding substances fixed in the plurality of absorptive regions of the biochemical analysis unit, and the reaction solution further comprising an antibody for the hapten, wherein the antibody is labeled with a labeling enzyme, and further comprising a step of binding the antibody for the hapten with the hapten of the target ligand or receptor fixed in the plurality of absorptive regions of the biochemical analysis unit by an antigen-antibody reaction.

31. A method for conducting a receptor-ligand association reaction in accordance with claim 9 wherein specific binding substances whose structure or characteristics are known are fixed in the plurality of absorptive regions of the biochemical analysis as the receptors and ligands unit and the reaction solution containing a substance derived from a living organism and labeled with hapten as the target ligand or receptor, selectively hybridizing the target ligand or receptor with the specific binding substances fixed in the plurality of absorptive regions of the biochemical analysis unit, and the reaction solution further comprising an antibody for the hapten, wherein the antibody is labeled with a labeling enzyme, and further comprising a step of binding the antibody for the hapten with the hapten of the target ligand or receptor fixed in the plurality of absorptive regions of the biochemical analysis unit by an antigen-antibody reaction.

32. A method for conducting a receptor-ligand association reaction in accordance with claim 10 wherein specific binding substances whose structure or characteristics are known are fixed in the plurality of absorptive regions of the biochemical analysis unit as the receptors and ligands and the reaction solution containing a substance derived from a living organism and labeled with hapten as the target ligand or receptor, selectively hybridizing the target ligand or receptor with the specific binding substances fixed in the plurality of absorptive regions of the biochemical analysis unit, and the reaction solution further comprising an antibody for the hapten, wherein the antibody is labeled with a labeling enzyme, and further comprising a step of binding the antibody for the hapten with the hapten of the target ligand or receptor fixed in the plurality of absorptive regions of the biochemical analysis unit by an antigen-antibody reaction.

33. A method for conducting a receptor-ligand association reaction in accordance with claim 11 wherein specific binding substances whose structure or characteristics are known are fixed in the plurality of absorptive regions of the biochemical analysis unit as the receptors and ligands and the reaction solution containing a substance derived from a living organism and labeled with hapten as the target ligand or receptor, selectively hybridizing the target ligand or receptor with the specific binding substances fixed in the plurality of absorptive regions of the biochemical analysis unit, and the reaction solution further comprising an antibody for the hapten, wherein the antibody is labeled with a labeling enzyme, and further comprising a step of binding the antibody for the hapten with the hapten of the target ligand or receptor fixed in the plurality of absorptive regions of the biochemical analysis unit by an antigen-antibody reaction.

34. A method for conducting a receptor-ligand association reaction in accordance with claim 1 wherein the target ligand or receptor is a substance derived from a living organism and labeled with hapten, and the method further comprises a step of selectively hybridizing the labeled target ligand or receptor with the specific binding substances fixed in the plurality of absorptive regions of the biochemical analysis unit as the receptors or ligand, and the reaction solution further comprises an antibody for the hapten, wherein the antibody is labeled with labeled with an enzyme which generates chemiluminescence emission when it contacts a chemiluminescent substrate, and further comprising a step of binding the antibody labeled with the enzyme with the hapten of the target ligand or receptor fixed in the plurality of absorptive regions of the biochemical analysis unit by an antigen-antibody reaction.

35. A method for conducting a receptor-ligand association reaction in accordance with claim 1 wherein the target ligand or receptor is a substance derived from a living organism and labeled with hapten, the method further comprising a step of selectively hybridizing the target ligand or receptor, labeled with the hapten, with specific binding substances fixed in the plurality of absorptive regions of the biochemical analysis unit as the receptors or ligand, and wherein the reaction solution contains an antibody for the hapten labeled with an enzyme which generates a fluorescence substance when it contacts a fluorescent substrate, and the method further comprising a step of binding the antibody labeled with the enzyme with the hapten fixed in the plurality of absorptive regions of the biochemical analysis unit by an antigen-antibody reaction.

36. A method for conducting a receptor-ligand association reaction in accordance with claim 1 wherein the biochemical analysis unit includes a substrate formed with a plurality of holes to be spaced apart from each other and the plurality of absorptive regions are formed by charging an absorptive material in the plurality of holes formed in the substrate and causing the absorptive material charged in the plurality of holes in to contain the receptors or ligands.

37. A method for conducting a receptor-ligand association reaction in accordance with claim 36 wherein the biochemical analysis unit includes a substrate formed with a plurality of through-holes to be spaced apart from each other and the plurality of absorptive regions are formed by pressing an absorptive membrane containing an absorptive material into the plurality of through-holes formed in the substrate and causing the absorptive membrane pressed in the plurality of through-holes to contain the receptors or ligands.

38. A method for conducting a receptor-ligand association reaction in accordance with claim 36 wherein the substrate of the biochemical analysis unit is capable of attenuating radiation energy.

39. A method for conducting a receptor-ligand association reaction in accordance with claim 38 wherein the substrate of the biochemical analysis unit is made of a material that reduces the energy of radiation to $1/5$ or less when the radiation travels in the substrate by a distance equal to that between neighboring absorptive regions.

40. A method for conducting a receptor-ligand association reaction in accordance with claim 36 wherein the substrate of the biochemical analysis unit is capable of attenuating light energy.

41. A method for conducting a receptor-ligand association reaction in accordance with claim 40 wherein the substrate of the biochemical analysis unit is made of a material that reduces the energy of light to $1/5$ or less when the light travels in the substrate by a distance equal to that between neighboring absorptive regions.

42. A method for conducting a receptor-ligand association reaction in accordance with claim 1 wherein the biochemical analysis unit is formed with 10 or more absorptive regions.

43. A method for conducting a receptor-ligand association reaction in accordance with claim 1 wherein each of the plurality of absorptive regions formed in the biochemical analysis unit has a size of less than 5 mm$^2$.

44. A method for conducting a receptor-ligand association reaction in accordance with claim 1 wherein the plurality of absorptive regions are formed in the biochemical analysis unit at a density of 10 or more per cm$^2$.

* * * * *